United States Patent [19]
Riggs et al.

[11] Patent Number: 6,066,483
[45] Date of Patent: May 23, 2000

[54] **PURIFIED DNA POLYMERASE FROM *BACILLUS STEAROTHERMOPHILUS***

[75] Inventors: Michael Garth Riggs; Mathoor Sivaram; Starla Dianne Tudor, all of San Diego, Calif.

[73] Assignee: Gen-Probe Incorporated, San Diego, Calif.

[21] Appl. No.: 09/135,642

[22] Filed: Aug. 18, 1998

Related U.S. Application Data

[62] Division of application No. 08/436,664, May 8, 1995, Pat. No. 5,874,282, which is a division of application No. 08/394,232, Feb. 24, 1995, which is a continuation-in-part of application No. 08/307,410, Sep. 16, 1994, abandoned, which is a continuation-in-part of application No. 08/222,612, Apr. 1, 1994, abandoned.

[51] Int. Cl.$^7$ ................................................. C12N 9/12
[52] U.S. Cl. .......................................................... 435/194
[58] Field of Search ............................................. 435/194

[56] References Cited

U.S. PATENT DOCUMENTS

| | | |
|---|---|---|
| 4,889,818 | 12/1989 | Gelfand et al. . |
| 5,079,352 | 1/1992 | Gelfand et al. . |
| 5,436,326 | 7/1995 | Ishino et al. . |
| 5,466,591 | 11/1995 | Abramson et al. . |

FOREIGN PATENT DOCUMENTS

| | | |
|---|---|---|
| 0455430 | 11/1991 | European Pat. Off. . |
| 0482714 | 4/1992 | European Pat. Off. . |
| 0497272 | 8/1992 | European Pat. Off. . |
| 0517418 | 12/1992 | European Pat. Off. . |
| 0547359 | 6/1993 | European Pat. Off. . |
| 0547920 | 6/1993 | European Pat. Off. . |
| 5304964 | 11/1993 | Japan . |
| 9206188 | 4/1992 | WIPO . |
| 9206202 | 4/1992 | WIPO . |
| 9416107 | 7/1994 | WIPO . |
| 9503430 | 2/1995 | WIPO . |

OTHER PUBLICATIONS

Joyce, C., and N.D.F. Grindley, Construction of a plasmid that overproduces the large proteolytic fragment (Klenow fragment) of DNA polymerase I of *Escherichia coli*. *Proc. Natl. Acad. Sci. USA* 80:1830–1834 (1983).

Lawyer, F.C., et al. High–level expression, purification, and enzymatic characterization of full–length Thermus aquaticus DNA polymerase and a truncated form deficient in 5' to 3' exonuclease activity. In *Research: PCR Methods and Applications* 2:275–287, Cold Spring Harbor Laboratory Press, Cold Spring Harbor, New York (1993).

Livingston, D.M. et al. Affinity Chromatography of Avian Type C Viral Reverse Transcriptase: Studies with Rous Sarcoma Virus Transformed Rat Cells. *Virology* 50:388–395 (1972).

Naheuer, H.P. and F. Grosse, Immunoaffinity–Purified DNA Polymerase Displays Novel Properties *Biochemistry* 26:84588466 (1987).

Pisani, F.M., et al. A DNA polymerase from the archeon Sulfolobus solfataricus hows sequence similarity to family B DNA polymerases. *Nucleic Acids Res.* 20(11):2711–2716 (1992).

Spadari, S. and A. Weissbach. HeLa Cell R–Deoxyribonucleic Acid Polymerases. *J. Biol. Chem.* 249(18):5809–5815 (1974).

Uemori, T., et al. Organization and nucleotide sequence of the DNA polymerase gene from the archeon Pyrococcus furiosus. *Nucleic Acids Res.* 21(2):259–265 (1993).

Uemori, et al., Cloning of the DNA Polymerase Gene of *Bacillus caldotenax* and Characterization of the Gene Product. *J. Biochem.* 113:401–410 (1993).

Joyce, et al. Genetic mapping and DNA sequence analysis of mutations in the polA gene of *Escherichia coli*. *J. Mol. Biochem.* 186:283–293 (1985).

Phang, S., et al., Cloning and complete sequence of the DNA ploymerase–encoding gene (Bstpol I) and characterisation of the Klenow–like fragment from *Bacillus stearothermophilus*, Gene, 163:65–86 (1995).

Lu, Y., et al., Large Fragment of DNA Polymerase I from *Bacillus stearothermophilus* (Bst Polymerase) is Stable at Ambient Temperature, *Biotechniques*, 11(4):464, 466 (1991).

McClary, J., et al., Sequencing with the large fragment of DNA polymerase I from *Bacillus stearothermophilus*, *DNA Sequence*, 1:173–180 (1991).

Lawyer, F., et al., Isolation, Characterization, and Expression in *Escherichia coli* of the DNA Polymerase Gene from *Thermus aquaticus*, *J. of Biological Chemistry*, 264(11):6427–6437 (1989).

Bernad, A., et al., A Conserved 3'—5' Exonuclease Active Site in Prokaryotic and Eukaryotic DNA Polymerases, *Cell*, 59:219–228 (1989).

Biological Abstracts, vol. BA84, Philadelphia, PA, USA; Abstract No.: 97671, Ye, S., et al., Heat–Stable DNA Polymerase I Large Fragment Resolves Hairpin Structure In DNA Sequencing.

Database WPI, Derwent Publications Ltd., London, G.B.; AN 88–203377 & SU–A–1 311251 (Lengd Nucler Phys), Jan. 30, 1988 (Abstract).

Stenesh, et al., *Biochem. Biophys. Acta*, 272:156–166 (1972).

Kaboev, et al., *J. Bact.*, 145(1):21–26 (1981).

Kaboev et al. *J. Bact.*, 145: 21–26, 1981.

Phang et al. *Gene*, 163: 65–68, 1995.

*Primary Examiner*—Keith D. Hendricks
*Attorney, Agent, or Firm*—Christine A. Gritzmacher

[57] ABSTRACT

Composition and methods for the expression of recombinant DNA polymerase enzymes derived from *Bacillus stearothermophilus*. The present invention also concerns methods for purifying recombinant Bst DNA polymerase enzymes, compositions containing the purified enzymes in a form suitable for conducting biochemical reactions, and methods for using the purified enzymes.

21 Claims, 16 Drawing Sheets

Oligo 15
(SEQ ID NO:13)  5' TTAATCGACGGCAGCAGCGTGGGCTACCGCGCCTTTTCGCCTTG 3'

Oligo 21
(SEQ ID NO:9)   5' TTGATGGGTGATAAGTCGGATAACATTCCTGGGT 3'

Oligo 16
(SEQ ID NO:1)   5' GAGCAGCGGCATTTATGAGCTCGCCGGGCCAAGAATTCAA 3'

Oligo 17
(SEQ ID NO:5)   5' AATTCACCGAAACAGCTCGGTCAATTTATTTGAAAA 3'

Oligo 20
(SEQ ID NO:11)  3' TTTTGGCCCGATGAGGTGTAGTCGCCTACACGACCTT 5'

Oligo 24
(SEQ ID NO:7)   3' GCCGCGGCGATAAACGGCCTATAATGCTCGGGCGTGAAGTT 5'

Oligo 25
(SEQ ID NO:3)   3' GGCTAAGTTCCCTCGGCGGCGACTGTAATAATTTTCCGCTAC 5'

FIG. 1

COORDINATES ASSUME AMPLICON = 1143bp

| | 5'-3' exo | 3'-5' exo | polymerase | |
|---|---|---|---|---|
| | ↑ 15 | ↑ 21 | ↑ ↑ 16 20 | ↑ ↑ 24 25 |

Sst I FRAGMENT
SIZES

| | | | | |
|---|---|---|---|---|
| > 9 kb | | | | X |
| ≤ 9 | X | | | |
| 2.1 | | | X  X | X  X |
| LOW | X | X | | |

FIG. 5

(1) CUT GENOMIC CLONE pGem Bst 2.1 Sst
WITH Hind III+ Sal I AND GEL ISOLATE THE 3'
GENE FRAGMENT PLUS EXTRA DOWNSTREAM
SEQUENCE = FRAGMENT A
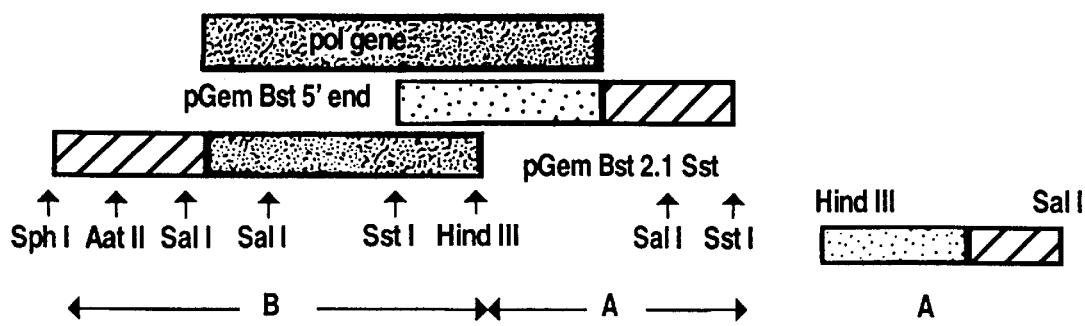
(2) CUT pUC18 WITH Hind III +
Sal I AND GEL ISOLATE VECTOR FRAGMENT
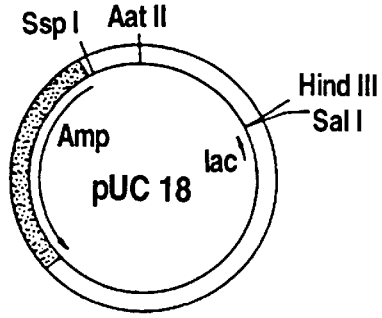
FIG. 8A (3) LIGATE FRAGMENT A WITH pUC18
VECTOR FRAGMENT = pUC Bst 3'end
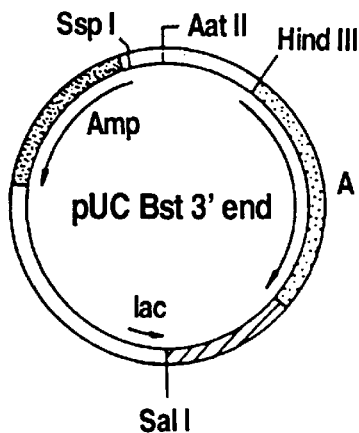
(4) CUT AND GEL ISOLATE THE Aat II + Hind III 5' GENE
FRAGMENT FROM pGem Bst 5'end = FRAGMENT B
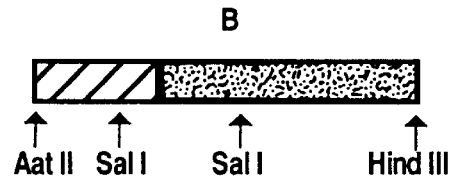
(5) CUT pUC Bst 3' end FROM STEP 3 WITH
Aat II + Hind III AND GEL ISOLATE THE
LARGE VECTOR/Bst FRAGMENT
(6) LIGATE THE ABOVE pUC Bst 3' end
VECTOR/Bst FRAGMENT WITH FRAGMENT B
AND SELECT FULL LENGTH CLONE pUC Bst #1
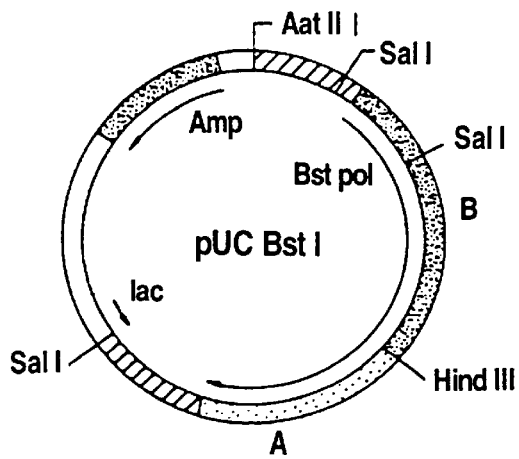
FIG. 8B

N-TERMINAL ALIGNMENTS OF KLENOW TYPE ENZYMES

| | FIRST aa coordinate | Sequence |
|---|---|---|
| Bca DNA POLYMERASE | | - - - E S P S S E E E K P L A K M A F T L A D R V T E E M L A D K A A L V V E - - |
| UNCLONED Bst SUBTILISIN FRAGMENT (Bio-Rad) | | A E G E K P L E E M E F A I V D V I T E E M L A D K L A L V V E - - |
| Bst 1 ENZYME | | - - M A V Q T D E G E K P L A G M D F A I A D S V T D E M L A D K A A L V V E - - |
| Bst 2 ENZYME | 290 | D E G E K P L A G M D F A I A D S V T D E M L A D K A A L V V E - - |
| Bst 1 SUBTILISIN FRAGMENT | 289 | T D E G E K P L A G M D F A I A D S V T D E M L A D K A A L V V E - - |
| Bst 3 NATURALLY OCCURRING CLEAVAGE PRODUCT AND Bst 4 ENZYME | 287 | V Q T D E G E K P L A G M D F A I A D S V T D E M L A D K A A L V V E - - |

FIG.12

SDS PAGE (10%) of Lysates and Purified Bst Polymerase

1. Molecular Weight Markers (98kD, 66kD, 45 kD, 31 kD)
2. Negative Control Lysate
3. Bst-1 Clone Lysate
4. Purified Bst-1
5. Purified Bst-1 Subtilisin Fragment
6. Purified Bst-3
7. Purified Bst-3 Fragment

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

GAGCAGCGCA TTTATGAGCT CGCCGGCCAA GAATTCAA                    38

(2) INFORMATION FOR SEQ ID NO:2:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

TTGAATTCTT GGCCGGCGAG CTCATAAATG CGCTGCTC                    38

(2) INFORMATION FOR SEQ ID NO:3:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CATCGCCTTT TTAATAATGT CAGCGGCGCT CCCTTGAATC GG               42

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

CCGATTCAAG GGAGCGCCGC TGACATTATT AAAAAGGCGA TG                42

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

AATTCACCGA AACAGCTCGG CGTCAATTTA TTTGAAAA                    38

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TTTTCAAATA AATTGACGCC GAGCTGTTTC GGTGAATT                    38

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

TTGAAGTTGC GGCTCGTAAT ATCCGGCAAA TAGCGGCGCC G                41

(2) INFORMATION FOR SEQ ID NO:8:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CGGCGCCGCT ATTTGCCGGA TATTACGAGC CGCAACTTCA A                41

(2) INFORMATION FOR SEQ ID NO:9:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

TTGATGGGTG ATAAGTCGGA TAACATTCCT GGGGT                       35

(2) INFORMATION FOR SEQ ID NO:10:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

ACCCCAGGAA TGTTATCCGA CTTATCACCC ATCAA                       35

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

```
TTCCAGCACA TCCGCTGATG TGGAGTAGCC GGTTTT                                    36
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

```
AAAACCGGCT ACTCCACATC AGCGGATGTG CTGGAA                                    36
```

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

```
TTAATCGACG GCAGCAGCGT GGCGTACCGC GCCTTTTTCG CCTTG                          45
```

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

CAAGGCGAAA AAGGCGCGGT ACGCCACGCT GCTGCCGTCG ATTAA                45

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

GATTTAGGTG ACACTATAG                                    19

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

TAATACGACT CACTATAGGG                                 20

(2) INFORMATION FOR SEQ ID NO:17:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

```
AGCATGCCAT GGATGAAGGC GAAAAGCCGC TCGCCGGGAT GGATTTTGCG ATCGCCGACA        60

GCGTCACGGA CGAAATGCTC GCCGACAAAG CGGC                                    94
```

(2) INFORMATION FOR SEQ ID NO:18:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

```
CAGACACCAA GGCGATCCCG ACAATCGGGG CATGGTGATA GTTGTCGCCC ACCACCTCCA        60

CGACGAGGGC CGCTTTGTCG GCGAGCATTT CGTCCG                                  96
```

(2) INFORMATION FOR SEQ ID NO:19:

(i) SEQUENCE CHARACTERISTICS:
        (A) LENGTH: 2761 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 103...2730
        (D) OTHER INFORMATION:

(xi) SEQUENCE DESCRIPTION: SEQ ID NO:19:

```
TTTACGATTC ATTTCCCGAA GCCGGAGCGG TAGCCGGCTT CTTTTTATGG CCGCCCGCCG        60

GCGTGGTACA ATAGAACAAG GAACGTCCGA GGAGGGATGA TG TTG AAA AAC AAG          114
                                              Leu Lys Asn Lys
                                                1

CTC GTC TTA ATT GAC GGC AAC AGC GTG GCG TAC CGC GCC TTT TTC GCG         162
Leu Val Leu Ile Asp Gly Asn Ser Val Ala Tyr Arg Ala Phe Phe Ala
  5                  10                  15                  20

TTG CCG CTT TTG CAT AAC GAT AAA GGG ATT CAT ACG AAC GCA GTC TAC         210
Leu Pro Leu Leu His Asn Asp Lys Gly Ile His Thr Asn Ala Val Tyr
                25                  30                  35

GGG TTT ACG ATG ATG TTA AAC AAA ATT TTG GCG GAA GAG CAG CCG ACC         258
Gly Phe Thr Met Met Leu Asn Lys Ile Leu Ala Glu Glu Gln Pro Thr
         40                  45                  50

CAC ATT CTC GTG GCG TTT GAC GCC GGG AAA ACG ACG TTC CGC CAT GAA         306
His Ile Leu Val Ala Phe Asp Ala Gly Lys Thr Thr Phe Arg His Glu
     55                  60                  65

ACG TTC CAA GAC TAT AAA GGC GGG CGG CAG CAG ACG CCG CCG GAA CTG         354
```

```
Thr Phe Gln Asp Tyr Lys Gly Gly Arg Gln Gln Thr Pro Pro Glu Leu
 70                  75                  80

TCG GAA CAG TTT CCG CTG CTG CGC GAA TTG CTC AAG GCG TAC CGC ATC        402
Ser Glu Gln Phe Pro Leu Leu Arg Glu Leu Leu Lys Ala Tyr Arg Ile
 85                  90                  95                 100

CCC GCC TAT GAG CTC GAC CAT TAC GAA GCG GAC GAT ATT ATC GGA ACG        450
Pro Ala Tyr Glu Leu Asp His Tyr Glu Ala Asp Asp Ile Ile Gly Thr
                105                 110                 115

ATG GCG GCG CGG GCT GAG CGA GAA GGG TTT GCA GTG AAA GTC ATT TCC        498
Met Ala Ala Arg Ala Glu Arg Glu Gly Phe Ala Val Lys Val Ile Ser
            120                 125                 130

GGC GAC CGC GAT TTA ACC CAG CTT GCT TCC CCG CAA GTG ACG GTG GAG        546
Gly Asp Arg Asp Leu Thr Gln Leu Ala Ser Pro Gln Val Thr Val Glu
        135                 140                 145

ATT ACG AAA AAA GGG ATT ACC GAC ATC GAG TCG TAC ACG CCG GAG ACG        594
Ile Thr Lys Lys Gly Ile Thr Asp Ile Glu Ser Tyr Thr Pro Glu Thr
150                 155                 160

GTC GTG GAA AAA TAC GGC CTC ACC CCG GAG CAA ATT GTC GAC TTG AAA        642
Val Val Glu Lys Tyr Gly Leu Thr Pro Glu Gln Ile Val Asp Leu Lys
165                 170                 175                 180

GGA TTG ATG GGC GAC AAA TCC GAC AAC ATC CCT GGC GTG CCC GGC ATC        690
Gly Leu Met Gly Asp Lys Ser Asp Asn Ile Pro Gly Val Pro Gly Ile
                185                 190                 195

GGG GAA AAA ACA GCC GTC AAG CTG CTC AAG CAA TTC GGC ACG GTC GAA        738
Gly Glu Lys Thr Ala Val Lys Leu Leu Lys Gln Phe Gly Thr Val Glu
            200                 205                 210

AAC GTA CTG GCA TCG ATC GAT GAG ATC AAA GGG GAG AAG CTG AAA GAA        786
Asn Val Leu Ala Ser Ile Asp Glu Ile Lys Gly Glu Lys Leu Lys Glu
        215                 220                 225

AAT TTG CGC CAA TAC CGG GAT TTG GCG CTT TTA AGC AAA CAG CTG GCC        834
Asn Leu Arg Gln Tyr Arg Asp Leu Ala Leu Leu Ser Lys Gln Leu Ala
230                 235                 240

GCT ATT TGC CGC GAC GCC CCG GTT GAG CTG ACG CTC GAT GAC ATT GTC        882
Ala Ile Cys Arg Asp Ala Pro Val Glu Leu Thr Leu Asp Asp Ile Val
245                 250                 255                 260

TAC AAA GGA GAA GAC CGG GAA AAA GTG GTC GCC TTG TTT CAG GAG CTC        930
Tyr Lys Gly Glu Asp Arg Glu Lys Val Val Ala Leu Phe Gln Glu Leu
                265                 270                 275

GGA TTC CAG TCG TTT CTC GAC AAG ATG GCC GTC CAA ACG GAT GAA GGC        978
Gly Phe Gln Ser Phe Leu Asp Lys Met Ala Val Gln Thr Asp Glu Gly
            280                 285                 290

GAA AAG CCG CTC GCC GGG ATG GAT TTT GCG ATC GCC GAC AGC GTC ACG       1026
Glu Lys Pro Leu Ala Gly Met Asp Phe Ala Ile Ala Asp Ser Val Thr
        295                 300                 305

GAC GAA ATG CTC GCC GAC AAA GCG GCC CTC GTC GTG GAG GTG GTG GGC       1074
Asp Glu Met Leu Ala Asp Lys Ala Ala Leu Val Val Glu Val Val Gly
310                 315                 320

GAC AAC TAT CAC CAT GCC CCG ATT GTC GGG ATC GCC TTG GCC AAC GAA       1122
Asp Asn Tyr His His Ala Pro Ile Val Gly Ile Ala Leu Ala Asn Glu
325                 330                 335                 340

CGC GGG CGG TTT TTC CTG CGC CCG GAG ACG GCG CTC GCC GAT CCG AAA       1170
Arg Gly Arg Phe Phe Leu Arg Pro Glu Thr Ala Leu Ala Asp Pro Lys
                345                 350                 355

TTT CTC GCT TGG CTT GGC GAT GAG ACG AAG AAA AAA ACG ATG TTT GAT       1218
Phe Leu Ala Trp Leu Gly Asp Glu Thr Lys Lys Lys Thr Met Phe Asp
            360                 365                 370

TCA AAG CGG GCG GCC GTC GCG CTA AAA TGG AAA GGA ATC GAA CTG CGC       1266
Ser Lys Arg Ala Ala Val Ala Leu Lys Trp Lys Gly Ile Glu Leu Arg
        375                 380                 385
```

```
GGC GTC GTG TTC GAT CTG TTG CTG GCC GCT TAC TTG CTC GAT CCG GCG      1314
Gly Val Val Phe Asp Leu Leu Leu Ala Ala Tyr Leu Leu Asp Pro Ala
    390                 395                 400

CAG GCG GCG GGC GAC GTT GCC GCG GTG GCG AAA ATG CAT CAG TAC GAG      1362
Gln Ala Ala Gly Asp Val Ala Ala Val Ala Lys Met His Gln Tyr Glu
405                 410                 415                 420

GCG GTG CGA TCG GAT GAG GCG GTC TAT GGA AAA GGA GCG AAG CGG ACG      1410
Ala Val Arg Ser Asp Glu Ala Val Tyr Gly Lys Gly Ala Lys Arg Thr
                425                 430                 435

GTT CCT GAT GAA CCG ACG CTT GCC GAG CAT CTC GCC CGC AAG GCG GCG      1458
Val Pro Asp Glu Pro Thr Leu Ala Glu His Leu Ala Arg Lys Ala Ala
                    440                 445                 450

GCC ATT TGG GCG CTT GAA GAG CCG TTG ATG GAC GAA CTG CGC CGC AAC      1506
Ala Ile Trp Ala Leu Glu Glu Pro Leu Met Asp Glu Leu Arg Arg Asn
                455                 460                 465

GAA CAA GAT CGG CTG CTG ACC GAG CTC GAA CAG CCG CTG GCT GGC ATT      1554
Glu Gln Asp Arg Leu Leu Thr Glu Leu Glu Gln Pro Leu Ala Gly Ile
    470                 475                 480

TTG GCC AAT ATG GAA TTT ACT GGA GTG AAA GTG GAC ACG AAG CGG CTT      1602
Leu Ala Asn Met Glu Phe Thr Gly Val Lys Val Asp Thr Lys Arg Leu
485                 490                 495                 500

GAA CAG ATG GGG GCG GAG CTC ACC GAG CAG CTG CAG GCG GTC GAG CGG      1650
Glu Gln Met Gly Ala Glu Leu Thr Glu Gln Leu Gln Ala Val Glu Arg
                505                 510                 515

CGC ATT TAC GAA CTC GCC GGC CAA GAG TTC AAC ATT AAC TCG CCG AAA      1698
Arg Ile Tyr Glu Leu Ala Gly Gln Glu Phe Asn Ile Asn Ser Pro Lys
                520                 525                 530

CAG CTC GGG ACG GTT TTA TTT GAC AAG CTG CAG CTC CCG GTG TTG AAA      1746
Gln Leu Gly Thr Val Leu Phe Asp Lys Leu Gln Leu Pro Val Leu Lys
    535                 540                 545

AAG ACA AAA ACC GGC TAT TCG ACT TCA GCC GAT GTG CTT GAG AAG CTT      1794
Lys Thr Lys Thr Gly Tyr Ser Thr Ser Ala Asp Val Leu Glu Lys Leu
550                 555                 560

GCA CCG CAC CAT GAA ATC GTC GAA CAT ATT TTG CAT TAC CGC CAA CTC      1842
Ala Pro His His Glu Ile Val Glu His Ile Leu His Tyr Arg Gln Leu
565                 570                 575                 580

GGC AAG CTG CAG TCA ACG TAT ATT GAA GGG CTG CTG AAA GTG GTG CAC      1890
Gly Lys Leu Gln Ser Thr Tyr Ile Glu Gly Leu Leu Lys Val Val His
                585                 590                 595

CCC GTG ACG GGC AAA GTG CAC ACG ATG TTC AAT CAG GCG TTG ACG CAA      1938
Pro Val Thr Gly Lys Val His Thr Met Phe Asn Gln Ala Leu Thr Gln
                600                 605                 610

ACC GGG CGC CTC AGC TCC GTC GAA CCG AAT TTG CAA AAC ATT CCG ATT      1986
Thr Gly Arg Leu Ser Ser Val Glu Pro Asn Leu Gln Asn Ile Pro Ile
                615                 620                 625

CGG CTT GAG GAA GGG CGG AAA ATC CGC CAG GCG TTC GTG CCG TCG GAG      2034
Arg Leu Glu Glu Gly Arg Lys Ile Arg Gln Ala Phe Val Pro Ser Glu
    630                 635                 640

CCG GAC TGG CTC ATC TTT GCG GCC GAC TAT TCG CAA ATC GAG CTG CGC      2082
Pro Asp Trp Leu Ile Phe Ala Ala Asp Tyr Ser Gln Ile Glu Leu Arg
645                 650                 655                 660

GTC CTC GCC CAT ATC GCG GAA GAT GAC AAT TTG ATT GAA GCG TTC CGG      2130
Val Leu Ala His Ile Ala Glu Asp Asp Asn Leu Ile Glu Ala Phe Arg
                665                 670                 675

CGC GGG TTG GAC ATC CAT ACG AAA ACA GCC ATG GAC ATT TTC CAT GTG      2178
Arg Gly Leu Asp Ile His Thr Lys Thr Ala Met Asp Ile Phe His Val
                680                 685                 690

AGC GAA GAA GAC GTG ACA GCC AAC ATG CGC CGC CAA GCG AAG GCC GTC      2226
Ser Glu Glu Asp Val Thr Ala Asn Met Arg Arg Gln Ala Lys Ala Val
                695                 700                 705
```

-continued

```
AAT TTT GGC ATC GTG TAC GGC ATT AGT GAT TAC GGT CTG GCG CAA AAC      2274
Asn Phe Gly Ile Val Tyr Gly Ile Ser Asp Tyr Gly Leu Ala Gln Asn
    710                 715                 720

TTG AAC ATT ACG CGC AAA GAA GCG GCT GAA TTT ATT GAG CGA TAT TTT      2322
Leu Asn Ile Thr Arg Lys Glu Ala Ala Glu Phe Ile Glu Arg Tyr Phe
725                 730                 735                 740

GCC AGT TTT CCA GGT GTA AAG CAA TAT ATG GAC AAC ATT GTG CAA GAA      2370
Ala Ser Phe Pro Gly Val Lys Gln Tyr Met Asp Asn Ile Val Gln Glu
                745                 750                 755

GCG AAA CAA AAA GGG TAT GTG ACG ACG CTG CTG CAT CGG CGC CGC TAT      2418
Ala Lys Gln Lys Gly Tyr Val Thr Thr Leu Leu His Arg Arg Arg Tyr
            760                 765                 770

TTG CCC GAT ATT ACA AGC CGC AAC TTC AAC GTC CGC AGC TTC GCC GAG      2466
Leu Pro Asp Ile Thr Ser Arg Asn Phe Asn Val Arg Ser Phe Ala Glu
        775                 780                 785

CGG ACG GCG ATG AAC ACA CCG ATC CAA GGG AGT GCC GCT GAT ATT ATT      2514
Arg Thr Ala Met Asn Thr Pro Ile Gln Gly Ser Ala Ala Asp Ile Ile
    790                 795                 800

AAA AAA GCG ATG ATC GAT CTA AGC GTG AGG CTG CGC GAA GAA CGG CTG      2562
Lys Lys Ala Met Ile Asp Leu Ser Val Arg Leu Arg Glu Glu Arg Leu
805                 810                 815                 820

CAG GCG CGC CTG TTG CTG CAA GTG CAT GAC GAA CTC ATT TTG GAG GCG      2610
Gln Ala Arg Leu Leu Leu Gln Val His Asp Glu Leu Ile Leu Glu Ala
                825                 830                 835

CCG AAA GAG GAA ATC GAG CGG CTG TGC CGC CTC GTT CCA GAG GTG ATG      2658
Pro Lys Glu Glu Ile Glu Arg Leu Cys Arg Leu Val Pro Glu Val Met
            840                 845                 850

GAG CAA GCC GTC GCA CTC CGC GTG CCG CTG AAA GTC GAT TAC CAT TAC      2706
Glu Gln Ala Val Ala Leu Arg Val Pro Leu Lys Val Asp Tyr His Tyr
        855                 860                 865

GGT CCG ACG TGG TAC GAC GCC AAA TAAAAGCGGC CTGCCCGCCA GCTGCTCGGT T   2761
Gly Pro Thr Trp Tyr Asp Ala Lys
    870                 875

2761
```

(2) INFORMATION FOR SEQ ID NO:20:

(i) SEQUENCE CHARACTERISTICS:
        (A) LENGTH: 876 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:20:

```
Leu Lys Asn Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Gln Pro Thr His Ile Leu Val Ala Phe Asp Ala Gly Lys Thr Thr
    50                  55                  60
```

-continued

```
Phe Arg His Glu Thr Phe Gln Asp Tyr Lys Gly Gly Arg Gln Gln Thr
 65                  70                  75                  80

Pro Pro Glu Leu Ser Glu Gln Phe Pro Leu Leu Arg Glu Leu Leu Lys
                 85                  90                  95

Ala Tyr Arg Ile Pro Ala Tyr Glu Leu Asp His Tyr Glu Ala Asp Asp
                100                 105                 110

Ile Ile Gly Thr Met Ala Ala Arg Ala Glu Arg Glu Gly Phe Ala Val
                115                 120                 125

Lys Val Ile Ser Gly Asp Arg Asp Leu Thr Gln Leu Ala Ser Pro Gln
130                 135                 140

Val Thr Val Glu Ile Thr Lys Lys Gly Ile Thr Asp Ile Glu Ser Tyr
145                 150                 155                 160

Thr Pro Glu Thr Val Val Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Lys Gln Phe
                195                 200                 205

Gly Thr Val Glu Asn Val Leu Ala Ser Ile Asp Glu Ile Lys Gly Glu
                210                 215                 220

Lys Leu Lys Glu Asn Leu Arg Gln Tyr Arg Asp Leu Ala Leu Leu Ser
225                 230                 235                 240

Lys Gln Leu Ala Ala Ile Cys Arg Asp Ala Pro Val Glu Leu Thr Leu
                245                 250                 255

Asp Asp Ile Val Tyr Lys Gly Glu Asp Arg Glu Lys Val Val Ala Leu
                260                 265                 270

Phe Gln Glu Leu Gly Phe Gln Ser Phe Leu Asp Lys Met Ala Val Gln
                275                 280                 285

Thr Asp Glu Gly Glu Lys Pro Leu Ala Gly Met Asp Phe Ala Ile Ala
290                 295                 300

Asp Ser Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
                340                 345                 350

Ala Asp Pro Lys Phe Leu Ala Trp Leu Gly Asp Glu Thr Lys Lys Lys
                355                 360                 365

Thr Met Phe Asp Ser Lys Arg Ala Ala Val Ala Leu Lys Trp Lys Gly
370                 375                 380

Ile Glu Leu Arg Gly Val Val Phe Asp Leu Leu Leu Ala Ala Tyr Leu
385                 390                 395                 400

Leu Asp Pro Ala Gln Ala Ala Gly Asp Val Ala Ala Val Ala Lys Met
                405                 410                 415

His Gln Tyr Glu Ala Val Arg Ser Asp Glu Ala Val Tyr Gly Lys Gly
                420                 425                 430

Ala Lys Arg Thr Val Pro Asp Glu Pro Thr Leu Ala Glu His Leu Ala
                435                 440                 445

Arg Lys Ala Ala Ala Ile Trp Ala Leu Glu Glu Pro Leu Met Asp Glu
450                 455                 460

Leu Arg Arg Asn Glu Gln Asp Arg Leu Leu Thr Glu Leu Glu Gln Pro
465                 470                 475                 480
```

-continued

```
Leu Ala Gly Ile Leu Ala Asn Met Glu Phe Thr Gly Val Lys Val Asp
                485                 490                 495

Thr Lys Arg Leu Glu Gln Met Gly Ala Glu Leu Thr Glu Gln Leu Gln
            500                 505                 510

Ala Val Glu Arg Arg Ile Tyr Glu Leu Ala Gly Gln Glu Phe Asn Ile
            515                 520                 525

Asn Ser Pro Lys Gln Leu Gly Thr Val Leu Phe Asp Lys Leu Gln Leu
            530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
                565                 570                 575

Tyr Arg Gln Leu Gly Lys Leu Gln Ser Thr Tyr Ile Glu Gly Leu Leu
                580                 585                 590

Lys Val His Pro Val Thr Gly Lys Val His Thr Met Phe Asn Gln
                595                 600                 605

Ala Leu Thr Gln Thr Gly Arg Leu Ser Ser Val Glu Pro Asn Leu Gln
                610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
                660                 665                 670

Glu Ala Phe Arg Arg Gly Leu Asp Ile His Thr Lys Thr Ala Met Asp
                675                 680                 685

Ile Phe His Val Ser Glu Glu Asp Val Thr Ala Asn Met Arg Arg Gln
                690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
                740                 745                 750

Ile Val Gln Glu Ala Lys Gln Lys Gly Tyr Val Thr Thr Leu Leu His
                755                 760                 765

Arg Arg Arg Tyr Leu Pro Asp Ile Thr Ser Arg Asn Phe Asn Val Arg
                770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815

Glu Glu Arg Leu Gln Ala Arg Leu Leu Leu Gln Val His Asp Glu Leu
                820                 825                 830

Ile Leu Glu Ala Pro Lys Glu Glu Ile Glu Arg Leu Cys Arg Leu Val
                835                 840                 845

Pro Glu Val Met Glu Gln Ala Val Ala Leu Arg Val Pro Leu Lys Val
                850                 855                 860

Asp Tyr His Tyr Gly Pro Thr Trp Tyr Asp Ala Lys
865                 870                 875
```

(2) INFORMATION FOR SEQ ID NO:21:

(i) SEQUENCE CHARACTERISTICS:

(A) LENGTH: 2631 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
         (A) NAME/KEY: Coding Sequence
         (B) LOCATION: 1...2628
         (D) OTHER INFORMATION:

(xi) SEQUENCE DESCRIPTION: SEQ ID NO:21:

```
TTG AAA AAC AAG CTC GTC TTA ATT GAC GGC AAC AGC GTG GCG TAC CGC        48
Leu Lys Asn Lys Leu Val Leu Ile Asp Gly Asn Ser Val Ala Tyr Arg
 1               5                  10                  15

GCC TTT TTC GCG TTG CCG CTT TTG CAT AAC GAT AAA GGG ATT CAT ACG        96
Ala Phe Phe Ala Leu Pro Leu Leu His Asn Asp Lys Gly Ile His Thr
                20                  25                  30

AAC GCA GTC TAC GGG TTT ACG ATG ATG TTA AAC AAA ATT TTG GCG GAA       144
Asn Ala Val Tyr Gly Phe Thr Met Met Leu Asn Lys Ile Leu Ala Glu
         35                  40                  45

GAG CAG CCG ACC CAC ATT CTC GTG GCG TTT GAC GCC GGG AAA ACG ACG       192
Glu Gln Pro Thr His Ile Leu Val Ala Phe Asp Ala Gly Lys Thr Thr
 50                  55                  60

TTC CGC CAT GAA ACG TTC CAA GAC TAT AAA GGC GGG CGG CAG CAG ACG       240
Phe Arg His Glu Thr Phe Gln Asp Tyr Lys Gly Gly Arg Gln Gln Thr
 65                  70                  75                  80

CCG CCG GAA CTG TCG GAA CAG TTT CCG CTG CTG CGC GAA TTG CTC AAG       288
Pro Pro Glu Leu Ser Glu Gln Phe Pro Leu Leu Arg Glu Leu Leu Lys
                 85                  90                  95

GCG TAC CGC ATC CCC GCC TAT GAG CTC GAC CAT TAC GAA GCG GAC GAT       336
Ala Tyr Arg Ile Pro Ala Tyr Glu Leu Asp His Tyr Glu Ala Asp Asp
                100                 105                 110

ATT ATC GGA ACG ATG GCG GCG CGG GCT GAG CGA GAA GGG TTT GCA GTG       384
Ile Ile Gly Thr Met Ala Ala Arg Ala Glu Arg Glu Gly Phe Ala Val
        115                 120                 125

AAA GTC ATT TCC GGC GAC CGC GAT TTA ACC CAG CTT GCT TCC CCG CAA       432
Lys Val Ile Ser Gly Asp Arg Asp Leu Thr Gln Leu Ala Ser Pro Gln
130                 135                 140

GTG ACG GTG GAG ATT ACG AAA AAA GGG ATT ACC GAC ATC GAG TCG TAC       480
Val Thr Val Glu Ile Thr Lys Lys Gly Ile Thr Asp Ile Glu Ser Tyr
145                 150                 155                 160

ACG CCG GAG ACG GTC GTG GAA AAA TAC GGC CTC ACC CCG GAG CAA ATT       528
Thr Pro Glu Thr Val Val Glu Lys Tyr Gly Leu Thr Pro Glu Gln Ile
                165                 170                 175

GTC GAC TTG AAA GGA TTG ATG GGC GAC AAA TCC GAC AAC ATC CCT GGC       576
Val Asp Leu Lys Gly Leu Met Gly Asp Lys Ser Asp Asn Ile Pro Gly
                180                 185                 190

GTG CCC GGC ATC GGG GAA AAA ACA GCC GTC AAG CTG CTC AAG CAA TTC       624
Val Pro Gly Ile Gly Glu Lys Thr Ala Val Lys Leu Leu Lys Gln Phe
        195                 200                 205

GGC ACG GTC GAA AAC GTA CTG GCA TCG ATC GAT GAG ATC AAA GGG GAG       672
Gly Thr Val Glu Asn Val Leu Ala Ser Ile Asp Glu Ile Lys Gly Glu
210                 215                 220

AAG CTG AAA GAA AAT TTG CGC CAA TAC CGG GAT TTG GCG CTT TTA AGC       720
```

-continued

```
Lys Leu Lys Glu Asn Leu Arg Gln Tyr Arg Asp Leu Ala Leu Leu Ser
225                 230                 235                 240

AAA CAG CTG GCC GCT ATT TGC CGC GAC GCC CCG GTT GAG CTG ACG CTC       768
Lys Gln Leu Ala Ala Ile Cys Arg Asp Ala Pro Val Glu Leu Thr Leu
                245                 250                 255

GAT GAC ATT GTC TAC AAA GGA GAA GAC CGG GAA AAA GTG GTC GCC TTG       816
Asp Asp Ile Val Tyr Lys Gly Glu Asp Arg Glu Lys Val Val Ala Leu
                260                 265                 270

TTT CAG GAG CTC GGA TTC CAG TCG TTT CTC GAC AAG ATG GCC GTC CAA       864
Phe Gln Glu Leu Gly Phe Gln Ser Phe Leu Asp Lys Met Ala Val Gln
            275                 280                 285

ACG GAT GAA GGC GAA AAG CCG CTC GCC GGG ATG GAT TTT GCG ATC GCC       912
Thr Asp Glu Gly Glu Lys Pro Leu Ala Gly Met Asp Phe Ala Ile Ala
290                 295                 300

GAC AGC GTC ACG GAC GAA ATG CTC GCC GAC AAA GCG GCC CTC GTC GTG       960
Asp Ser Val Thr Asp Glu Met Leu Ala Asp Lys Ala Ala Leu Val Val
305                 310                 315                 320

GAG GTG GTG GGC GAC AAC TAT CAC CAT GCC CCG ATT GTC GGG ATC GCC      1008
Glu Val Val Gly Asp Asn Tyr His His Ala Pro Ile Val Gly Ile Ala
                325                 330                 335

TTG GCC AAC GAA CGC GGG CGG TTT TTC CTG CGC CCG GAG ACG GCG CTC      1056
Leu Ala Asn Glu Arg Gly Arg Phe Phe Leu Arg Pro Glu Thr Ala Leu
                340                 345                 350

GCC GAT CCG AAA TTT CTC GCT TGG CTT GGC GAT GAG ACG AAG AAA AAA      1104
Ala Asp Pro Lys Phe Leu Ala Trp Leu Gly Asp Glu Thr Lys Lys Lys
            355                 360                 365

ACG ATG TTT GAT TCA AAG CGG GCG GCC GTC GCG CTA AAA TGG AAA GGA      1152
Thr Met Phe Asp Ser Lys Arg Ala Ala Val Ala Leu Lys Trp Lys Gly
370                 375                 380

ATC GAA CTG CGC GGC GTC GTG TTC GAT CTG TTG CTG GCC GCT TAC TTG      1200
Ile Glu Leu Arg Gly Val Val Phe Asp Leu Leu Leu Ala Ala Tyr Leu
385                 390                 395                 400

CTC GAT CCG GCG CAG GCG GCG GGC GAC GTT GCC GCG GTG GCG AAA ATG      1248
Leu Asp Pro Ala Gln Ala Ala Gly Asp Val Ala Ala Val Ala Lys Met
                405                 410                 415

CAT CAG TAC GAG GCG GTG CGA TCG GAT GAG GCG GTC TAT GGA AAA GGA      1296
His Gln Tyr Glu Ala Val Arg Ser Asp Glu Ala Val Tyr Gly Lys Gly
                420                 425                 430

GCG AAG CGG ACG GTT CCT GAT GAA CCG ACG CTT GCC GAG CAT CTC GCC      1344
Ala Lys Arg Thr Val Pro Asp Glu Pro Thr Leu Ala Glu His Leu Ala
            435                 440                 445

CGC AAG GCG GCG GCC ATT TGG GCG CTT GAA GAG CCG TTG ATG GAC GAA      1392
Arg Lys Ala Ala Ala Ile Trp Ala Leu Glu Glu Pro Leu Met Asp Glu
450                 455                 460

CTG CGC CGC AAC GAA CAA GAT CGG CTG CTG ACC GAG CTC GAA CAG CCG      1440
Leu Arg Arg Asn Glu Gln Asp Arg Leu Leu Thr Glu Leu Glu Gln Pro
465                 470                 475                 480

CTG GCT GGC ATT TTG GCC AAT ATG GAA TTT ACT GGA GTG AAA GTG GAC      1488
Leu Ala Gly Ile Leu Ala Asn Met Glu Phe Thr Gly Val Lys Val Asp
                485                 490                 495

ACG AAG CGG CTT GAA CAG ATG GGG GCG GAG CTC ACC GAG CAG CTG CAG      1536
Thr Lys Arg Leu Glu Gln Met Gly Ala Glu Leu Thr Glu Gln Leu Gln
                500                 505                 510

GCG GTC GAG CGG CGC ATT TAC GAA CTC GCC GGC CAA GAG TTC AAC ATT      1584
Ala Val Glu Arg Arg Ile Tyr Glu Leu Ala Gly Gln Glu Phe Asn Ile
                515                 520                 525

AAC TCG CCG AAA CAG CTC GGG ACG GTT TTA TTT GAC AAG CTG CAG CTC      1632
Asn Ser Pro Lys Gln Leu Gly Thr Val Leu Phe Asp Lys Leu Gln Leu
530                 535                 540
```

-continued

```
CCG GTG TTG AAA AAG ACA AAA ACC GGC TAT TCG ACT TCA GCC GAT GTG    1680
Pro Val Leu Lys Lys Thr Lys Thr Gly Tyr Ser Thr Ser Ala Asp Val
545                 550                 555                 560

CTT GAG AAG CTT GCA CCG CAC CAT GAA ATC GTC GAA CAT ATT TTG CAT    1728
Leu Glu Lys Leu Ala Pro His His Glu Ile Val Glu His Ile Leu His
                565                 570                 575

TAC CGC CAA CTC GGC AAG CTG CAG TCA ACG TAT ATT GAA GGG CTG CTG    1776
Tyr Arg Gln Leu Gly Lys Leu Gln Ser Thr Tyr Ile Glu Gly Leu Leu
            580                 585                 590

AAA GTG GTG CAC CCC GTG ACG GGC AAA GTG CAC ACG ATG TTC AAT CAG    1824
Lys Val Val His Pro Val Thr Gly Lys Val His Thr Met Phe Asn Gln
        595                 600                 605

GCG TTG ACG CAA ACC GGG CGC CTC AGC TCC GTC GAA CCG AAT TTG CAA    1872
Ala Leu Thr Gln Thr Gly Arg Leu Ser Ser Val Glu Pro Asn Leu Gln
    610                 615                 620

AAC ATT CCG ATT CGG CTT GAG GAA GGG CGG AAA ATC CGC CAG GCG TTC    1920
Asn Ile Pro Ile Arg Leu Glu Glu Gly Arg Lys Ile Arg Gln Ala Phe
625                 630                 635                 640

GTG CCG TCG GAG CCG GAC TGG CTC ATC TTT GCG GCC GAC TAT TCG CAA    1968
Val Pro Ser Glu Pro Asp Trp Leu Ile Phe Ala Ala Asp Tyr Ser Gln
                645                 650                 655

ATC GAG CTG CGC GTC CTC GCC CAT ATC GCG GAA GAT GAC AAT TTG ATT    2016
Ile Glu Leu Arg Val Leu Ala His Ile Ala Glu Asp Asp Asn Leu Ile
            660                 665                 670

GAA GCG TTC CGG CGC GGG TTG GAC ATC CAT ACG AAA ACA GCC ATG GAC    2064
Glu Ala Phe Arg Arg Gly Leu Asp Ile His Thr Lys Thr Ala Met Asp
        675                 680                 685

ATT TTC CAT GTG AGC GAA GAA GAC GTG ACA GCC AAC ATG CGC CGC CAA    2112
Ile Phe His Val Ser Glu Glu Asp Val Thr Ala Asn Met Arg Arg Gln
    690                 695                 700

GCG AAG GCC GTC AAT TTT GGC ATC GTG TAC GGC ATT AGT GAT TAC GGT    2160
Ala Lys Ala Val Asn Phe Gly Ile Val Tyr Gly Ile Ser Asp Tyr Gly
705                 710                 715                 720

CTG GCG CAA AAC TTG AAC ATT ACG CGC AAA GAA GCG GCT GAA TTT ATT    2208
Leu Ala Gln Asn Leu Asn Ile Thr Arg Lys Glu Ala Ala Glu Phe Ile
                725                 730                 735

GAG CGA TAT TTT GCC AGT TTT CCA GGT GTA AAG CAA TAT ATG GAC AAC    2256
Glu Arg Tyr Phe Ala Ser Phe Pro Gly Val Lys Gln Tyr Met Asp Asn
            740                 745                 750

ATT GTG CAA GAA GCG AAA CAA AAA GGG TAT GTG ACG ACG CTG CTG CAT    2304
Ile Val Gln Glu Ala Lys Gln Lys Gly Tyr Val Thr Thr Leu Leu His
        755                 760                 765

CGG CGC CGC TAT TTG CCC GAT ATT ACA AGC CGC AAC TTC AAC GTC CGC    2352
Arg Arg Arg Tyr Leu Pro Asp Ile Thr Ser Arg Asn Phe Asn Val Arg
    770                 775                 780

AGC TTC GCC GAG CGG ACG GCG ATG AAC ACA CCG ATC CAA GGG AGT GCC    2400
Ser Phe Ala Glu Arg Thr Ala Met Asn Thr Pro Ile Gln Gly Ser Ala
785                 790                 795                 800

GCT GAT ATT ATT AAA AAA GCG ATG ATC GAT CTA AGC GTG AGG CTG CGC    2448
Ala Asp Ile Ile Lys Lys Ala Met Ile Asp Leu Ser Val Arg Leu Arg
                805                 810                 815

GAA GAA CGG CTG CAG GCG CGC CTG TTG CTG CAA GTG CAT GAC GAA CTC    2496
Glu Glu Arg Leu Gln Ala Arg Leu Leu Leu Gln Val His Asp Glu Leu
            820                 825                 830

ATT TTG GAG GCG CCG AAA GAG GAA ATC GAG CGG CTG TGC CGC CTC GTT    2544
Ile Leu Glu Ala Pro Lys Glu Glu Ile Glu Arg Leu Cys Arg Leu Val
        835                 840                 845

CCA GAG GTG ATG GAG CAA GCC GTC GCA CTC CGC GTG CCG CTG AAA GTC    2592
Pro Glu Val Met Glu Gln Ala Val Ala Leu Arg Val Pro Leu Lys Val
    850                 855                 860
```

```
GAT TAC CAT TAC GGT CCG ACG TGG TAC GAC GCC AAA TAA                 2631
Asp Tyr His Tyr Gly Pro Thr Trp Tyr Asp Ala Lys
865                 870                 875

(2) INFORMATION FOR SEQ ID NO:22:

(i) SEQUENCE CHARACTERISTICS:
        (A) LENGTH: 1764 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...1761
        (D) OTHER INFORMATION:

(xi) SEQUENCE DESCRIPTION: SEQ ID NO:22:

GAT GAA GGC GAA AAG CCG CTC GCC GGG ATG GAT TTT GCG ATC GCC GAC       48
Asp Glu Gly Glu Lys Pro Leu Ala Gly Met Asp Phe Ala Ile Ala Asp
1               5                   10                  15

AGC GTC ACG GAC GAA ATG CTC GCC GAC AAA GCG GCC CTC GTC GTG GAG       96
Ser Val Thr Asp Glu Met Leu Ala Asp Lys Ala Ala Leu Val Val Glu
            20                  25                  30

GTG GTG GGC GAC AAC TAT CAC CAT GCC CCG ATT GTC GGG ATC GCC TTG      144
Val Val Gly Asp Asn Tyr His His Ala Pro Ile Val Gly Ile Ala Leu
        35                  40                  45

GCC AAC GAA CGC GGG CGG TTT TTC CTG CGC CCG GAG ACG GCG CTC GCC      192
Ala Asn Glu Arg Gly Arg Phe Phe Leu Arg Pro Glu Thr Ala Leu Ala
    50                  55                  60

GAT CCG AAA TTT CTC GCT TGG CTT GGC GAT GAG ACG AAG AAA AAA ACG      240
Asp Pro Lys Phe Leu Ala Trp Leu Gly Asp Glu Thr Lys Lys Lys Thr
65                  70                  75                  80

ATG TTT GAT TCA AAG CGG GCG GCC GTC GCG CTA AAA TGG AAA GGA ATC      288
Met Phe Asp Ser Lys Arg Ala Ala Val Ala Leu Lys Trp Lys Gly Ile
                85                  90                  95

GAA CTG CGC GGC GTC GTG TTC GAT CTG TTG CTG GCC GCT TAC TTG CTC      336
Glu Leu Arg Gly Val Val Phe Asp Leu Leu Leu Ala Ala Tyr Leu Leu
            100                 105                 110

GAT CCG GCG CAG GCG GCG GGC GAC GTT GCC GCG GTG GCG AAA ATG CAT      384
Asp Pro Ala Gln Ala Ala Gly Asp Val Ala Ala Val Ala Lys Met His
        115                 120                 125

CAG TAC GAG GCG GTG CGA TCG GAT GAG GCG GTC TAT GGA AAA GGA GCG      432
Gln Tyr Glu Ala Val Arg Ser Asp Glu Ala Val Tyr Gly Lys Gly Ala
    130                 135                 140

AAG CGG ACG GTT CCT GAT GAA CCG ACG CTT GCC GAG CAT CTC GCC CGC      480
Lys Arg Thr Val Pro Asp Glu Pro Thr Leu Ala Glu His Leu Ala Arg
145                 150                 155                 160

AAG GCG GCG GCC ATT TGG GCG CTT GAA GAG CCG TTG ATG GAC GAA CTG      528
Lys Ala Ala Ala Ile Trp Ala Leu Glu Glu Pro Leu Met Asp Glu Leu
                165                 170                 175

CGC CGC AAC GAA CAA GAT CGG CTG CTG ACC GAG CTC GAA CAG CCG CTG      576
Arg Arg Asn Glu Gln Asp Arg Leu Leu Thr Glu Leu Glu Gln Pro Leu
            180                 185                 190
```

```
GCT GGC ATT TTG GCC AAT ATG GAA TTT ACT GGA GTG AAA GTG GAC ACG      624
Ala Gly Ile Leu Ala Asn Met Glu Phe Thr Gly Val Lys Val Asp Thr
        195                 200                 205

AAG CGG CTT GAA CAG ATG GGG GCG GAG CTC ACC GAG CAG CTG CAG GCG      672
Lys Arg Leu Glu Gln Met Gly Ala Glu Leu Thr Glu Gln Leu Gln Ala
210                 215                 220

GTC GAG CGG CGC ATT TAC GAA CTC GCC GGC CAA GAG TTC AAC ATT AAC      720
Val Glu Arg Arg Ile Tyr Glu Leu Ala Gly Gln Glu Phe Asn Ile Asn
225                 230                 235                 240

TCG CCG AAA CAG CTC GGG ACG GTT TTA TTT GAC AAG CTG CAG CTC CCG      768
Ser Pro Lys Gln Leu Gly Thr Val Leu Phe Asp Lys Leu Gln Leu Pro
            245                 250                 255

GTG TTG AAA AAG ACA AAA ACC GGC TAT TCG ACT TCA GCC GAT GTG CTT      816
Val Leu Lys Lys Thr Lys Thr Gly Tyr Ser Thr Ser Ala Asp Val Leu
                260                 265                 270

GAG AAG CTT GCA CCG CAC CAT GAA ATC GTC GAA CAT ATT TTG CAT TAC      864
Glu Lys Leu Ala Pro His His Glu Ile Val Glu His Ile Leu His Tyr
                    275                 280                 285

CGC CAA CTC GGC AAG CTG CAG TCA ACG TAT ATT GAA GGG CTG CTG AAA      912
Arg Gln Leu Gly Lys Leu Gln Ser Thr Tyr Ile Glu Gly Leu Leu Lys
        290                 295                 300

GTG GTG CAC CCC GTG ACG GGC AAA GTG CAC ACG ATG TTC AAT CAG GCG      960
Val Val His Pro Val Thr Gly Lys Val His Thr Met Phe Asn Gln Ala
305                 310                 315                 320

TTG ACG CAA ACC GGG CGC CTC AGC TCC GTC GAA CCG AAT TTG CAA AAC     1008
Leu Thr Gln Thr Gly Arg Leu Ser Ser Val Glu Pro Asn Leu Gln Asn
            325                 330                 335

ATT CCG ATT CGG CTT GAG GAA GGG CGG AAA ATC CGC CAG GCG TTC GTG     1056
Ile Pro Ile Arg Leu Glu Glu Gly Arg Lys Ile Arg Gln Ala Phe Val
                340                 345                 350

CCG TCG GAG CCG GAC TGG CTC ATC TTT GCG GCC GAC TAT TCG CAA ATC     1104
Pro Ser Glu Pro Asp Trp Leu Ile Phe Ala Ala Asp Tyr Ser Gln Ile
                    355                 360                 365

GAG CTG CGC GTC CTC GCC CAT ATC GCG GAA GAT GAC AAT TTG ATT GAA     1152
Glu Leu Arg Val Leu Ala His Ile Ala Glu Asp Asp Asn Leu Ile Glu
        370                 375                 380

GCG TTC CGG CGC GGG TTG GAC ATC CAT ACG AAA ACA GCC ATG GAC ATT     1200
Ala Phe Arg Arg Gly Leu Asp Ile His Thr Lys Thr Ala Met Asp Ile
385                 390                 395                 400

TTC CAT GTG AGC GAA GAA GAC GTG ACA GCC AAC ATG CGC CGC CAA GCG     1248
Phe His Val Ser Glu Glu Asp Val Thr Ala Asn Met Arg Arg Gln Ala
            405                 410                 415

AAG GCC GTC AAT TTT GGC ATC GTG TAC GGC ATT AGT GAT TAC GGT CTG     1296
Lys Ala Val Asn Phe Gly Ile Val Tyr Gly Ile Ser Asp Tyr Gly Leu
                420                 425                 430

GCG CAA AAC TTG AAC ATT ACG CGC AAA GAA GCG GCT GAA TTT ATT GAG     1344
Ala Gln Asn Leu Asn Ile Thr Arg Lys Glu Ala Ala Glu Phe Ile Glu
                    435                 440                 445

CGA TAT TTT GCC AGT TTT CCA GGT GTA AAG CAA TAT ATG GAC AAC ATT     1392
Arg Tyr Phe Ala Ser Phe Pro Gly Val Lys Gln Tyr Met Asp Asn Ile
        450                 455                 460

GTG CAA GAA GCG AAA CAA AAA GGG TAT GTG ACG ACG CTG CTG CAT CGG     1440
Val Gln Glu Ala Lys Gln Lys Gly Tyr Val Thr Thr Leu Leu His Arg
465                 470                 475                 480

CGC CGC TAT TTG CCC GAT ATT ACA AGC CGC AAC TTC AAC GTC CGC AGC     1488
Arg Arg Tyr Leu Pro Asp Ile Thr Ser Arg Asn Phe Asn Val Arg Ser
            485                 490                 495

TTC GCC GAG CGG ACG GCG ATG AAC ACA CCG ATC CAA GGG AGT GCC GCT     1536
Phe Ala Glu Arg Thr Ala Met Asn Thr Pro Ile Gln Gly Ser Ala Ala
                500                 505                 510
```

-continued

```
GAT ATT ATT AAA AAA GCG ATG ATC GAT CTA AGC GTG AGG CTG CGC GAA    1584
Asp Ile Ile Lys Lys Ala Met Ile Asp Leu Ser Val Arg Leu Arg Glu
        515                 520                 525

GAA CGG CTG CAG GCG CGC CTG TTG CTG CAA GTG CAT GAC GAA CTC ATT    1632
Glu Arg Leu Gln Ala Arg Leu Leu Leu Gln Val His Asp Glu Leu Ile
    530                 535                 540

TTG GAG GCG CCG AAA GAG GAA ATC GAG CGG CTG TGC CGC CTC GTT CCA    1680
Leu Glu Ala Pro Lys Glu Glu Ile Glu Arg Leu Cys Arg Leu Val Pro
545                 550                 555                 560

GAG GTG ATG GAG CAA GCC GTC GCA CTC CGC GTG CCG CTG AAA GTC GAT    1728
Glu Val Met Glu Gln Ala Val Ala Leu Arg Val Pro Leu Lys Val Asp
                565                 570                 575

TAC CAT TAC GGT CCG ACG TGG TAC GAC GCC AAA TAA                    1764
Tyr His Tyr Gly Pro Thr Trp Tyr Asp Ala Lys
            580                 585
```

(2) INFORMATION FOR SEQ ID NO:23:

(i) SEQUENCE CHARACTERISTICS:
        (A) LENGTH: 587 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:23:

```
Asp Glu Gly Glu Lys Pro Leu Ala Gly Met Asp Phe Ala Ile Ala Asp
1               5                   10                  15

Ser Val Thr Asp Glu Met Leu Ala Asp Lys Ala Ala Leu Val Val Glu
            20                  25                  30

Val Val Gly Asp Asn Tyr His His Ala Pro Ile Val Gly Ile Ala Leu
        35                  40                  45

Ala Asn Glu Arg Gly Arg Phe Phe Leu Arg Pro Glu Thr Ala Leu Ala
    50                  55                  60

Asp Pro Lys Phe Leu Ala Trp Leu Gly Asp Glu Thr Lys Lys Lys Thr
65                  70                  75                  80

Met Phe Asp Ser Lys Arg Ala Ala Val Ala Leu Lys Trp Lys Gly Ile
                85                  90                  95

Glu Leu Arg Gly Val Val Phe Asp Leu Leu Leu Ala Ala Tyr Leu Leu
            100                 105                 110

Asp Pro Ala Gln Ala Ala Gly Asp Val Ala Ala Val Ala Lys Met His
        115                 120                 125

Gln Tyr Glu Ala Val Arg Ser Asp Glu Ala Val Tyr Gly Lys Gly Ala
    130                 135                 140

Lys Arg Thr Val Pro Asp Glu Pro Thr Leu Ala Glu His Leu Ala Arg
145                 150                 155                 160

Lys Ala Ala Ile Trp Ala Leu Glu Pro Leu Met Asp Glu Leu
                165                 170                 175

Arg Arg Asn Glu Gln Asp Arg Leu Leu Thr Glu Leu Glu Gln Pro Leu
            180                 185                 190

Ala Gly Ile Leu Ala Asn Met Glu Phe Thr Gly Val Lys Val Asp Thr
```

```
              195                 200                 205
Lys Arg Leu Glu Gln Met Gly Ala Glu Leu Thr Glu Gln Leu Gln Ala
    210                 215                 220
Val Glu Arg Arg Ile Tyr Glu Leu Ala Gly Gln Glu Phe Asn Ile Asn
225                 230                 235                 240
Ser Pro Lys Gln Leu Gly Thr Val Leu Phe Asp Lys Leu Gln Leu Pro
                245                 250                 255
Val Leu Lys Lys Thr Lys Thr Gly Tyr Ser Thr Ser Ala Asp Val Leu
            260                 265                 270
Glu Lys Leu Ala Pro His His Glu Ile Val Glu His Ile Leu His Tyr
        275                 280                 285
Arg Gln Leu Gly Lys Leu Gln Ser Thr Tyr Ile Glu Gly Leu Leu Lys
    290                 295                 300
Val Val His Pro Val Thr Gly Lys Val His Thr Met Phe Asn Gln Ala
305                 310                 315                 320
Leu Thr Gln Thr Gly Arg Leu Ser Ser Val Glu Pro Asn Leu Gln Asn
                325                 330                 335
Ile Pro Ile Arg Leu Glu Glu Gly Arg Lys Ile Arg Gln Ala Phe Val
                340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Glu Asp Asn Leu Ile Glu
370                 375                 380
Ala Phe Arg Arg Gly Leu Asp Ile His Thr Lys Thr Ala Met Asp Ile
385                 390                 395                 400
Phe His Val Ser Glu Glu Asp Val Thr Ala Asn Met Arg Arg Gln Ala
                405                 410                 415
Lys Ala Val Asn Phe Gly Ile Val Tyr Gly Ile Ser Asp Tyr Gly Leu
                420                 425                 430
Ala Gln Asn Leu Asn Ile Thr Arg Lys Glu Ala Ala Glu Phe Ile Glu
                435                 440                 445
Arg Tyr Phe Ala Ser Phe Pro Gly Val Lys Gln Tyr Met Asp Asn Ile
    450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
                485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Leu Ser Val Arg Leu Arg Glu
        515                 520                 525
Glu Arg Leu Gln Ala Arg Leu Leu Leu Gln Val His Asp Glu Leu Ile
    530                 535                 540
Leu Glu Ala Pro Lys Glu Glu Ile Glu Arg Leu Cys Arg Leu Val Pro
545                 550                 555                 560
Glu Val Met Glu Gln Ala Val Ala Leu Arg Val Pro Leu Lys Val Asp
                565                 570                 575
Tyr His Tyr Gly Pro Thr Trp Tyr Asp Ala Lys
            580                 585
```

(2) INFORMATION FOR SEQ ID NO:24:

(i) SEQUENCE CHARACTERISTICS:
        (A) LENGTH: 1767 base pairs

```
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: Coding Sequence
            (B) LOCATION: 1...1764
            (D) OTHER INFORMATION:

(xi) SEQUENCE DESCRIPTION: SEQ ID NO:24:

ACG GAT GAA GGC GAA AAG CCG CTC GCC GGG ATG GAT TTT GCG ATC GCC       48
Thr Asp Glu Gly Glu Lys Pro Leu Ala Gly Met Asp Phe Ala Ile Ala
 1               5                  10                  15

GAC AGC GTC ACG GAC GAA ATG CTC GCC GAC AAA GCG GCC CTC GTC GTG       96
Asp Ser Val Thr Asp Glu Met Leu Ala Asp Lys Ala Ala Leu Val Val
                 20                  25                  30

GAG GTG GTG GGC GAC AAC TAT CAC CAT GCC CCG ATT GTC GGG ATC GCC      144
Glu Val Val Gly Asp Asn Tyr His His Ala Pro Ile Val Gly Ile Ala
             35                  40                  45

TTG GCC AAC GAA CGC GGG CGG TTT TTC CTG CGC CCG GAG ACG GCG CTC      192
Leu Ala Asn Glu Arg Gly Arg Phe Phe Leu Arg Pro Glu Thr Ala Leu
 50                  55                  60

GCC GAT CCG AAA TTT CTC GCT TGG CTT GGC GAT GAG ACG AAG AAA AAA      240
Ala Asp Pro Lys Phe Leu Ala Trp Leu Gly Asp Glu Thr Lys Lys Lys
65                  70                  75                  80

ACG ATG TTT GAT TCA AAG CGG GCG GCC GTC GCG CTA AAA TGG AAA GGA      288
Thr Met Phe Asp Ser Lys Arg Ala Ala Val Ala Leu Lys Trp Lys Gly
                 85                  90                  95

ATC GAA CTG CGC GGC GTC GTG TTC GAT CTG TTG CTG GCC GCT TAC TTG      336
Ile Glu Leu Arg Gly Val Val Phe Asp Leu Leu Leu Ala Ala Tyr Leu
            100                 105                 110

CTC GAT CCG GCG CAG GCG GCG GGC GAC GTT GCC GCG GTG GCG AAA ATG      384
Leu Asp Pro Ala Gln Ala Ala Gly Asp Val Ala Ala Val Ala Lys Met
            115                 120                 125

CAT CAG TAC GAG GCG GTG CGA TCG GAT GAG GCG GTC TAT GGA AAA GGA      432
His Gln Tyr Glu Ala Val Arg Ser Asp Glu Ala Val Tyr Gly Lys Gly
130                 135                 140

GCG AAG CGG ACG GTT CCT GAT GAA CCG ACG CTT GCC GAG CAT CTC GCC      480
Ala Lys Arg Thr Val Pro Asp Glu Pro Thr Leu Ala Glu His Leu Ala
145                 150                 155                 160

CGC AAG GCG GCG GCC ATT TGG GCG CTT GAA GAG CCG TTG ATG GAC GAA      528
Arg Lys Ala Ala Ala Ile Trp Ala Leu Glu Glu Pro Leu Met Asp Glu
                165                 170                 175

CTG CGC CGC AAC GAA CAA GAT CGG CTG CTG ACC GAG CTC GAA CAG CCG      576
Leu Arg Arg Asn Glu Gln Asp Arg Leu Leu Thr Glu Leu Glu Gln Pro
            180                 185                 190

CTG GCT GGC ATT TTG GCC AAT ATG GAA TTT ACT GGA GTG AAA GTG GAC      624
Leu Ala Gly Ile Leu Ala Asn Met Glu Phe Thr Gly Val Lys Val Asp
            195                 200                 205

ACG AAG CGG CTT GAA CAG ATG GGG GCG GAG CTC ACC GAG CAG CTG CAG      672
Thr Lys Arg Leu Glu Gln Met Gly Ala Glu Leu Thr Glu Gln Leu Gln
        210                 215                 220

GCG GTC GAG CGG CGC ATT TAC GAA CTC GCC GGC CAA GAG TTC AAC ATT      720
Ala Val Glu Arg Arg Ile Tyr Glu Leu Ala Gly Gln Glu Phe Asn Ile
```

```
                225                  230                  235                  240
AAC TCG CCG AAA CAG CTC GGG ACG GTT TTA TTT GAC AAG CTG CAG CTC              768
Asn Ser Pro Lys Gln Leu Gly Thr Val Leu Phe Asp Lys Leu Gln Leu
                245                  250                  255

CCG GTG TTG AAA AAG ACA AAA ACC GGC TAT TCG ACT TCA GCC GAT GTG              816
Pro Val Leu Lys Lys Thr Lys Thr Gly Tyr Ser Thr Ser Ala Asp Val
                260                  265                  270

CTT GAG AAG CTT GCA CCG CAC CAT GAA ATC GTC GAA CAT ATT TTG CAT              864
Leu Glu Lys Leu Ala Pro His His Glu Ile Val Glu His Ile Leu His
                275                  280                  285

TAC CGC CAA CTC GGC AAG CTG CAG TCA ACG TAT ATT GAA GGG CTG CTG              912
Tyr Arg Gln Leu Gly Lys Leu Gln Ser Thr Tyr Ile Glu Gly Leu Leu
                290                  295                  300

AAA GTG GTG CAC CCC GTG ACG GGC AAA GTG CAC ACG ATG TTC AAT CAG              960
Lys Val Val His Pro Val Thr Gly Lys Val His Thr Met Phe Asn Gln
305                  310                  315                  320

GCG TTG ACG CAA ACC GGG CGC CTC AGC TCC GTC GAA CCG AAT TTG CAA             1008
Ala Leu Thr Gln Thr Gly Arg Leu Ser Ser Val Glu Pro Asn Leu Gln
                325                  330                  335

AAC ATT CCG ATT CGG CTT GAG GAA GGG CGG AAA ATC CGC CAG GCG TTC             1056
Asn Ile Pro Ile Arg Leu Glu Glu Gly Arg Lys Ile Arg Gln Ala Phe
                340                  345                  350

GTG CCG TCG GAG CCG GAC TGG CTC ATC TTT GCG GCC GAC TAT TCG CAA             1104
Val Pro Ser Glu Pro Asp Trp Leu Ile Phe Ala Ala Asp Tyr Ser Gln
                355                  360                  365

ATC GAG CTG CGC GTC CTC GCC CAT ATC GCG GAA GAT GAC AAT TTG ATT             1152
Ile Glu Leu Arg Val Leu Ala His Ile Ala Glu Asp Asp Asn Leu Ile
                370                  375                  380

GAA GCG TTC CGG CGC GGG TTG GAC ATC CAT ACG AAA ACA GCC ATG GAC             1200
Glu Ala Phe Arg Arg Gly Leu Asp Ile His Thr Lys Thr Ala Met Asp
385                  390                  395                  400

ATT TTC CAT GTG AGC GAA GAA GAC GTG ACA GCC AAC ATG CGC CGC CAA             1248
Ile Phe His Val Ser Glu Glu Asp Val Thr Ala Asn Met Arg Arg Gln
                405                  410                  415

GCG AAG GCC GTC AAT TTT GGC ATC GTG TAC GGC ATT AGT GAT TAC GGT             1296
Ala Lys Ala Val Asn Phe Gly Ile Val Tyr Gly Ile Ser Asp Tyr Gly
                420                  425                  430

CTG GCG CAA AAC TTG AAC ATT ACG CGC AAA GAA GCG GCT GAA TTT ATT             1344
Leu Ala Gln Asn Leu Asn Ile Thr Arg Lys Glu Ala Ala Glu Phe Ile
                435                  440                  445

GAG CGA TAT TTT GCC AGT TTT CCA GGT GTA AAG CAA TAT ATG GAC AAC             1392
Glu Arg Tyr Phe Ala Ser Phe Pro Gly Val Lys Gln Tyr Met Asp Asn
                450                  455                  460

ATT GTG CAA GAA GCG AAA CAA AAA GGG TAT GTG ACG ACG CTG CTG CAT             1440
Ile Val Gln Glu Ala Lys Gln Lys Gly Tyr Val Thr Thr Leu Leu His
465                  470                  475                  480

CGG CGC CGC TAT TTG CCC GAT ATT ACA AGC CGC AAC TTC AAC GTC CGC             1488
Arg Arg Arg Tyr Leu Pro Asp Ile Thr Ser Arg Asn Phe Asn Val Arg
                485                  490                  495

AGC TTC GCC GAG CGG ACG GCG ATG AAC ACA CCG ATC CAA GGG AGT GCC             1536
Ser Phe Ala Glu Arg Thr Ala Met Asn Thr Pro Ile Gln Gly Ser Ala
                500                  505                  510

GCT GAT ATT ATT AAA AAA GCG ATG ATC GAT CTA AGC GTG AGG CTG CGC             1584
Ala Asp Ile Ile Lys Lys Ala Met Ile Asp Leu Ser Val Arg Leu Arg
                515                  520                  525

GAA GAA CGG CTG CAG GCG CGC CTG TTG CTG CAA GTG CAT GAC GAA CTC             1632
Glu Glu Arg Leu Gln Ala Arg Leu Leu Leu Gln Val His Asp Glu Leu
                530                  535                  540

ATT TTG GAG GCG CCG AAA GAG GAA ATC GAG CGG CTG TGC CGC CTC GTT             1680
```

```
Ile Leu Glu Ala Pro Lys Glu Glu Ile Glu Arg Leu Cys Arg Leu Val
545                 550                 555                 560

CCA GAG GTG ATG GAG CAA GCC GTC GCA CTC CGC GTG CCG CTG AAA GTC      1728
Pro Glu Val Met Glu Gln Ala Val Ala Leu Arg Val Pro Leu Lys Val
                565                 570                 575

GAT TAC CAT TAC GGT CCG ACG TGG TAC GAC GCC AAA TAA                  1767
Asp Tyr His Tyr Gly Pro Thr Trp Tyr Asp Ala Lys
            580                 585
```

(2) INFORMATION FOR SEQ ID NO:25:

(i) SEQUENCE CHARACTERISTICS:
        (A) LENGTH: 588 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

```
Thr Asp Glu Gly Glu Lys Pro Leu Ala Gly Met Asp Phe Ala Ile Ala
1               5                   10                  15

Asp Ser Val Thr Asp Glu Met Leu Ala Asp Lys Ala Ala Leu Val Val
                20                  25                  30

Glu Val Val Gly Asp Asn Tyr His His Ala Pro Ile Val Gly Ile Ala
            35                  40                  45

Leu Ala Asn Glu Arg Gly Arg Phe Phe Leu Arg Pro Glu Thr Ala Leu
        50                  55                  60

Ala Asp Pro Lys Phe Leu Ala Trp Leu Gly Asp Glu Thr Lys Lys Lys
65                  70                  75                  80

Thr Met Phe Asp Ser Lys Arg Ala Ala Val Ala Leu Lys Trp Lys Gly
                85                  90                  95

Ile Glu Leu Arg Gly Val Val Phe Asp Leu Leu Ala Ala Tyr Leu
            100                 105                 110

Leu Asp Pro Ala Gln Ala Ala Gly Asp Val Ala Ala Val Ala Lys Met
        115                 120                 125

His Gln Tyr Glu Ala Val Arg Ser Asp Glu Ala Val Tyr Gly Lys Gly
    130                 135                 140

Ala Lys Arg Thr Val Pro Asp Glu Pro Thr Leu Ala Glu His Leu Ala
145                 150                 155                 160

Arg Lys Ala Ala Ala Ile Trp Ala Leu Glu Glu Pro Leu Met Asp Glu
                165                 170                 175

Leu Arg Arg Asn Glu Gln Asp Arg Leu Leu Thr Glu Leu Glu Gln Pro
            180                 185                 190

Leu Ala Gly Ile Leu Ala Asn Met Glu Phe Thr Gly Val Lys Val Asp
        195                 200                 205

Thr Lys Arg Leu Glu Gln Met Gly Ala Glu Leu Thr Glu Gln Leu Gln
    210                 215                 220

Ala Val Glu Arg Arg Ile Tyr Glu Leu Ala Gly Gln Glu Phe Asn Ile
225                 230                 235                 240

Asn Ser Pro Lys Gln Leu Gly Thr Val Leu Phe Asp Lys Leu Gln Leu
                245                 250                 255
```

```
Pro Val Leu Lys Lys Thr Lys Thr Gly Tyr Ser Thr Ser Ala Asp Val
        260                 265                 270

Leu Glu Lys Leu Ala Pro His His Glu Ile Val Glu His Ile Leu His
        275                 280                 285

Tyr Arg Gln Leu Gly Lys Leu Gln Ser Thr Tyr Ile Glu Gly Leu Leu
        290                 295                 300

Lys Val Val His Pro Val Thr Gly Lys Val His Thr Met Phe Asn Gln
305                 310                 315                 320

Ala Leu Thr Gln Thr Gly Arg Leu Ser Ser Val Glu Pro Asn Leu Gln
            325                 330                 335

Asn Ile Pro Ile Arg Leu Glu Glu Gly Arg Lys Ile Arg Gln Ala Phe
            340                 345                 350

Val Pro Ser Glu Pro Asp Trp Leu Ile Phe Ala Ala Asp Tyr Ser Gln
            355                 360                 365

Ile Glu Leu Arg Val Leu Ala His Ile Ala Glu Asp Asp Asn Leu Ile
        370                 375                 380

Glu Ala Phe Arg Arg Gly Leu Asp Ile His Thr Lys Thr Ala Met Asp
385                 390                 395                 400

Ile Phe His Val Ser Glu Glu Asp Val Thr Ala Asn Met Arg Arg Gln
                405                 410                 415

Ala Lys Ala Val Asn Phe Gly Ile Val Tyr Gly Ile Ser Asp Tyr Gly
                420                 425                 430

Leu Ala Gln Asn Leu Asn Ile Thr Arg Lys Glu Ala Ala Glu Phe Ile
            435                 440                 445

Glu Arg Tyr Phe Ala Ser Phe Pro Gly Val Lys Gln Tyr Met Asp Asn
        450                 455                 460

Ile Val Gln Glu Ala Lys Gln Lys Gly Tyr Val Thr Thr Leu Leu His
465                 470                 475                 480

Arg Arg Arg Tyr Leu Pro Asp Ile Thr Ser Arg Asn Phe Asn Val Arg
                485                 490                 495

Ser Phe Ala Glu Arg Thr Ala Met Asn Thr Pro Ile Gln Gly Ser Ala
                500                 505                 510

Ala Asp Ile Ile Lys Lys Ala Met Ile Asp Leu Ser Val Arg Leu Arg
            515                 520                 525

Glu Glu Arg Leu Gln Ala Arg Leu Leu Leu Gln Val His Asp Glu Leu
        530                 535                 540

Ile Leu Glu Ala Pro Lys Glu Glu Ile Glu Arg Leu Cys Arg Leu Val
545                 550                 555                 560

Pro Glu Val Met Glu Gln Ala Val Ala Leu Arg Val Pro Leu Lys Val
                565                 570                 575

Asp Tyr His Tyr Gly Pro Thr Trp Tyr Asp Ala Lys
            580                 585
```

(2) INFORMATION FOR SEQ ID NO:26:

(i) SEQUENCE CHARACTERISTICS:
        (A) LENGTH: 1773 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...1770
    (D) OTHER INFORMATION:

(xi) SEQUENCE DESCRIPTION: SEQ ID NO:26:

| | | | | | | | | | | | | | | | | |
|---|---|---|---|---|---|---|---|---|---|---|---|---|---|---|---|---|
| GTC | CAA | ACG | GAT | GAA | GGC | GAA | AAG | CCG | CTC | GCC | GGG | ATG | GAT | TTT | GCG | 48 |
| Val | Gln | Thr | Asp | Glu | Gly | Glu | Lys | Pro | Leu | Ala | Gly | Met | Asp | Phe | Ala | |
| 1 | | | | 5 | | | | | 10 | | | | | 15 | | |
| ATC | GCC | GAC | AGC | GTC | ACG | GAC | GAA | ATG | CTC | GCC | GAC | AAA | GCG | GCC | CTC | 96 |
| Ile | Ala | Asp | Ser | Val | Thr | Asp | Glu | Met | Leu | Ala | Asp | Lys | Ala | Ala | Leu | |
| | | | 20 | | | | | 25 | | | | | 30 | | | |
| GTC | GTG | GAG | GTG | GTG | GGC | GAC | AAC | TAT | CAC | CAT | GCC | CCG | ATT | GTC | GGG | 144 |
| Val | Val | Glu | Val | Val | Gly | Asp | Asn | Tyr | His | His | Ala | Pro | Ile | Val | Gly | |
| | | 35 | | | | | 40 | | | | | 45 | | | | |
| ATC | GCC | TTG | GCC | AAC | GAA | CGC | GGG | CGG | TTT | TTC | CTG | CGC | CCG | GAG | ACG | 192 |
| Ile | Ala | Leu | Ala | Asn | Glu | Arg | Gly | Arg | Phe | Phe | Leu | Arg | Pro | Glu | Thr | |
| | | 50 | | | | | 55 | | | | | 60 | | | | |
| GCG | CTC | GCC | GAT | CCG | AAA | TTT | CTC | GCT | TGG | CTT | GGC | GAT | GAG | ACG | AAG | 240 |
| Ala | Leu | Ala | Asp | Pro | Lys | Phe | Leu | Ala | Trp | Leu | Gly | Asp | Glu | Thr | Lys | |
| 65 | | | | 70 | | | | | 75 | | | | | 80 | | |
| AAA | AAA | ACG | ATG | TTT | GAT | TCA | AAG | CGG | GCG | GCC | GTC | GCG | CTA | AAA | TGG | 288 |
| Lys | Lys | Thr | Met | Phe | Asp | Ser | Lys | Arg | Ala | Ala | Val | Ala | Leu | Lys | Trp | |
| | | | 85 | | | | | 90 | | | | | 95 | | | |
| AAA | GGA | ATC | GAA | CTG | CGC | GGC | GTC | GTG | TTC | GAT | CTG | TTG | CTG | GCC | GCT | 336 |
| Lys | Gly | Ile | Glu | Leu | Arg | Gly | Val | Val | Phe | Asp | Leu | Leu | Leu | Ala | Ala | |
| | | | 100 | | | | | 105 | | | | | 110 | | | |
| TAC | TTG | CTC | GAT | CCG | GCG | CAG | GCG | GCG | GGC | GAC | GTT | GCC | GCG | GTG | GCG | 384 |
| Tyr | Leu | Leu | Asp | Pro | Ala | Gln | Ala | Ala | Gly | Asp | Val | Ala | Ala | Val | Ala | |
| | | 115 | | | | | 120 | | | | | 125 | | | | |
| AAA | ATG | CAT | CAG | TAC | GAG | GCG | GTG | CGA | TCG | GAT | GAG | GCG | GTC | TAT | GGA | 432 |
| Lys | Met | His | Gln | Tyr | Glu | Ala | Val | Arg | Ser | Asp | Glu | Ala | Val | Tyr | Gly | |
| | | 130 | | | | | 135 | | | | | 140 | | | | |
| AAA | GGA | GCG | AAG | CGG | ACG | GTT | CCT | GAT | GAA | CCG | ACG | CTT | GCC | GAG | CAT | 480 |
| Lys | Gly | Ala | Lys | Arg | Thr | Val | Pro | Asp | Glu | Pro | Thr | Leu | Ala | Glu | His | |
| 145 | | | | 150 | | | | | 155 | | | | | 160 | | |
| CTC | GCC | CGC | AAG | GCG | GCG | GCC | ATT | TGG | GCG | CTT | GAA | GAG | CCG | TTG | ATG | 528 |
| Leu | Ala | Arg | Lys | Ala | Ala | Ala | Ile | Trp | Ala | Leu | Glu | Glu | Pro | Leu | Met | |
| | | | 165 | | | | | 170 | | | | | 175 | | | |
| GAC | GAA | CTG | CGC | CGC | AAC | GAA | CAA | GAT | CGG | CTG | CTG | ACC | GAG | CTC | GAA | 576 |
| Asp | Glu | Leu | Arg | Arg | Asn | Glu | Gln | Asp | Arg | Leu | Leu | Thr | Glu | Leu | Glu | |
| | | | 180 | | | | | 185 | | | | | 190 | | | |
| CAG | CCG | CTG | GCT | GGC | ATT | TTG | GCC | AAT | ATG | GAA | TTT | ACT | GGA | GTG | AAA | 624 |
| Gln | Pro | Leu | Ala | Gly | Ile | Leu | Ala | Asn | Met | Glu | Phe | Thr | Gly | Val | Lys | |
| | | 195 | | | | | 200 | | | | | 205 | | | | |
| GTG | GAC | ACG | AAG | CGG | CTT | GAA | CAG | ATG | GGG | GCG | GAG | CTC | ACC | GAG | CAG | 672 |
| Val | Asp | Thr | Lys | Arg | Leu | Glu | Gln | Met | Gly | Ala | Glu | Leu | Thr | Glu | Gln | |
| | 210 | | | | | 215 | | | | | 220 | | | | | |
| CTG | CAG | GCG | GTC | GAG | CGG | CGC | ATT | TAC | GAA | CTC | GCC | GGC | CAA | GAG | TTC | 720 |
| Leu | Gln | Ala | Val | Glu | Arg | Arg | Ile | Tyr | Glu | Leu | Ala | Gly | Gln | Glu | Phe | |
| 225 | | | | 230 | | | | | 235 | | | | | 240 | | |
| AAC | ATT | AAC | TCG | CCG | AAA | CAG | CTC | GGG | ACG | GTT | TTA | TTT | GAC | AAG | CTG | 768 |
| Asn | Ile | Asn | Ser | Pro | Lys | Gln | Leu | Gly | Thr | Val | Leu | Phe | Asp | Lys | Leu | |
| | | | 245 | | | | | 250 | | | | | 255 | | | |
| CAG | CTC | CCG | GTG | TTG | AAA | AAG | ACA | AAA | ACC | GGC | TAT | TCG | ACT | TCA | GCC | 816 |
| Gln | Leu | Pro | Val | Leu | Lys | Lys | Thr | Lys | Thr | Gly | Tyr | Ser | Thr | Ser | Ala | |
| | | 260 | | | | | 265 | | | | | 270 | | | | |

```
GAT GTG CTT GAG AAG CTT GCA CCG CAC CAT GAA ATC GTC GAA CAT ATT    864
Asp Val Leu Glu Lys Leu Ala Pro His His Glu Ile Val Glu His Ile
        275                 280                 285

TTG CAT TAC CGC CAA CTC GGC AAG CTG CAG TCA ACG TAT ATT GAA GGG    912
Leu His Tyr Arg Gln Leu Gly Lys Leu Gln Ser Thr Tyr Ile Glu Gly
        290                 295                 300

CTG CTG AAA GTG GTG CAC CCC GTG ACG GGC AAA GTG CAC ACG ATG TTC    960
Leu Leu Lys Val Val His Pro Val Thr Gly Lys Val His Thr Met Phe
305                 310                 315                 320

AAT CAG GCG TTG ACG CAA ACC GGG CGC CTC AGC TCC GTC GAA CCG AAT   1008
Asn Gln Ala Leu Thr Gln Thr Gly Arg Leu Ser Ser Val Glu Pro Asn
            325                 330                 335

TTG CAA AAC ATT CCG ATT CGG CTT GAG GAA GGG CGG AAA ATC CGC CAG   1056
Leu Gln Asn Ile Pro Ile Arg Leu Glu Glu Gly Arg Lys Ile Arg Gln
                340                 345                 350

GCG TTC GTG CCG TCG GAG CCG GAC TGG CTC ATC TTT GCG GCC GAC TAT   1104
Ala Phe Val Pro Ser Glu Pro Asp Trp Leu Ile Phe Ala Ala Asp Tyr
                    355                 360                 365

TCG CAA ATC GAG CTG CGC GTC CTC GCC CAT ATC GCG GAA GAT GAC AAT   1152
Ser Gln Ile Glu Leu Arg Val Leu Ala His Ile Ala Glu Asp Asp Asn
        370                 375                 380

TTG ATT GAA GCG TTC CGG CGC GGG TTG GAC ATC CAT ACG AAA ACA GCC   1200
Leu Ile Glu Ala Phe Arg Arg Gly Leu Asp Ile His Thr Lys Thr Ala
385                 390                 395                 400

ATG GAC ATT TTC CAT GTG AGC GAA GAA GAC GTG ACA GCC AAC ATG CGC   1248
Met Asp Ile Phe His Val Ser Glu Glu Asp Val Thr Ala Asn Met Arg
            405                 410                 415

CGC CAA GCG AAG GCC GTC AAT TTT GGC ATC GTG TAC GGC ATT AGT GAT   1296
Arg Gln Ala Lys Ala Val Asn Phe Gly Ile Val Tyr Gly Ile Ser Asp
                420                 425                 430

TAC GGT CTG GCG CAA AAC TTG AAC ATT ACG CGC AAA GAA GCG GCT GAA   1344
Tyr Gly Leu Ala Gln Asn Leu Asn Ile Thr Arg Lys Glu Ala Ala Glu
                    435                 440                 445

TTT ATT GAG CGA TAT TTT GCC AGT TTT CCA GGT GTA AAG CAA TAT ATG   1392
Phe Ile Glu Arg Tyr Phe Ala Ser Phe Pro Gly Val Lys Gln Tyr Met
        450                 455                 460

GAC AAC ATT GTG CAA GAA GCG AAA CAA AAA GGG TAT GTG ACG ACG CTG   1440
Asp Asn Ile Val Gln Glu Ala Lys Gln Lys Gly Tyr Val Thr Thr Leu
465                 470                 475                 480

CTG CAT CGG CGC CGC TAT TTG CCC GAT ATT ACA AGC CGC AAC TTC AAC   1488
Leu His Arg Arg Arg Tyr Leu Pro Asp Ile Thr Ser Arg Asn Phe Asn
            485                 490                 495

GTC CGC AGC TTC GCC GAG CGG ACG GCG ATG AAC ACA CCG ATC CAA GGG   1536
Val Arg Ser Phe Ala Glu Arg Thr Ala Met Asn Thr Pro Ile Gln Gly
                500                 505                 510

AGT GCC GCT GAT ATT ATT AAA AAA GCG ATG ATC GAT CTA AGC GTG AGG   1584
Ser Ala Ala Asp Ile Ile Lys Lys Ala Met Ile Asp Leu Ser Val Arg
                    515                 520                 525

CTG CGC GAA GAA CGG CTG CAG GCG CGC CTG TTG CTG CAA GTG CAT GAC   1632
Leu Arg Glu Glu Arg Leu Gln Ala Arg Leu Leu Leu Gln Val His Asp
        530                 535                 540

GAA CTC ATT TTG GAG GCG CCG AAA GAG GAA ATC GAG CGG CTG TGC CGC   1680
Glu Leu Ile Leu Glu Ala Pro Lys Glu Glu Ile Glu Arg Leu Cys Arg
545                 550                 555                 560

CTC GTT CCA GAG GTG ATG GAG CAA GCC GTC GCA CTC CGC GTG CCG CTG   1728
Leu Val Pro Glu Val Met Glu Gln Ala Val Ala Leu Arg Val Pro Leu
            565                 570                 575

AAA GTC GAT TAC CAT TAC GGT CCG ACG TGG TAC GAC GCC AAA TAA       1773
Lys Val Asp Tyr His Tyr Gly Pro Thr Trp Tyr Asp Ala Lys
                580                 585                 590
```

(2) INFORMATION FOR SEQ ID NO:27:

(i) SEQUENCE CHARACTERISTICS:
        (A) LENGTH: 590 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:27:

```
Val Gln Thr Asp Glu Gly Glu Lys Pro Leu Ala Gly Met Asp Phe Ala
  1               5                  10                  15

Ile Ala Asp Ser Val Thr Asp Glu Met Leu Ala Asp Lys Ala Ala Leu
             20                  25                  30

Val Val Glu Val Val Gly Asp Asn Tyr His His Ala Pro Ile Val Gly
         35                  40                  45

Ile Ala Leu Ala Asn Glu Arg Gly Arg Phe Phe Leu Arg Pro Glu Thr
 50                  55                  60

Ala Leu Ala Asp Pro Lys Phe Leu Ala Trp Leu Gly Asp Glu Thr Lys
 65                  70                  75                  80

Lys Lys Thr Met Phe Asp Ser Lys Arg Ala Ala Val Ala Leu Lys Trp
                 85                  90                  95

Lys Gly Ile Glu Leu Arg Gly Val Val Phe Asp Leu Leu Leu Ala Ala
                100                 105                 110

Tyr Leu Leu Asp Pro Ala Gln Ala Ala Gly Asp Val Ala Ala Val Ala
                115                 120                 125

Lys Met His Gln Tyr Glu Ala Val Arg Ser Asp Glu Ala Val Tyr Gly
    130                 135                 140

Lys Gly Ala Lys Arg Thr Val Pro Asp Glu Pro Thr Leu Ala Glu His
145                 150                 155                 160

Leu Ala Arg Lys Ala Ala Ala Ile Trp Ala Leu Glu Glu Pro Leu Met
                165                 170                 175

Asp Glu Leu Arg Arg Asn Glu Gln Asp Arg Leu Leu Thr Glu Leu Glu
                180                 185                 190

Gln Pro Leu Ala Gly Ile Leu Ala Asn Met Glu Phe Thr Gly Val Lys
            195                 200                 205

Val Asp Thr Lys Arg Leu Glu Gln Met Gly Ala Glu Leu Thr Glu Gln
    210                 215                 220

Leu Gln Ala Val Glu Arg Arg Ile Tyr Glu Leu Ala Gly Gln Glu Phe
225                 230                 235                 240

Asn Ile Asn Ser Pro Lys Gln Leu Gly Thr Val Leu Phe Asp Lys Leu
                245                 250                 255

Gln Leu Pro Val Leu Lys Lys Thr Lys Thr Gly Tyr Ser Thr Ser Ala
                260                 265                 270

Asp Val Leu Glu Lys Leu Ala Pro His His Glu Ile Val Glu His Ile
    275                 280                 285

Leu His Tyr Arg Gln Leu Gly Lys Leu Gln Ser Thr Tyr Ile Glu Gly
    290                 295                 300
```

```
Leu Leu Lys Val Val His Pro Val Thr Gly Lys Val His Thr Met Phe
305                 310                 315                 320

Asn Gln Ala Leu Thr Gln Thr Gly Arg Leu Ser Ser Val Glu Pro Asn
            325                 330                 335

Leu Gln Asn Ile Pro Ile Arg Leu Glu Glu Gly Arg Lys Ile Arg Gln
            340                 345                 350

Ala Phe Val Pro Ser Glu Pro Asp Trp Leu Ile Phe Ala Ala Asp Tyr
            355                 360                 365

Ser Gln Ile Glu Leu Arg Val Leu Ala His Ile Ala Glu Asp Asp Asn
370                 375                 380

Leu Ile Glu Ala Phe Arg Arg Gly Leu Asp Ile His Thr Lys Thr Ala
385                 390                 395                 400

Met Asp Ile Phe His Val Ser Glu Glu Asp Val Thr Ala Asn Met Arg
                405                 410                 415

Arg Gln Ala Lys Ala Val Asn Phe Gly Ile Val Tyr Gly Ile Ser Asp
                420                 425                 430

Tyr Gly Leu Ala Gln Asn Leu Asn Ile Thr Arg Lys Glu Ala Ala Glu
            435                 440                 445

Phe Ile Glu Arg Tyr Phe Ala Ser Phe Pro Gly Val Lys Gln Tyr Met
450                 455                 460

Asp Asn Ile Val Gln Glu Ala Lys Gln Lys Gly Tyr Val Thr Thr Leu
465                 470                 475                 480

Leu His Arg Arg Arg Tyr Leu Pro Asp Ile Thr Ser Arg Asn Phe Asn
                485                 490                 495

Val Arg Ser Phe Ala Glu Arg Thr Ala Met Asn Thr Pro Ile Gln Gly
            500                 505                 510

Ser Ala Ala Asp Ile Ile Lys Lys Ala Met Ile Asp Leu Ser Val Arg
            515                 520                 525

Leu Arg Glu Glu Arg Leu Gln Ala Arg Leu Leu Leu Gln Val His Asp
            530                 535                 540

Glu Leu Ile Leu Glu Ala Pro Lys Glu Glu Ile Glu Arg Leu Cys Arg
545                 550                 555                 560

Leu Val Pro Glu Val Met Glu Gln Ala Val Ala Leu Arg Val Pro Leu
                565                 570                 575

Lys Val Asp Tyr His Tyr Gly Pro Thr Trp Tyr Asp Ala Lys
            580                 585                 590

(2) INFORMATION FOR SEQ ID NO:28:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:28:

AACGCAGTCT ACGGGTTTAC GATGATGTTA ACAAAATTT TGGCGGAAGA GCAGCCGACC      60

CACATTCTCG TGGCGTTTGA CGCCGGGAAA ACGACGTTC                            99
```

(2) INFORMATION FOR SEQ ID NO:29:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

```
GCAGCGGAAA CTGTTCCGAC AGTTCCGGCG GCGTCTGCTG CCGCCCGCCT TTAAAGTCTT      60

GGAACGTTTC ATGGCGGAAC GTCGTTTTCC CGGCGTC                              97
```

(2) INFORMATION FOR SEQ ID NO:30:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

```
GCAGCGGAAA CTGTTCCGAC AGTTCCGGCG GCGTCTGCTG CCGGCCGCCT TTCGCGTCTT      60

GGAACGTTTC ATGGCGGAAC GTCGTTTTCC CGGCGTC                              97
```

(2) INFORMATION FOR SEQ ID NO:31:

(i) SEQUENCE CHARACTERISTICS:
        (A) LENGTH: 2631 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...2631
        (D) OTHER INFORMATION:

(xi) SEQUENCE DESCRIPTION: SEQ ID NO:31:

```
TTG AAA AAC AAG CTC GTC TTA ATT GAC GGC AAC AGC GTG GCG TAC CGC      48
Leu Lys Asn Lys Leu Val Leu Ile Asp Gly Asn Ser Val Ala Tyr Arg
 1               5                  10                  15
```

```
GCC TTT TTC GCG TTG CCG CTT TTG CAT AAC GAT AAA GGG ATT CAT ACG        96
Ala Phe Phe Ala Leu Pro Leu Leu His Asn Asp Lys Gly Ile His Thr
             20                  25                  30

AAC GCA GTC TAC GGG TTT ACG ATG ATG TTA AAC AAA ATT TTG GCG GAA       144
Asn Ala Val Tyr Gly Phe Thr Met Met Leu Asn Lys Ile Leu Ala Glu
         35                  40                  45

GAG CAG CCG ACC CAC ATT CTC GTG GCG TTT GAC GCC GGG AAA ACG ACG       192
Glu Gln Pro Thr His Ile Leu Val Ala Phe Asp Ala Gly Lys Thr Thr
         50                  55                  60

TTC CGC CAT GAA ACG TTC CAA GAC TTT AAA GGC GGG CGG CAG CAG ACG       240
Phe Arg His Glu Thr Phe Gln Asp Phe Lys Gly Gly Arg Gln Gln Thr
65                  70                  75                  80

CCG CCG GAA CTG TCG GAA CAG TTT CCG CTG CTG CGC GAA TTG CTC AAG       288
Pro Pro Glu Leu Ser Glu Gln Phe Pro Leu Leu Arg Glu Leu Leu Lys
                 85                  90                  95

GCG TAC CGC ATC CCC GCC TAT GAG CTC GAC CAT TAC GAA GCG GAC GAT       336
Ala Tyr Arg Ile Pro Ala Tyr Glu Leu Asp His Tyr Glu Ala Asp Asp
                100                 105                 110

ATT ATC GGA ACG ATG GCG GCG CGG GCT GAG CGA GAA GGG TTT GCA GTG       384
Ile Ile Gly Thr Met Ala Ala Arg Ala Glu Arg Glu Gly Phe Ala Val
            115                 120                 125

AAA GTC ATT TCC GGC GAC CGC GAT TTA ACC CAG CTT GCT TCC CCG CAA       432
Lys Val Ile Ser Gly Asp Arg Asp Leu Thr Gln Leu Ala Ser Pro Gln
130                 135                 140

GTG ACG GTG GAG ATT ACG AAA AAA GGG ATT ACC GAC ATC GAG TCG TAC       480
Val Thr Val Glu Ile Thr Lys Lys Gly Ile Thr Asp Ile Glu Ser Tyr
145                 150                 155                 160

ACG CCG GAG ACG GTC GTG GAA AAA TAC GGC CTC ACC CCG GAG CAA ATT       528
Thr Pro Glu Thr Val Val Glu Lys Tyr Gly Leu Thr Pro Glu Gln Ile
                165                 170                 175

GTC GAC TTG AAA GGA TTG ATG GGC GAC AAA TCC GAC AAC ATC CCT GGC       576
Val Asp Leu Lys Gly Leu Met Gly Asp Lys Ser Asp Asn Ile Pro Gly
            180                 185                 190

GTG CCC GGC ATC GGG GAA AAA ACA GCC GTC AAG CTG CTC AAG CAA TTC       624
Val Pro Gly Ile Gly Glu Lys Thr Ala Val Lys Leu Leu Lys Gln Phe
        195                 200                 205

GGC ACG GTC GAA AAC GTA CTG GCA TCG ATC GAT GAG ATC AAA GGG GAG       672
Gly Thr Val Glu Asn Val Leu Ala Ser Ile Asp Glu Ile Lys Gly Glu
210                 215                 220

AAG CTG AAA GAA AAT TTG CGC CAA TAC CGG GAT TTG GCG CTT TTA AGC       720
Lys Leu Lys Glu Asn Leu Arg Gln Tyr Arg Asp Leu Ala Leu Leu Ser
225                 230                 235                 240

AAA CAG CTG GCC GCT ATT TGC CGC GAC GCC CCG GTT GAG CTG ACG CTC       768
Lys Gln Leu Ala Ala Ile Cys Arg Asp Ala Pro Val Glu Leu Thr Leu
                245                 250                 255

GAT GAC ATT GTC TAC AAA GGA GAA GAC CGG GAA AAA GTG GTC GCC TTG       816
Asp Asp Ile Val Tyr Lys Gly Glu Asp Arg Glu Lys Val Val Ala Leu
            260                 265                 270

TTT CAG GAG CTC GGA TTC CAG TCG TTT CTC GAC AAG ATG GCC GTC CAA       864
Phe Gln Glu Leu Gly Phe Gln Ser Phe Leu Asp Lys Met Ala Val Gln
        275                 280                 285

ACG GAT GAA GGC GAA AAG CCG CTC GCC GGG ATG GAT TTT GCG ATC GCC       912
Thr Asp Glu Gly Glu Lys Pro Leu Ala Gly Met Asp Phe Ala Ile Ala
290                 295                 300

GAC AGC GTC ACG GAC GAA ATG CTC GCC GAC AAA GCG GCC CTC GTC GTG       960
Asp Ser Val Thr Asp Glu Met Leu Ala Asp Lys Ala Ala Leu Val Val
305                 310                 315                 320

GAG GTG GTG GGC GAC AAC TAT CAC CAT GCC CCG ATT GTC GGG ATC GCC      1008
Glu Val Val Gly Asp Asn Tyr His His Ala Pro Ile Val Gly Ile Ala
```

```
                    325                    330                      335
TTG GCC AAC GAA CGC GGG CGG TTT TTC CTG CGC CCG GAG ACG GCG CTC    1056
Leu Ala Asn Glu Arg Gly Arg Phe Phe Leu Arg Pro Glu Thr Ala Leu
            340                 345                 350

GCC GAT CCG AAA TTT CTC GCT TGG CTT GGC GAT GAG ACG AAG AAA AAA    1104
Ala Asp Pro Lys Phe Leu Ala Trp Leu Gly Asp Glu Thr Lys Lys Lys
        355                 360                 365

ACG ATG TTT GAT TCA AAG CGG GCG GCC GTC GCG CTA AAA TGG AAA GGA    1152
Thr Met Phe Asp Ser Lys Arg Ala Ala Val Ala Leu Lys Trp Lys Gly
    370                 375                 380

ATC GAA CTG CGC GGC GTC GTG TTC GAT CTG TTG CTG GCC GCT TAC TTG    1200
Ile Glu Leu Arg Gly Val Val Phe Asp Leu Leu Leu Ala Ala Tyr Leu
385                 390                 395                 400

CTC GAT CCG GCG CAG GCG GCG GGC GAC GTT GCC GCG GTG GCG AAA ATG    1248
Leu Asp Pro Ala Gln Ala Ala Gly Asp Val Ala Ala Val Ala Lys Met
                405                 410                 415

CAT CAG TAC GAG GCG GTG CGA TCG GAT GAG GCG GTC TAT GGA AAA GGA    1296
His Gln Tyr Glu Ala Val Arg Ser Asp Glu Ala Val Tyr Gly Lys Gly
            420                 425                 430

GCG AAG CGG ACG GTT CCT GAT GAA CCG ACG CTT GCC GAG CAT CTC GCC    1344
Ala Lys Arg Thr Val Pro Asp Glu Pro Thr Leu Ala Glu His Leu Ala
        435                 440                 445

CGC AAG GCG GCG GCC ATT TGG GCG CTT GAA GAG CCG TTG ATG GAC GAA    1392
Arg Lys Ala Ala Ala Ile Trp Ala Leu Glu Glu Pro Leu Met Asp Glu
    450                 455                 460

CTG CGC CGC AAC GAA CAA GAT CGG CTG CTG ACC GAG CTC GAA CAG CCG    1440
Leu Arg Arg Asn Glu Gln Asp Arg Leu Leu Thr Glu Leu Glu Gln Pro
465                 470                 475                 480

CTG GCT GGC ATT TTG GCC AAT ATG GAA TTT ACT GGA GTG AAA GTG GAC    1488
Leu Ala Gly Ile Leu Ala Asn Met Glu Phe Thr Gly Val Lys Val Asp
                485                 490                 495

ACG AAG CGG CTT GAA CAG ATG GGG GCG GAG CTC ACC GAG CAG CTG CAG    1536
Thr Lys Arg Leu Glu Gln Met Gly Ala Glu Leu Thr Glu Gln Leu Gln
            500                 505                 510

GCG GTC GAG CGG CGC ATT TAC GAA CTC GCC GGC CAA GAG TTC AAC ATT    1584
Ala Val Glu Arg Arg Ile Tyr Glu Leu Ala Gly Gln Glu Phe Asn Ile
        515                 520                 525

AAC TCG CCG AAA CAG CTC GGG ACG GTT TTA TTT GAC AAG CTG CAG CTC    1632
Asn Ser Pro Lys Gln Leu Gly Thr Val Leu Phe Asp Lys Leu Gln Leu
    530                 535                 540

CCG GTG TTG AAA AAG ACA AAA ACC GGC TAT TCG ACT TCA GCC GAT GTG    1680
Pro Val Leu Lys Lys Thr Lys Thr Gly Tyr Ser Thr Ser Ala Asp Val
545                 550                 555                 560

CTT GAG AAG CTT GCA CCG CAC CAT GAA ATC GTC GAA CAT ATT TTG CAT    1728
Leu Glu Lys Leu Ala Pro His His Glu Ile Val Glu His Ile Leu His
                565                 570                 575

TAC CGC CAA CTC GGC AAG CTG CAG TCA ACG TAT ATT GAA GGG CTG CTG    1776
Tyr Arg Gln Leu Gly Lys Leu Gln Ser Thr Tyr Ile Glu Gly Leu Leu
            580                 585                 590

AAA GTG GTG CAC CCC GTG ACG GGC AAA GTG CAC ACG ATG TTC AAT CAG    1824
Lys Val Val His Pro Val Thr Gly Lys Val His Thr Met Phe Asn Gln
        595                 600                 605

GCG TTG ACG CAA ACC GGG CGC CTC AGC TCC GTC GAA CCG AAT TTG CAA    1872
Ala Leu Thr Gln Thr Gly Arg Leu Ser Ser Val Glu Pro Asn Leu Gln
    610                 615                 620

AAC ATT CCG ATT CGG CTT GAG GAA GGG CGG AAA ATC CGC CAG GCG TTC    1920
Asn Ile Pro Ile Arg Leu Glu Glu Gly Arg Lys Ile Arg Gln Ala Phe
625                 630                 635                 640

GTG CCG TCG GAG CCG GAC TGG CTC ATC TTT GCG GCC GAC TAT TCG CAA    1968
```

```
Val Pro Ser Glu Pro Asp Trp Leu Ile Phe Ala Asp Tyr Ser Gln
            645                 650                 655

ATC GAG CTG CGC GTC CTC GCC CAT ATC GCG GAA GAT GAC AAT TTG ATT    2016
Ile Glu Leu Arg Val Leu Ala His Ile Ala Glu Asp Asp Asn Leu Ile
            660                 665                 670

GAA GCG TTC CGG CGC GGG TTG GAC ATC CAT ACG AAA ACA GCC ATG GAC    2064
Glu Ala Phe Arg Arg Gly Leu Asp Ile His Thr Lys Thr Ala Met Asp
            675                 680                 685

ATT TTC CAT GTG AGC GAA GAA GAC GTG ACA GCC AAC ATG CGC CGC CAA    2112
Ile Phe His Val Ser Glu Glu Asp Val Thr Ala Asn Met Arg Arg Gln
        690                 695                 700

GCG AAG GCC GTC AAT TTT GGC ATC GTG TAC GGC ATT AGT GAT TAC GGT    2160
Ala Lys Ala Val Asn Phe Gly Ile Val Tyr Gly Ile Ser Asp Tyr Gly
705                 710                 715                 720

CTG GCG CAA AAC TTG AAC ATT ACG CGC AAA GAA GCG GCT GAA TTT ATT    2208
Leu Ala Gln Asn Leu Asn Ile Thr Arg Lys Glu Ala Ala Glu Phe Ile
                725                 730                 735

GAG CGA TAT TTT GCC AGT TTT CCA GGT GTA AAG CAA TAT ATG GAC AAC    2256
Glu Arg Tyr Phe Ala Ser Phe Pro Gly Val Lys Gln Tyr Met Asp Asn
            740                 745                 750

ATT GTG CAA GAA GCG AAA CAA AAA GGG TAT GTG ACG ACG CTG CTG CAT    2304
Ile Val Gln Glu Ala Lys Gln Lys Gly Tyr Val Thr Thr Leu Leu His
        755                 760                 765

CGG CGC CGC TAT TTG CCC GAT ATT ACA AGC CGC AAC TTC AAC GTC CGC    2352
Arg Arg Arg Tyr Leu Pro Asp Ile Thr Ser Arg Asn Phe Asn Val Arg
770                 775                 780

AGC TTC GCC GAG CGG ACG GCG ATG AAC ACA CCG ATC CAA GGG AGT GCC    2400
Ser Phe Ala Glu Arg Thr Ala Met Asn Thr Pro Ile Gln Gly Ser Ala
785                 790                 795                 800

GCT GAT ATT ATT AAA AAA GCG ATG ATC GAT CTA AGC GTG AGG CTG CGC    2448
Ala Asp Ile Ile Lys Lys Ala Met Ile Asp Leu Ser Val Arg Leu Arg
                805                 810                 815

GAA GAA CGG CTG CAG GCG CGC CTG TTG CTG CAA GTG CAT GAC GAA CTC    2496
Glu Glu Arg Leu Gln Ala Arg Leu Leu Leu Gln Val His Asp Glu Leu
            820                 825                 830

ATT TTG GAG GCG CCG AAA GAG GAA ATC GAG CGG CTG TGC CGC CTC GTT    2544
Ile Leu Glu Ala Pro Lys Glu Glu Ile Glu Arg Leu Cys Arg Leu Val
        835                 840                 845

CCA GAG GTG ATG GAG CAA GCC GTC GCA CTC CGC GTG CCG CTG AAA GTC    2592
Pro Glu Val Met Glu Gln Ala Val Ala Leu Arg Val Pro Leu Lys Val
850                 855                 860

GAT TAC CAT TAC GGT CCG ACG TGG TAC GAC GCC AAA TAA               2631
Asp Tyr His Tyr Gly Pro Thr Trp Tyr Asp Ala Lys  *
865                 870                 875

(2) INFORMATION FOR SEQ ID NO:32:

(i) SEQUENCE CHARACTERISTICS:
        (A) LENGTH: 876 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:32:
```

-continued

```
Leu Lys Asn Lys Leu Val Leu Ile Asp Gly Asn Ser Val Ala Tyr Arg
  1               5                  10                  15

Ala Phe Phe Ala Leu Pro Leu Leu His Asn Asp Lys Gly Ile His Thr
             20                  25                  30

Asn Ala Val Tyr Gly Phe Thr Met Met Leu Asn Lys Ile Leu Ala Glu
             35                  40                  45

Glu Gln Pro Thr His Ile Leu Val Ala Phe Asp Ala Gly Lys Thr Thr
         50                  55                  60

Phe Arg His Glu Thr Phe Gln Asp Phe Lys Gly Gly Arg Gln Gln Thr
 65              70                  75                  80

Pro Pro Glu Leu Ser Glu Gln Phe Pro Leu Leu Arg Glu Leu Leu Lys
                 85                  90                  95

Ala Tyr Arg Ile Pro Ala Tyr Glu Leu Asp His Tyr Glu Ala Asp Asp
                100                 105                 110

Ile Ile Gly Thr Met Ala Ala Arg Ala Glu Arg Gly Phe Ala Val
                115                 120                 125

Lys Val Ile Ser Gly Asp Arg Asp Leu Thr Gln Leu Ala Ser Pro Gln
                130                 135                 140

Val Thr Val Glu Ile Thr Lys Lys Gly Ile Thr Asp Ile Glu Ser Tyr
145                 150                 155                 160

Thr Pro Glu Thr Val Val Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Ile Lys Gly Glu
            210                 215                 220

Lys Leu Lys Glu Asn Leu Arg Gln Tyr Arg Asp Leu Ala Leu Leu Ser
225                 230                 235                 240

Lys Gln Leu Ala Ala Ile Cys Arg Asp Ala Pro Val Glu Leu Thr Leu
                245                 250                 255

Asp Asp Ile Val Tyr Lys Gly Glu Asp Arg Glu Lys Val Val Ala Leu
                260                 265                 270

Phe Gln Glu Leu Gly Phe Gln Ser Phe Leu Asp Lys Met Ala Val Gln
                275                 280                 285

Thr Asp Glu Gly Glu Lys Pro Leu Ala Gly Met Asp Phe Ala Ile Ala
            290                 295                 300

Asp Ser Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
                340                 345                 350

Ala Asp Pro Lys Phe Leu Ala Trp Leu Gly Asp Glu Thr Lys Lys Lys
            355                 360                 365

Thr Met Phe Asp Ser Lys Arg Ala Ala Val Ala Leu Lys Trp Lys Gly
            370                 375                 380

Ile Glu Leu Arg Gly Val Val Phe Asp Leu Leu Leu Ala Ala Tyr Leu
385                 390                 395                 400

Leu Asp Pro Ala Gln Ala Ala Gly Asp Val Ala Ala Val Ala Lys Met
                405                 410                 415
```

-continued

```
His Gln Tyr Glu Ala Val Arg Ser Asp Glu Ala Val Tyr Gly Lys Gly
            420                 425                 430

Ala Lys Arg Thr Val Pro Asp Glu Pro Thr Leu Ala Glu His Leu Ala
        435                 440                 445

Arg Lys Ala Ala Ala Ile Trp Ala Leu Glu Glu Pro Leu Met Asp Glu
450                 455                 460

Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp
                485                 490                 495

Thr Lys Arg Leu Glu Gln Met Gly Ala Glu Leu Thr Glu Gln Leu Gln
            500                 505                 510

Ala Val Glu Arg Arg Ile Tyr Glu Leu Ala Gly Gln Glu Phe Asn Ile
        515                 520                 525

Asn Ser Pro Lys Gln Leu Gly Thr Val Leu Phe Asp Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
                565                 570                 575

Tyr Arg Gln Leu Gly Lys Leu Gln Ser Thr Tyr Ile Glu Gly Leu Leu
            580                 585                 590

Lys Val His Pro Val Thr Gly Lys Val His Thr Met Phe Asn Gln
        595                 600                 605

Ala Leu Thr Gln Thr Gly Arg Leu Ser Ser Val Glu Pro Asn Leu Gln
610                 615                 620

Asn Ile Pro Ile Arg Leu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
            660                 665                 670

Glu Ala Phe Arg Arg Gly Leu Asp Ile His Thr Lys Thr Ala Met Asp
        675                 680                 685

Ile Phe His Val Ser Glu Glu Asp Val Thr Ala Asn Met Arg Arg Gln
690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815

Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
```

```
                835                840                845
    Pro Glu Val Met Glu Gln Ala Val Ala Leu Arg Val Pro Leu Lys Val
        850                 855                 860

Asp Tyr His Tyr Gly Pro Thr Trp Tyr Asp Ala Lys
    865                 870                 875

(2) INFORMATION FOR SEQ ID NO:33:

(i) SEQUENCE CHARACTERISTICS:
        (A) LENGTH: 2631 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...2631
        (D) OTHER INFORMATION:

(xi) SEQUENCE DESCRIPTION: SEQ ID NO:33:

TTG AAA AAC AAG CTC GTC TTA ATT GAC GGC AAC AGC GTG GCG TAC CGC        48
Leu Lys Asn Lys Leu Val Leu Ile Asp Gly Asn Ser Val Ala Tyr Arg
1               5                  10                  15

GCC TTT TTC GCG TTG CCG CTT TTG CAT AAC GAT AAA GGG ATT CAT ACG        96
Ala Phe Phe Ala Leu Pro Leu Leu His Asn Asp Lys Gly Ile His Thr
            20                  25                  30

AAC GCA GTC TAC GGG TTT ACG ATG ATG TTA AAC AAA ATT TTG GCG GAA       144
Asn Ala Val Tyr Gly Phe Thr Met Met Leu Asn Lys Ile Leu Ala Glu
        35                  40                  45

GAG CAG CCG ACC CAC ATT CTC GTG GCG TTT GAC GCC GGG AAA ACG ACG       192
Glu Gln Pro Thr His Ile Leu Val Ala Phe Asp Ala Gly Lys Thr Thr
    50                  55                  60

TTC CGC CAT GAA ACG TTC CAA GAC GCG AAA GGC GGC CGG CAG CAG ACG       240
Phe Arg His Glu Thr Phe Gln Asp Ala Lys Gly Gly Arg Gln Gln Thr
65                  70                  75                  80

CCG CCG GAA CTG TCG GAA CAG TTT CCG CTG CTG CGC GAA TTG CTC AAG       288
Pro Pro Glu Leu Ser Glu Gln Phe Pro Leu Leu Arg Glu Leu Leu Lys
                85                  90                  95

GCG TAC CGC ATC CCC GCC TAT GAG CTC GAC CAT TAC GAA GCG GAC GAT       336
Ala Tyr Arg Ile Pro Ala Tyr Glu Leu Asp His Tyr Glu Ala Asp Asp
            100                 105                 110

ATT ATC GGA ACG ATG GCG GCG CGG GCT GAG CGA GAA GGG TTT GCA GTG       384
Ile Ile Gly Thr Met Ala Ala Arg Ala Glu Arg Glu Gly Phe Ala Val
        115                 120                 125

AAA GTC ATT TCC GGC GAC CGC GAT TTA ACC CAG CTT GCT TCC CCG CAA       432
Lys Val Ile Ser Gly Asp Arg Asp Leu Thr Gln Leu Ala Ser Pro Gln
    130                 135                 140

GTG ACG GTG GAG ATT ACG AAA AAA GGG ATT ACC GAC ATC GAG TCG TAC       480
Val Thr Val Glu Ile Thr Lys Lys Gly Ile Thr Asp Ile Glu Ser Tyr
145                 150                 155                 160

ACG CCG GAG ACG GTC GTG GAA AAA TAC GGC CTC ACC CCG GAG CAA ATT       528
Thr Pro Glu Thr Val Val Glu Lys Tyr Gly Leu Thr Pro Glu Gln Ile
                165                 170                 175

GTC GAC TTG AAA GGA TTG ATG GGC GAC AAA TCC GAC AAC ATC CCT GGC       576
```

```
Val Asp Leu Lys Gly Leu Met Gly Asp Lys Ser Asp Asn Ile Pro Gly
            180                 185                 190

GTG CCC GGC ATC GGG GAA AAA ACA GCC GTC AAG CTG CTC AAG CAA TTC       624
Val Pro Gly Ile Gly Glu Lys Thr Ala Val Lys Leu Leu Lys Gln Phe
        195                 200                 205

GGC ACG GTC GAA AAC GTA CTG GCA TCG ATC GAT GAG ATC AAA GGG GAG       672
Gly Thr Val Glu Asn Val Leu Ala Ser Ile Asp Glu Ile Lys Gly Glu
    210                 215                 220

AAG CTG AAA GAA AAT TTG CGC CAA TAC CGG GAT TTG GCG CTT TTA AGC       720
Lys Leu Lys Glu Asn Leu Arg Gln Tyr Arg Asp Leu Ala Leu Leu Ser
225                 230                 235                 240

AAA CAG CTG GCC GCT ATT TGC CGC GAC GCC CCG GTT GAG CTG ACG CTC       768
Lys Gln Leu Ala Ala Ile Cys Arg Asp Ala Pro Val Glu Leu Thr Leu
                245                 250                 255

GAT GAC ATT GTC TAC AAA GGA GAA GAC CGG GAA AAA GTG GTC GCC TTG       816
Asp Asp Ile Val Tyr Lys Gly Glu Asp Arg Glu Lys Val Val Ala Leu
            260                 265                 270

TTT CAG GAG CTC GGA TTC CAG TCG TTT CTC GAC AAG ATG GCC GTC CAA       864
Phe Gln Glu Leu Gly Phe Gln Ser Phe Leu Asp Lys Met Ala Val Gln
        275                 280                 285

ACG GAT GAA GGC GAA AAG CCG CTC GCC GGG ATG GAT TTT GCG ATC GCC       912
Thr Asp Glu Gly Glu Lys Pro Leu Ala Gly Met Asp Phe Ala Ile Ala
    290                 295                 300

GAC AGC GTC ACG GAC GAA ATG CTC GCC GAC AAA GCG GCC CTC GTC GTG       960
Asp Ser Val Thr Asp Glu Met Leu Ala Asp Lys Ala Ala Leu Val Val
305                 310                 315                 320

GAG GTG GTG GGC GAC AAC TAT CAC CAT GCC CCG ATT GTC GGG ATC GCC      1008
Glu Val Val Gly Asp Asn Tyr His His Ala Pro Ile Val Gly Ile Ala
                325                 330                 335

TTG GCC AAC GAA CGC GGG CGG TTT TTC CTG CGC CCG GAG ACG GCG CTC      1056
Leu Ala Asn Glu Arg Gly Arg Phe Phe Leu Arg Pro Glu Thr Ala Leu
            340                 345                 350

GCC GAT CCG AAA TTT CTC GCT TGG CTT GGC GAT GAG ACG AAG AAA AAA      1104
Ala Asp Pro Lys Phe Leu Ala Trp Leu Gly Asp Glu Thr Lys Lys Lys
        355                 360                 365

ACG ATG TTT GAT TCA AAG CGG GCG GCC GTC GCG CTA AAA TGG AAA GGA      1152
Thr Met Phe Asp Ser Lys Arg Ala Ala Val Ala Leu Lys Trp Lys Gly
    370                 375                 380

ATC GAA CTG CGC GGC GTC GTG TTC GAT CTG TTG CTG GCC GCT TAC TTG      1200
Ile Glu Leu Arg Gly Val Val Phe Asp Leu Leu Leu Ala Ala Tyr Leu
385                 390                 395                 400

CTC GAT CCG GCG CAG GCG GCG GGC GAC GTT GCC GCG GTG GCG AAA ATG      1248
Leu Asp Pro Ala Gln Ala Ala Gly Asp Val Ala Ala Val Ala Lys Met
                405                 410                 415

CAT CAG TAC GAG GCG GTG CGA TCG GAT GAG GCG GTC TAT GGA AAA GGA      1296
His Gln Tyr Glu Ala Val Arg Ser Asp Glu Ala Val Tyr Gly Lys Gly
            420                 425                 430

GCG AAG CGG ACG GTT CCT GAT GAA CCG ACG CTT GCC GAG CAT CTC GCC      1344
Ala Lys Arg Thr Val Pro Asp Glu Pro Thr Leu Ala Glu His Leu Ala
        435                 440                 445

CGC AAG GCG GCG GCC ATT TGG GCG CTT GAA GAG CCG TTG ATG GAC GAA      1392
Arg Lys Ala Ala Ala Ile Trp Ala Leu Glu Glu Pro Leu Met Asp Glu
    450                 455                 460

CTG CGC CGC AAC GAA CAA GAT CGG CTG CTG ACC GAG CTC GAA CAG CCG      1440
Leu Arg Arg Asn Glu Gln Asp Arg Leu Leu Thr Glu Leu Glu Gln Pro
465                 470                 475                 480

CTG GCT GGC ATT TTG GCC AAT ATG GAA TTT ACT GGA GTG AAA GTG GAC      1488
Leu Ala Gly Ile Leu Ala Asn Met Glu Phe Thr Gly Val Lys Val Asp
                485                 490                 495
```

```
ACG AAG CGG CTT GAA CAG ATG GGG GCG GAG CTC ACC GAG CAG CTG CAG       1536
Thr Lys Arg Leu Glu Gln Met Gly Ala Glu Leu Thr Glu Gln Leu Gln
            500                 505                 510

GCG GTC GAG CGG CGC ATT TAC GAA CTC GCC GGC CAA GAG TTC AAC ATT       1584
Ala Val Glu Arg Arg Ile Tyr Glu Leu Ala Gly Gln Glu Phe Asn Ile
            515                 520                 525

AAC TCG CCG AAA CAG CTC GGG ACG GTT TTA TTT GAC AAG CTG CAG CTC       1632
Asn Ser Pro Lys Gln Leu Gly Thr Val Leu Phe Asp Lys Leu Gln Leu
            530                 535                 540

CCG GTG TTG AAA AAG ACA AAA ACC GGC TAT TCG ACT TCA GCC GAT GTG       1680
Pro Val Leu Lys Lys Thr Lys Thr Gly Tyr Ser Thr Ser Ala Asp Val
545                 550                 555                 560

CTT GAG AAG CTT GCA CCG CAC CAT GAA ATC GTC GAA CAT ATT TTG CAT       1728
Leu Glu Lys Leu Ala Pro His His Glu Ile Val Glu His Ile Leu His
            565                 570                 575

TAC CGC CAA CTC GGC AAG CTG CAG TCA ACG TAT ATT GAA GGG CTG CTG       1776
Tyr Arg Gln Leu Gly Lys Leu Gln Ser Thr Tyr Ile Glu Gly Leu Leu
            580                 585                 590

AAA GTG GTG CAC CCC GTG ACG GGC AAA GTG CAC ACG ATG TTC AAT CAG       1824
Lys Val Val His Pro Val Thr Gly Lys Val His Thr Met Phe Asn Gln
            595                 600                 605

GCG TTG ACG CAA ACC GGG CGC CTC AGC TCC GTC GAA CCG AAT TTG CAA       1872
Ala Leu Thr Gln Thr Gly Arg Leu Ser Ser Val Glu Pro Asn Leu Gln
            610                 615                 620

AAC ATT CCG ATT CGG CTT GAG GAA GGG CGG AAA ATC CGC CAG GCG TTC       1920
Asn Ile Pro Ile Arg Leu Glu Glu Gly Arg Lys Ile Arg Gln Ala Phe
625                 630                 635                 640

GTG CCG TCG GAG CCG GAC TGG CTC ATC TTT GCG GCC GAC TAT TCG CAA       1968
Val Pro Ser Glu Pro Asp Trp Leu Ile Phe Ala Ala Asp Tyr Ser Gln
            645                 650                 655

ATC GAG CTG CGC GTC CTC GCC CAT ATC GCG GAA GAT GAC AAT TTG ATT       2016
Ile Glu Leu Arg Val Leu Ala His Ile Ala Glu Asp Asp Asn Leu Ile
            660                 665                 670

GAA GCG TTC CGG CGC GGG TTG GAC ATC CAT ACG AAA ACA GCC ATG GAC       2064
Glu Ala Phe Arg Arg Gly Leu Asp Ile His Thr Lys Thr Ala Met Asp
            675                 680                 685

ATT TTC CAT GTG AGC GAA GAA GAC GTG ACA GCC AAC ATG CGC CGC CAA       2112
Ile Phe His Val Ser Glu Glu Asp Val Thr Ala Asn Met Arg Arg Gln
            690                 695                 700

GCG AAG GCC GTC AAT TTT GGC ATC GTG TAC GGC ATT AGT GAT TAC GGT       2160
Ala Lys Ala Val Asn Phe Gly Ile Val Tyr Gly Ile Ser Asp Tyr Gly
705                 710                 715                 720

CTG GCG CAA AAC TTG AAC ATT ACG CGC AAA GAA GCG GCT GAA TTT ATT       2208
Leu Ala Gln Asn Leu Asn Ile Thr Arg Lys Glu Ala Ala Glu Phe Ile
            725                 730                 735

GAG CGA TAT TTT GCC AGT TTT CCA GGT GTA AAG CAA TAT ATG GAC AAC       2256
Glu Arg Tyr Phe Ala Ser Phe Pro Gly Val Lys Gln Tyr Met Asp Asn
            740                 745                 750

ATT GTG CAA GAA GCG AAA CAA AAA GGG TAT GTG ACG ACG CTG CTG CAT       2304
Ile Val Gln Glu Ala Lys Gln Lys Gly Tyr Val Thr Thr Leu Leu His
            755                 760                 765

CGG CGC CGC TAT TTG CCC GAT ATT ACA AGC CGC AAC TTC AAC GTC CGC       2352
Arg Arg Arg Tyr Leu Pro Asp Ile Thr Ser Arg Asn Phe Asn Val Arg
            770                 775                 780

AGC TTC GCC GAG CGG ACG GCG ATG AAC ACA CCG ATC CAA GGG AGT GCC       2400
Ser Phe Ala Glu Arg Thr Ala Met Asn Thr Pro Ile Gln Gly Ser Ala
785                 790                 795                 800

GCT GAT ATT ATT AAA AAA GCG ATG ATC GAT CTA AGC GTG AGG CTG CGC       2448
Ala Asp Ile Ile Lys Lys Ala Met Ile Asp Leu Ser Val Arg Leu Arg
            805                 810                 815
```

```
GAA GAA CGG CTG CAG GCG CGC CTG TTG CTG CAA GTG CAT GAC GAA CTC      2496
Glu Glu Arg Leu Gln Ala Arg Leu Leu Leu Gln Val His Asp Glu Leu
            820                 825                 830

ATT TTG GAG GCG CCG AAA GAG GAA ATC GAG CGG CTG TGC CGC CTC GTT      2544
Ile Leu Glu Ala Pro Lys Glu Glu Ile Glu Arg Leu Cys Arg Leu Val
        835                 840                 845

CCA GAG GTG ATG GAG CAA GCC GTC GCA CTC CGC GTG CCG CTG AAA GTC      2592
Pro Glu Val Met Glu Gln Ala Val Ala Leu Arg Val Pro Leu Lys Val
    850                 855                 860

GAT TAC CAT TAC GGT CCG ACG TGG TAC GAC GCC AAA TAA                  2631
Asp Tyr His Tyr Gly Pro Thr Trp Tyr Asp Ala Lys
865                 870                 875
```

(2) INFORMATION FOR SEQ ID NO:34:

(i) SEQUENCE CHARACTERISTICS:
        (A) LENGTH: 876 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:34:

```
Leu Lys Asn Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45

Glu Gln Pro Thr His Ile Leu Val Ala Phe Asp Ala Gly Lys Thr Thr
        50                  55                  60

Phe Arg His Glu Thr Phe Gln Asp Ala Lys Gly Gly Arg Gln Gln Thr
65                  70                  75                  80

Pro Pro Glu Leu Ser Glu Gln Phe Pro Leu Leu Arg Glu Leu Leu Lys
                85                  90                  95

Ala Tyr Arg Ile Pro Ala Tyr Glu Leu Asp His Tyr Glu Ala Asp Asp
                100                 105                 110

Ile Ile Gly Thr Met Ala Ala Arg Ala Glu Arg Glu Gly Phe Ala Val
            115                 120                 125

Lys Val Ile Ser Gly Asp Arg Asp Leu Thr Gln Leu Ala Ser Pro Gln
        130                 135                 140

Val Thr Val Glu Ile Thr Lys Lys Gly Ile Thr Asp Ile Glu Ser Tyr
145                 150                 155                 160

Thr Pro Glu Thr Val Val Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Ile Lys Gly Glu
        210                 215                 220
```

-continued

| | | | | | | | | | | | |
|---|---|---|---|---|---|---|---|---|---|---|---|
|Lys|Leu|Lys|Glu|Asn|Leu|Arg|Gln|Tyr|Arg|Asp|Leu|Ala|Leu|Leu|Ser
225| | | | |230| | | | |235| | | | |240

Lys Gln Leu Ala Ala Ile Cys Arg Asp Ala Pro Val Glu Leu Thr Leu
245 250 255

Asp Asp Ile Val Tyr Lys Gly Glu Asp Arg Glu Lys Val Val Ala Leu
260 265 270

Phe Gln Glu Leu Gly Phe Gln Ser Phe Leu Asp Lys Met Ala Val Gln
275 280 285

Thr Asp Glu Gly Glu Lys Pro Leu Ala Gly Met Asp Phe Ala Ile Ala
290 295 300

Asp Ser Val Thr Asp Glu Met Leu Ala Asp Lys Ala Ala Leu Val Val
305 310 315 320

Glu Val Val Gly Asp Asn Tyr His His Ala Pro Ile Val Gly Ile Ala
325 330 335

Leu Ala Asn Glu Arg Gly Arg Phe Phe Leu Arg Pro Glu Thr Ala Leu
340 345 350

Ala Asp Pro Lys Phe Leu Ala Trp Leu Gly Asp Glu Thr Lys Lys Lys
355 360 365

Thr Met Phe Asp Ser Lys Arg Ala Ala Val Ala Leu Lys Trp Lys Gly
370 375 380

Ile Glu Leu Arg Gly Val Val Phe Asp Leu Leu Leu Ala Ala Tyr Leu
385 390 395 400

Leu Asp Pro Ala Gln Ala Ala Gly Asp Val Ala Ala Val Ala Lys Met
405 410 415

His Gln Tyr Glu Ala Val Arg Ser Asp Glu Ala Val Tyr Gly Lys Gly
420 425 430

Ala Lys Arg Thr Val Pro Asp Glu Pro Thr Leu Ala Glu His Leu Ala
435 440 445

Arg Lys Ala Ala Ala Ile Trp Ala Leu Glu Glu Pro Leu Met Asp Glu
450 455 460

Leu Arg Arg Asn Glu Gln Asp Arg Leu Leu Thr Glu Leu Glu Gln Pro
465 470 475 480

Leu Ala Gly Ile Leu Ala Asn Met Glu Phe Thr Gly Val Lys Val Asp
485 490 495

Thr Lys Arg Leu Glu Gln Met Gly Ala Glu Leu Thr Glu Gln Leu Gln
500 505 510

Ala Val Glu Arg Arg Ile Tyr Glu Leu Ala Gly Gln Glu Phe Asn Ile
515 520 525

Asn Ser Pro Lys Gln Leu Gly Thr Val Leu Phe Asp Lys Leu Gln Leu
530 535 540

Pro Val Leu Lys Lys Thr Lys Thr Gly Tyr Ser Thr Ser Ala Asp Val
545 550 555 560

Leu Glu Lys Leu Ala Pro His His Glu Ile Val Glu His Ile Leu His
565 570 575

Tyr Arg Gln Leu Gly Lys Leu Gln Ser Thr Tyr Ile Glu Gly Leu Leu
580 585 590

Lys Val Val His Pro Val Thr Gly Lys Val His Thr Met Phe Asn Gln
595 600 605

Ala Leu Thr Gln Thr Gly Arg Leu Ser Ser Val Glu Pro Asn Leu Gln
610 615 620

Asn Ile Pro Ile Arg Leu Glu Glu Gly Arg Lys Ile Arg Gln Ala Phe
625 630 635 640

-continued

```
Val Pro Ser Glu Pro Asp Trp Leu Ile Phe Ala Ala Asp Tyr Ser Gln
            645                 650                 655

Ile Glu Leu Arg Val Leu Ala His Ile Ala Glu Asp Asp Asn Leu Ile
            660                 665                 670

Glu Ala Phe Arg Arg Gly Leu Asp Ile His Thr Lys Thr Ala Met Asp
            675                 680                 685

Ile Phe His Val Ser Glu Glu Asp Val Thr Ala Asn Met Arg Arg Gln
    690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
    770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
            805                 810                 815

Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
            835                 840                 845

Pro Glu Val Met Glu Gln Ala Val Ala Leu Arg Val Pro Leu Lys Val
    850                 855                 860

Asp Tyr His Tyr Gly Pro Thr Trp Tyr Asp Ala Lys
865                 870                 875
```

PURIFIED DNA POLYMERASE FROM *BACILLUS STEAROTHERMOPHILUS*

This application is a divisional of U.S. Ser. No. 08/436,664, filed May 8, 1995, now U.S. Pat. No. 5,874,282, which is a divisional of U.S. Ser. No. 08/394,232, filed Feb. 24, 1995, which is a continuation in part of U.S. Ser. No. 08/307,410, filed Sep. 16, 1994, now abandoned, which is a continuation in part of U.S. Ser. No. 08/222,612, filed Apr. 1, 1994, now abandoned.

FIELD OF THE INVENTION

The invention relates to purified thermostable DNA polymerase enzymes derived from the Gram-positive bacterium *Bacillus stearothermophilus*. These enzymes are useful in biochemical procedures requiring the template-directed synthesis of a nucleic acid strand, such as sequencing and nucleic acid amplification procedures. The invention also relates to methods of making and using these enzymes.

BACKGROUND OF THE INVENTION

DNA polymerase enzymes are naturally-occurring intracellular enzymes, and are used by a cell to replicate a nucleic acid strand using a template molecule to manufacture a complementary nucleic acid strand. Enzymes having DNA polymerase activity catalyze the formation of a bond between the 3' hydroxyl group at the growing end of a nucleic acid primer and the 5' phosphate group of a nucleotide triphosphate. These nucleotide triphosphates are usually selected from deoxyadenosine triphosphate (A), deoxythymidine triphosphate (T), deoxycytidine triphosphate (C) and deoxyguanosine triphosphate (G). However, DNA polymerases may incorporate modified or altered versions of these nucleotides. The order in which the nucleotides are added is dictated by base pairing to a DNA template strand; such base pairing is accomplished through "canonical" hydrogen-bonding (hydrogen-bonding between A and T nucleotides and G and C nucleotides of opposing DNA strands), although non-canonical base pairing, such as G:U base pairing, is known in the art. See e.g., Adams et al., *The Biochemistry of the Nucleic Acids* 14–32 (11th ed. 1992).

The in-vitro use of enzymes having DNA polymerase activity has in recent years become more common in a variety of biochemical applications including cDNA synthesis and DNA sequencing reactions (see Sambrook et al., (2nd ed. Cold Spring Harbor Laboratory Press, 1989) hereby incorporated by reference herein), and amplification of nucleic acids by methods such as the polymerase chain reaction (PCR) (Mullis et al., U.S. Pat. Nos. 4,683,195, 4,683,202, and 4,800,159, hereby incorporated by reference herein) and RNA transcription-mediated amplification methods (e.g., Kacian et al., PCT Publication No. WO91/01384 which enjoys common ownership with the present application and is hereby incorporated by reference herein).

Methods such as PCR make use of cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37° C. to 42° C. (thermostable DNA polymerase enzymes) provides an advantage in cost and labor efficiency. Thermostable DNA polymerases have been discovered in a number of thermophilic organisms including, but not limited to *Thermus aquaticus*, *Thermus thermophilus*, and species of the Bacillus. Thermococcus, Sulfobus, Pyrococcus genera.

DNA polymerases can be purified directly from these thermophilic organisms. However, substantial increases in the yield of DNA polymerase can be obtained by first cloning the gene encoding the enzyme in a multicopy expression vector by recombinant DNA technology methods, inserting the vector into a host cell strain capable of expressing the enzyme, culturing the vector-containing host cells, then extracting the DNA polymerase from a host cell strain which has expressed the enzyme.

The bacterial DNA polymerases that have been characterized to date have certain patterns of similarities and differences which has led some to divide these enzymes into two groups: those whose genes contain introns—intervening non-coding nucleotide sequences—(Class B DNA polymerases), and those whose DNA polymerase genes are roughly similar to that of *E. coli* DNA polymerase I and do not contain introns (Class A DNA polymerases).

By "non-coding" is meant that the nucleotides comprising both nucleic acid strands in such sequences do not contain 3-nucleotide codons that encode and correspond to amino acid residues of the mature protein. Introns are most often found in the genes of eukaryotic higher organisms but have also been found in lower organisms such as archaebacteria.

Several Class A and Class B thermostable DNA polymerases derived from thermophilic organisms have been cloned and expressed. Among the class A enzymes: Lawyer, et al., *J. Biol. Chem.* 264:6427–6437 (1989) and Gelfund et al., U.S. Pat. No. 5,079,352, report the cloning and expression of a full length thermostable DNA polymerase derived from *Thermus aquaticus* (Taq). Lawyer et al., in *PCR Methods and Applications*, 2:275–287 (1993), and Barnes, PCT Publication No. WO92/06188 (1992), disclose the cloning and expression of truncated versions of the same DNA polymerase, while Sullivan, EPO Publication No. 0482714A1 (1992), reports cloning a mutated version of the Taq DNA polymerase. Asakura et al., *J. Ferment. Bioeng.* (Japan), 74:265–269 (1993) have reportedly cloned and expressed a DNA polymerase from *Thermus thermophilus*. Gelfund et al., PCT Publication No. WO92/06202 (1992), have disclosed a purified thermostable DNA polymerase from *Thermosipho africanus*. A thermostable DNA polymerase from *Thermus flavus* was reported by Akhmetzjanov and Vakhitov, *Nucleic Acids Res.*, 20:5839 (1992). Uemori et al., *J. Biochem.* 113:401–410 (1993) and EPO Publication No. 0517418A2 (1992) have reported cloning and expressing a DNA polymerase from the thermophilic bacterium *Bacillus caldotenax*. Ishino et al., Japanese Patent Application No. HEI 4[1992]-131400 (publication date Nov. 19, 1993) report cloning a DNA polymerase from *Bacillus stearothermophilus*.

Among the Class B enzymes: A recombinant thermostable DNA polymerase from *Thermococcus litoralis* was reported by Comb et al., EPO Publication No. 0 455 430 A3 (1991), Comb et al., EPO Publication No. 0547920A2 (1993), and Perler et al., *Proc. Natl. Acad. Sci.* (USA), 89:5577–5581 (1992). A cloned thermostable DNA polymerase from *Sulfolobus solofatarius* is disclosed in Pisani et al., *Nucleic Acids Res.* 20:2711–2716 (1992) and in PCT Publication WO93/25691 (1993). The thermostable enzyme of *Pyrococcus furiosus* is disclosed in Uemori et al., *Nucleic Acids Res.*, 21:259–265 (1993), while a recombinant DNA polymerase was derived from Pyrococcus sp., as disclosed in Comb et al., EPO Publication No. 0547359A1 (1993).

By "thermostable" is meant that the enzyme remains has an optimal temperature of activity at a temperature greater than about 37° C. to 42° C. Preferrably, the enzymes of the present invention have an optimal temperature for activity of between about 50° C. and 75° C.; most preferably between 55° C. and 70° C., and most preferably between 60° C. and 65° C.

Many thermostable DNA polymerases possess activities additional to a DNA polymerase activity; these may include a 5'-3' exonuclease activity and/or a 3'-5' exonuclease activity. The activities of 5'-3' and 3'-5' exonucleases are well known to those of ordinary skill in the art. The 3'-5' exonuclease activity improves the accuracy of the newly-synthesized strand by removing incorrect bases that may have been incorporated; DNA polymerases in which such activity is low or absent, reportedly including Taq DNA polymerase, (see Lawyer et al., *J. Biol Chem.* 264:6427–6437), are prone to errors in the incorporation of nucleotide residues into the primer extension strand. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is is a desired characteristic of a thermostable DNA polymerase used for such purposes.

By contrast, the 5'-3' exonuclease activity often present in DNA polymerase enzymes is often undesired in a particular application since it may digest nucleic acids, including primers, that have an unprotected 5' end. Thus, a thermostable DNA polymerase with an attenuated 5'-3' exonuclease activity, or in which such activity is absent, is also a desired characteristic of an enzyme for biochemical applications. Various DNA polymerase enzymes have been described where a modification has been introduced in a DNA polymerase which accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, supra, and Gelfund et al., U.S. Pat. No. 5,079,352 have produced 5'-3' exonuclease-deficient recombinant Taq DNA polymerases. Ishino et al., EPO Publication No. 0517418A2, have produced a 5'-3' exonuclease-deficient DNA polymerase derived from *Bacillus caldotenax*.

Preparation of antisera or moloclonal antibodies to particular DNA polymerase enzymes has been described and is well known in the art. For example, Hu et al., *J. Virol.* 60:267–274 (1986) report specific immunoprecipiation of cloned reverse transcriptase and fusion proteins from Moloney Murine Leukemia Virus expressed in *E. coli* by recovering PAGE-separated MMLV reverse transcriptase from the gel, immunizing rabbits with the purified protein, and recovering the antisera. Livingston et al., *Virology* 50:388–395 (1972) disclose affinity chromatography of Avian Type C Viral transcriptase using antibodies able to differentiate between viral and host cell DNA polymerases. Spadari and Weissbach, *J. Biol. Chem.* 249:5809–5815 (1974) report that HeLa-derived DNA polymerase is not inhibited by antisera prepared against reverse transcriptases obtained from either the Mason-Pfizer monkey virus, the Wooley monkey virus, or the Rauscher murine leukemia virus. These publications are hereby incorporated herein by reference.

SUMMARY OF THE INVENTION

The present invention provides recombinant and/or purified thermostable DNA polymerase enzymes from *Bacillus stearothermophilus* (Bst). One or more of the enzymes of the present invention may be produced and purified from a culture of *Bacillus stearothermophilus* or the genes encoding these enzymes may be cloned into a suitable expression vector, expressed in a heterologous host and purified. Among the DNA polymerase enzymes disclosed herein are mutated or truncated forms of the native enzyme which contain deletions in the 5'-3' exonuclease domain of the enzyme and/or its corresonding gene.

These enzymes may be used in nucleic acid amplification methods and other biochemical protocols that require a DNA polymerase activity. Furthermore, because the enzymes provided herein are thermostable, they are suitable for use in biochemical applications using higher temperatures than many other DNA polymerase enzymes, such as the Klenow fragment from *E. coli* DNA polymerase I. As permitted by the particular biochemical application, the enzymes provided herein may be used in an unpurified form. Alternatively, these enzymes may be purified prior to use.

Accordingly, the present invention also provides methods for the purification and use of Bst DNA polymerase enzymes. A preferred method of purification of the Bst DNA polymerases comprises two anion-exchange steps and phosphocellulose chromatography. Preferred chromatography conditions are described herein. However, it will be appreciated that variation of these conditions or their order would be apparent to one of skill in the art in light of the present disclosure.

Additionally, the present invention provides compositions comprising DNA fragments containing the genes encoding the enzymes of the present invention, vectors containing these genes, and methods of producing these recombinant enzymes.

The invention also encompasses a stable enzyme formulation comprising one or more of the DNA polymerase enzymes of the present invention in a buffer containing stabilizing agents.

Both the full length Bst polymerase enzyme and the variants thereof described and claimed herein may be cloned as a single uninterrupted gene on a multicopy vector in an *E. coli* host strain without being lethal to the host cell or under the control of a strong repressor. Moreover, the Bst polymerases may be expressed constitutively within the *E. coli* host cell; inducible expression of these enzymes, while possible, is not necessary to obtain a high yield of active enzyme.

BRIEF DESCRIPTION OF THE DRAWINGS

FIG. 1 shows the nucleotide sequences of the oligonucleotides used as primers and probes in the present invention.

FIG. 5 is a schematic diagram of the results of Southern blot experiments with various labeled probes.

FIGS. 8A and 8B is a representation of the strategy for the construction of plasmid pUC Bst 1.

FIG. 12 shows the N-terminal amino acid residues of various "Klenow-like" Bst polymerase enzymes.

DESCRIPTION OF THE PREFERRED EMBODIMENTS

Figure 2:
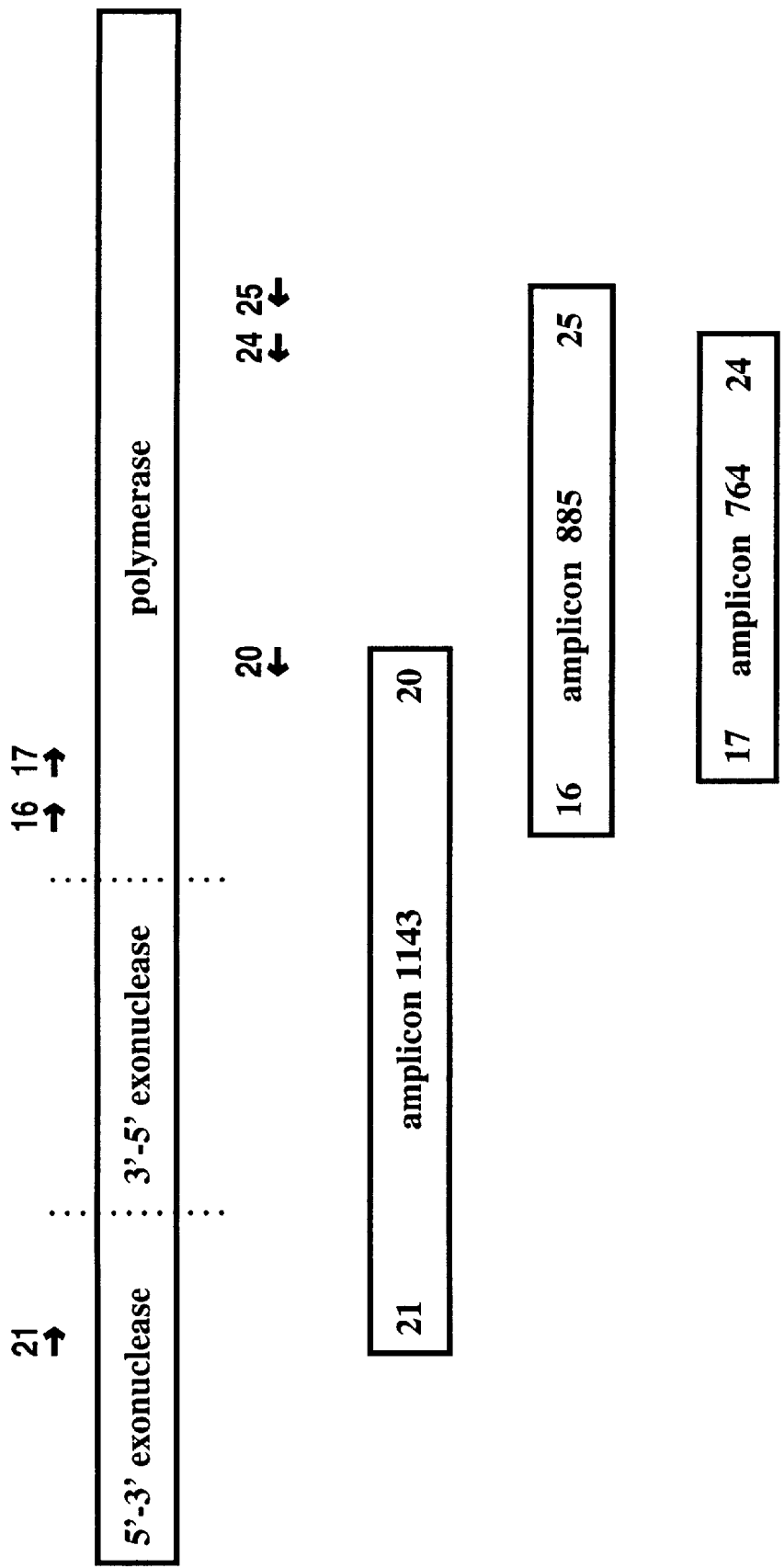
FIG. 2 is a graphical representation of the Bst polymerase gene, the location of nucleotide sequences therein complementary to the probes and PCR primers used in generating Bst amplicons, and the location with respect to the Bst gene of the amplicons so generated.

The present invention relates to purified DNA polymerase enzymes derived from *Bacillus stearothermophilus*, DNA fragments encoding said enzymes for expression in a heterologous host cell, and methods of their production, purification and use. These enzymes are useful in biochemical applications, such as nucleic acid sequencing and amplification, including transcription based amplification systems. Preferably, the enzymes of the present invention are optimally active at temperatures above about 37° C. to 42° C., and are thus suitable for biochemical applications that require a relatively high temperature of reaction. Most preferably, the enzymes of the present invention are optimally active at a temperature of about 60° C. to 65° C.

The enzymes of the present invention have an amino acid sequence that bears some resemblance to DNA polymerase enzymes of the Class A designation, of which the nonthermostable *E. coli* DNA polymerase I is a member. A comparision of the amino acid sequences of the Class A DNA polymerases reveals regions of relative sequence homology seperated by a number of reasonably well-defined "variable" regions. By variable regions is meant that a comparison of the amino acid sequences in these regions reveals that about 10% or more of the contiguous amino acid residues within a given region of the compared DNA polymerase sequences are different. For this purpose, a region is defined as 20 or more contiguous amino acid residues.

Likewise, a comparison of the nucleotide sequences of the genes encoding the Class A DNA polymerases reveal regions in which the nucleotide sequences are highly conserved between species, and other, variable regions. Because of the degeneracy of the genetic code, the amount of nucleotide sequence variability may be greater than the amount of amino acid variability between the corresponding proteins expressed as a percentage. Alternatively, because each amino acid is encoded by three nucleotide residues and a change in one of them may result in a codon corresponding to a different amino acid, the amount of nucleotide sequence variability in the genes encoding these enzymes may be less than that of the corresponding amino acid sequence on a percentage basis.

Expression of recombinant proteins in RNase-deficient cells and the use of tetracycline-resistance as a selectable marker gene have been described in published European Patent Application 688,870.

Definitions

As used herein the following terms have the indicated meanings unless expressly indicated otherwise.

By "selectable marker gene" is meant a DNA fragment encoding a gene which, when carried and expressed by a host cell, is capable of conferring a growth advantage to that host cell as compared to cells not containing the selectable marker gene when both are grown in a culture media of a given composition. For example, the gene encoding β-lactamase will confer resistance to ampicillin on host cells containing this gene, whereas cells not containing the gene will be sensitive to ampicillin; thus only cells expressing the gene for β-lactamase will grow in media containing ampicillin. Similarly, cells unable to synthesize an essential amino acid will not grow in media not containing that amino acid, whereas cells containing a gene allowing the cell to make the essential amino acid will grow in the same media.

A selectable marker gene may be covalently linked, for example in a plasmid or expression vector, to one or more other gene or genetic element as a means of identifying cells containing both the selectable gene and the "silent" gene(s) and/or genetic element(s).

By a "purified" nucleic acid or protein is meant a nucleic acid or protein subjected to at least one step which removes cellular components such as carbohydrates, lipids, unwanted nucleic acids, or unwanted proteins from the indicated nucleic acid or protein.

By "upstream" is meant to the 5' side of a given locus on a nucleic acid strand, or in the case of a double stranded nucleic acid molecule, to the 5' side of a particular locus with respect to the direction of gene transcription in that region of the nucleic acid molecule.

By "downstream" is meant to the 3' side of a given locus on a nucleic acid strand, or in the case of a double stranded nucleic acid molecule, to the 3' side of a particular locus with respect to the direction of gene transcription in that region of the nucleic acid molecule.

By "$T_m$" is meant the temperature at which 50% of a population of a double-stranded nucleic acid molecules, or nucleic acid molecules having a double-stranded region, become single-stranded or thermally denatured.

By "recombinant" is meant that a nucleic acid molecule or protein is at least partially the result of in vitro biochemical techniques. A "recombinant DNA molecule" is thus a non-naturally occurring molecule. Such recombinant molecules include, but are not limited to molecules which comprise restriction endonuclease fragments, in vitro nucleic acid ligation products, in vitro exonuclease fragments, and expression vectors comprising heterologous genetic elements such as one or more of the following: promoters, repressor genes, selectable marker genes, temperature-sensitive DNA replication elements, structural genes, and the like.

"Recombinant" proteins or enzymes are those not found in nature These include purified protein preparations and proteins produced from recombinant DNA molecules. The latter proteins are usually expressed in a heterologous host cell, i.e., one not native to the protein or enzyme in question. However, the gene encoding a recombinant protein may reside on an expression vector contained within a host cell of the same species as the organism from which the protein in question was derived.

By "truncated" is meant a smaller version of the gene or protein in question; with respect to the primary nucleotide or amino acid sequence, a truncated form of a reference nucleic acid or protein is one that lacks one or more nucleotides or amino acids as compared to the reference molecule.

By "substantial sequence homology" is meant that a first nucleic acid or protein molecule has a recognizably non-random similarity to a second reference nucleic acid or protein over at least about 89% of its nucleotide or amino acid sequence respectively.

By a nucleic acid or protein "domain" is meant at least one definite region of contiguous nucleotide or amino acid residues.

By "origin of replication" is meant a specific region of DNA at which primer production and initiation of DNA polymerase activity begins. In this specification, the term is used to mean a nucleic acid element present on a DNA expression vector that allows the expression vector to increase in copy number within a given host cell.

By "promoter" is meant a genetic element comprising a specific region of DNA at which an RNA polymerase enzyme can bind and begin transcription of a DNA template, thus providing the first step of translating the genetic information contained in the sequence of a nucleic acid into the production of a protein of an amino acid sequence corresponding to that nucleic acid sequence.

By "expression", "gene expression" or "protein express" is meant the production of protein from information contained within a gene by a host organism.

By "transformation" is meant a biochemical method of inducing a host cell to internalize a nucleic acid molecule. Such nucleic acid molecules are usually genetic elements comprising at least an origin of replication, a selectable marker gene, and a promoter for expression of the selectable marker gene within the host cell.

By "heterologous" is meant not of the same species. Thus, an enzyme expressed in a heterologous host cell is produced in a host cell of a different species than the one from which the enzyme was originally derived.

By "gene" is meant a nucleic acid region having a nucleotide sequence that encodes an expressible protein or polypeptide. A gene may comprise one or more "coding sequences" containing codons that correspond to amino acid residues of the expressed protein; the gene may also comprise, but need not comprise, one or more "non-coding" nucleotide sequence regions that do not contain codons corresponding to amino acid residues of the expressed protein.

Materials and Methods

Sources of Bacterial Strains, Plasmids and Enzymes

The *Bacillus stearothermophilus* (Bst) ATCC type strain number 12980 was obtained from the American Type Culture Collection, Rockville, Md. Three strains of the bacterium *Escherichia coli* were used as host cells for cloning and expression of the Bst DNA polymerase enzymes of the present invention: *E. coli* strains XL1-Blue MRF' and JM109 were obtained from Stratagene Cloning Systems (San Diego, Calif.), and *E. coli* strain 1200 (CGSC strain #4449) was obtained from the *E. coli* Genetic Stock Center (Yale University, New Haven, Conn.).

Plasmid vector pUC 18 was obtained from Life Technologies Inc. (Gaithersburg, Md.), and vector pGem 3Z was obtained from Promega Corp. (Madison, Wis.). All restriction endonucleases and nucleic acid modifying enzymes, such as T4 DNA ligases, the Klenow fragment from *E. coli* DNA polymerase I, thermostable DNA polymerase, and polynucleotide kinase were obtained from commercial suppliers and were used in accordance with the manufaturer's instructions unless stated otherwise.

Bacterial cultures

*Bacillus stearothermophilus* and *E. coli* cultures were grown in 1% (w/v) tryptone, 0.5% (w/v) yeast extract and 0.5% (w/v) sodium chloride (LB broth) or on Petri plates of the same solution containing 1.3% (w/v) agar (LB agar). When required and as indicated in the following disclosure, ampicillin was used at a concentration of 100 $\mu$g/ml, tetracycline at a concentration of 12 $\mu$g/ml, isopropylthio-$\beta$-galactoside (IPTG) at a concentration of 0.5 mM, and 5-bromo-4-chloro-3-indolyl-$\beta$-D-galactoside (X-gal) at 50 $\mu$g/ml. *B. stearothermophilus* cultures were incubated at 55° C. and *E. coli* cultures were incubated at 37° C., both with shaking to aerate.

DNA preparations

Plasmid DNA preparations were done by one of two methods as indicated in the following disclosure. The first is a standard boiling method for plasmid minipreparations as described in Sambrook et al., supra at page 1.29, previously incorporated by reference herein. The second method utilized the Qiagen Plasmid Kit available from Qiagen Inc. (Chatsworth, Calif.) which was used for preparing purified DNA. This method makes use of a proprietary anion exchange resin and a series of proprietary elution buffers to prepare plasmid DNA without the need for CsCl gradients. The method is described in the *Oiagen Plasmid Handbook for Plasmid Midi Kit and Plasmid Maxi Kit* ©1992 Diagen GmbH, Qiagen, Inc. For preparations of *B. stearothermophilus* genomic DNA, overnight cultures of cells were centrifuged and the pellet was resuspended in 1/50 the original volume of 10 mM Tris-HCl, 100 mM NaCl and 5 mM ethylenediamine tetraacetic acid (EDTA) (pH 7.0). Lysozyme was added to a final concentration of 2 mg/ml, and the suspension was incubated at 37° C. for 20 minutes. Nine volumes of a solution containing 10 mM Tris-Cl (pH 8.0), 250 mM NaCl, 1.2% (v/v) Triton X-100, 100 $\mu$g/ml RNase A, 12 mM EDTA and 0.5M guanidine-HCl were added to the cell suspension and the mixture was incubated on ice for 20 minutes. The mixture was made 2 mg/ml in proteinase K and incubated at 50° C. for 2 hours with gentle shaking. The solution was then centrifuged at 15–20,000×g for 10 minutes and the supernatant decanted off. Bst genomic DNA was then prepared using a variation of the Qiagen method described above for the recovery of plasmid DNA; other methods of preparing genomic DNA from cleared cell lysates are well known to those of ordinary skill in the art.

Probe labeling

Single-stranded DNA oligomer probes were labeled by one of two methods as indicated in the following disclosure. The first method was by utilizing T4 polynucleotide kinase to label the 5' end of an oligonucleotide with radioactive $^{32}$P, as exemplified in Sambrook et al., supra, at page 10.60, previously incorporated by reference. Other methods of labeling probes with radioactive atoms are well known to those of ordinary skill in the art. This protocol was used to label oligonucleotides 16, 24 and 25. The second labeling method utilized was the LIGHTSMITH™ chemiluminescent system (high stringency) obtained from Promega Corp., which was used to label oligonucleotides 15, 21 and 20 (SEQ ID NO:13, SEQ ID NO:9 and SEQ ID NO:11, respectively). This method makes use of non-radioactive labels and is thus generally more I convenient than using $^{32}$P or other radionuclides for detection. However, oligonucleotides 15, 20 and 21 may easily be labelled with radioactive atoms as described above with no loss in detection ability.

Gel electrophoresis and gel isolation of DNA fragments

Unless indicated otherwise, agarose gels were 1% (w/v) agarose (Life Technologies Inc.). The agarose gels were run in 1× TAE buffer (40 mM Tris base (pH 8.0), 20 mM sodium acetate, 2 mM EDTA) containing 2 $\mu$g/ml ethidium bromide.

To gel purify DNA fragments, agarose gel slices containing the desired fragments were excised and frozen on dry ice. The gel slices were then thawed, crushed and extracted with TAE-saturated phenol. Following a brief centrifugation, the aqueous phases were collected and extracted with a solution of 50% (v/v) TE-(10 mM Tris (pH 8.0) and 1 mM EDTA) saturated phenol, 49% (v/v) chloroform and 1% (v/v/) isoamyl alcohol. This was followed by extraction of the aqueous phase with a solution of 24:1 (v/v) chloroform:isoamyl alcohol. To ethanol precipitate the nucleic acids, the aqueous phases were then collected, given 1/10 volume of 3M sodium acetate and 2½ volumes of ethanol, and centrifuged. The pellets were dissolved in an appropriate volume of TAE buffer.

Southern blot, hybridization, wash and detection methods

DNA fragments were separated on 1% (w/v) agarose gels and transferred by capillary action in 20× SSC (3M sodium chloride, 0.3M sodium citrate) to Nytran (+) nylon membranes (Schleicher & Schuell, Inc., Keene, N.H.) by the method of Southern as described in Sambrook et al., supra, at page 9.38, previously incorporated by reference herein. The membranes were air dried and baked at 80° C. in a vacuum oven for 2 hours prior to hybridization.

Membranes to be hybridized with the $^{32}$P labeled probes were first pre-hybridized at 37° C. for approximately 2 hours in 6× SSPE (20× SSPE=3.0M NaCl, 0.2M NaH$_2$PO$_4$ (pH 7.4), 0.02M EDTA) (Life Technologies Inc.), 5× Denhardt's solution (0.1% (w/v) of each of the following: bovine serum albumin, ficoll and polyvinylpyrrolidone), 1% (w/v) SDS (sodium dodecyl sulfate), 100 µg/ml sonicated denatured salmon sperm DNA and formamide (25% (v/v) for oligomer 16 and 20% (v/v) for oligomers 24 and 25). The membranes were then incubated overnight at 37° C. in a hybridization solution made as above except with 1× (rather than 5×) Denhardt's solution and with the addition of 1×10$^6$ counts per minute (CPM)/ml of the labeled probe. The membranes were then sequentially washed at room temperature in aqueous solutions of 5× SSC and 0.1% SDS, 1× SSC and 0.5% SDS, and 0.2× SSC and 0.5% SDS. Membranes incubated with labeled oligonucleotides 24 and 25 were additionally washed with a solution of 0.1× SSC and 0.1% (w/v) SDS. Following the wash steps, the membranes were dried and allowed to expose X-ray film using intensifier screens at −80° C. for 3 hours.

Membranes to be hybridized with oligomers 15, 21 and 20 were processed according to the manufacturer's "high stringency" protocol (Promega, Inc.). As stated above, the use of chemiluminescent probes was for convenience only; had the probes been $^{32}$P labelled, the Southern hybridization procedure could have been performed as described above. The hybridization and wash temperatures used were 56° C. for oligomer 15, 48° C. for oligomer 21 and 51° C. for oligomer 20.

Sequencing reactions

Plasmid DNA preparations of clones pGem Bst 2.1 Sst and pGem Bst 5' end were used as the templates for sequencing the Bst DNA polymerase gene using the dideoxy chain-termination method. See e.g., Sanger et al., *Proc. Nat. Acad. Sci.* (USA) 74:5463–5467 (1977) hereby incorporated by reference herein. Four µg of DNA were used with 1 pmol of primer in each reaction. Sequencing was done using a Sequenase™ kit (version 2.0) obtained from United States Biochemical Co. according to the manufacturer's protocol. In regions of the nucleic acid strand which were difficult to sequence a variety of techniques known to those of skill in the art were used to minimize inter- and intramolecular reannealing in the sequencing reactions and the polyacrylamide gel. The most successful technique for resolving hard to read regions of the nucleotide sequences was the inclusion of 40% (v/v) formamide in the sequencing gel. Variations of the dideoxy sequencing method are well known to those of ordinary skill in the art, as are other nucleic acid sequencing methods =-such as the method of Maxam and Gilbert, *Methods in Enzymology* 65:497–559 (1980) hereby incorporated by reference herein.

Bst DNA polymerase activity assays

Bst DNA polymerase activity was determined by a cDNA synthesis reaction using a synthetic single-stranded template and primer complementary to a portion of the template. Detection of the cDNA strand was accomplished by hybridizing the polymerase product with an acridinium ester-labeled probe designed to be complementary to the cDNA strand. The labeled double-stranded hybrid was detected using the hybridization protection assay (HPA) as described in Arnold et al., *Clin. Chem.* 35:1588–1594 (1989) and Arnold et al., U.S. Pat. No. 5,283,174, the latter of which enjoys common ownership with the present application and both of which are hereby incorporated by reference herein. The sample suspected of containing Bst DNA polymerase was incubated in a reaction mixture containing 50 mM Tris (pH 7.5), 25 mM KCl, 4 mM MgCl$_2$, 2 mM spermidine, 0.2 mM each dNTP at 60° C. for 8 minutes with 20 fmol of an 86 base pair synthetic DNA template derived from bacteriophage t7 gene 10 plus 30 pmol of a 23 base primer complementary to the 3' end of the template strand. The reaction mixture was incubated at 95° C. for 3 minutes to denature the DNA strands, then incubated at 60° C. for 10 minutes with 1.5 pmol of the acridinium ester labeled detection probe. Unhybridized probe was hydrolysed at 60° C. for 7 minutes with an alkaline borate buffer and the remaining chemiluminescence, contributed by the hybridized labeled probe, was measured in a LEADER 1™ luminometer, (Gen-Probe Incorporated, San Diego, Calif.), after injection of a dilute solution of H$_2$O$_2$ and a solution of sodium hydroxide.

Primer and probe design

Several DNA polymerase genes have been cloned and sequenced, and alignment of these sequences reveals numerous areas in which the nucleotide sequences of the DNA polymerase genes are somewhat conserved between species. See e.g., Delarue, *Protein Engineering* 3:461–4670 (1990). The published Bca sequence (see Uemori et al., *J. Biochem.* 113:401–410 (1993)) was used as a basis for designing primers and probes to some of these conserved regions using the Bca nucleotide sequence as a starting point; the Bca DNA polymerase nucleotide sequence contained in this publication is hereby incorporated by reference herein. The nucleotide sequences of the primers and probes used in the course of the present invention are shown in FIG. 1. Mismatches between the Bca DNA polymerase sequence and these primers and probes are present in some cases. These primers and probes were purposely designed with mismatches for one of two reasons. First, a mismatch was sometimes designed in order to create a codon, based on an analysis of codon usage in various *B. stearothermophilus* genes encoding proteins of known sequence, thought to be preferred by *B. stearothermophilus* over the codon present in the Bca DNA polymerase gene. The second reason that a mismatch between the Bca DNA polymerase nucleotide sequence and the primers described herein was designed was to better match an interspecies consensus of the nucleotides present in that relative position, as deduced from alignments of other DNA polymerases. Occasionally, a T was used in the Bst primers and probes in place of a C in the Bca DNA polymerase sequence since a G/T mismatch is relatively stable and therefore the oligonucleotides would be better able to hybridize to different targets.

Purification of Bst Polymerase Enzymes

Bacterial host cells containing genes encoding Bst polymerase enzymes were grown in liquid culture for sixteen hours with shaking, as described above. The preferred host cell strain was E. coli strain 1200. After sixteen hours at 37° C., the cell cultures were centrifuged at 9000×g for 10 minutes, and the cell pellets were washed once with 20 mM Tris HCl (pH 7.5) containing 0.1 mM EDTA. Fifty grams of cell pellets were suspended in ten volumes of lysis buffer (25 mM Tris HCl, 10 mM EDTA, 5 mM DTT, 1%(v/v) Triton X-100, 10 mM NaCl, 10%(v/v) glycerol and 1 mM phenylmethylsulfonyl fluoride (PMSF)). The cell suspension was then passed twice through a Gaulin cell homogenizer at 8000 psi to lyse the cells. The cell lysate was then centrifuged at 12,000×g for 15 minutes and the supernatant collected and stored at −70° C.

Chromotography was performed at 25° C. Two hundred fifty ml of the cell lysate was applied to a 190×26 mm column of Poros-HQ anion exchange resin (PerSeptive Biosystems, Cambridge, Mass.) The column was washed with 160 ml of a solution containing 20 mM Tris-HCl (pH 8.0) and 0.1 mM EDTA (Buffer A). The bound proteins were eluted with a 500 ml linear gradient from 0 to 0.5 M NaCl in Buffer A at a flow rate of 5 ml/minute. DNA polymerase activity eluted at an ionic strength corresponding to a salt concentration of between 0.1 and 0.2M NaCl. Ten ml fractions were collected. In some cases, active fractions were pooled and passed through a second Poros-HQ column under similar conditions.

The pooled anion exchange fractions, in a volume of 40 ml, were diluted with 3 volumes of buffer A and applied to a 190×26 mm phosphocellulose P-11 column equilibrated in Buffer A containing 50 mM NaCl. The column was washed with 200 ml of the same buffer. The bound proteins were eluted in a linear gradient of 0.1M to 0.7M NaCl in Buffer A at a flow rate of 3 ml/minute. The DNA polymerase activity eluted from this column at an ionic strength corresponding to a salt concentration of about 0.25–0.30M NaCl. Fractions of 10 ml were collected.

The pooled active fractions from the phosphocellulose step were dialyzed twice against 1 liter of Buffer A at 25° C. and applied to an 250×10 mm SynChropak AX-300 anion exchange HPLC column pre-equilibrated in Buffer A (Rainin Corp., Emeryville, Calif.) at a flow rate of 2.4 ml/minute. Samples were in Buffer A. Bound proteins were eluted with a fifty ml linear gradient from 100 mM to 700 mM NaCl in Buffer A at 2.4 ml/minute. Bst DNA polymerase activity eluted at an ionic strength corresponding to a salt concentration of between about 0.2 and 0.4M NaCl.

In some cases, the purified full-length Bst polymerase was further treated with a protease to generate an active truncated form of the enzyme. In such cases, purified Bst polymerase (0.33 mg/ml) was treated with subtilisin in Buffer A at a 1:200 (w/w) ratio of protease to Bst polymerase at 25° C. The reaction mixture was incubated at 25° C. for 40 minutes, and the reaction was terminated with the addition of PMSF to a final concentration of 1 mM. The active proteolytic fragment of Bst DNA polymerase was purified using a 60×10 mm column of hydroxyapatite (HA) (Bio Gel-HT, BioRad Laboratories, Richmond, Calif.) according to the method of Jacobsen et al., Eur. J. Biochem. 45:623 (1974) the disclosure of which is hereby incorporated by reference herein. The HA column was equilibrated in 20 mM sodium phosphate (pH 7.0), and Bst polymerase was eluted with a linear gradient from 20 to 350 mM sodium phosphate (pH 7.0) at a flow rate of 1 ml/minute. The active protein eluted at an ionic strength corresponding to about 0.3M sodium phosphate. The active fractions were pooled.

Figure 14:
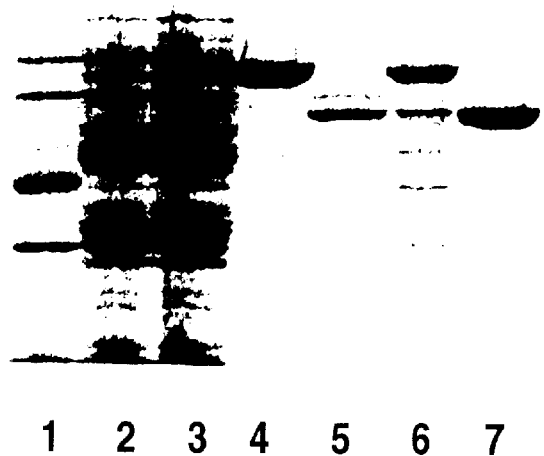
FIG. 14 shows an SDS-PAGE gel of molecular weight markers (lane 1), a negative control cell lysate, (lane 2) a crude cell lysate Bst-1 clone(lane 3) purified (lane 4) Bst 1, a purified subtilisin fragment of Bst 1 (lane 5), partly purified Bst 3 (lane 6), and a purified preparation of a natural cleavage product of Bst 3.

FIG. 14 is a photograph of an SDS-PAGE gel containing a crude bacterial lysate, purified Bst 1, purified Bst 3, a purified preparation of the naturally-occurring breakdown product of Bst 3, and Bst 4 (described further below).

The purification scheme described above resulted in the preparation of highly purified Bst polymerase enzymes as determined by SDS-PAGE followed by staining with Coomassie Brilliant Blue. However, variations based on this scheme or alteration of the order of the steps outlined above will be readily apparent to one of ordinary skill in the art in light of the present specification.

EXAMPLES

The examples which follow are intended to illustrate various embodiments of the present invention in order to allow one of ordinary skill in the art to make and use the methods and compositions of the present invention. However, it will be appreciated that variations in the nucleotide sequences of the nucleic acids described herein or in the amino acid sequences of the proteins described herein, or both, may exist due to variation between different strains of Bacillus stearothermolphilus, or due to spontaneous mutations arising as the result of genetic drift. Furthermore, the nucleotide and/or amino acid sequences disclosed herein may easily be modified by genetic and biochemical techniques to produce derivative proteins having DNA polymerase activities. The resulting protein will have substantially the same amino acid sequence as the Bst polymerase enzymes disclosed herein, and may exhibit a higher or lower level of DNA polymerase activity. The activity of any such derivative may be detected or measured as described above.

Thus, the scope of the present invention is not to be limited solely to the embodiments which follow, said scope to be determined solely by the claims which follow this disclosure.

Example 1

Identification of the Genomic Bst DNA Polymerase Gene

Amplicons 885 and 764

The location of PCR amplicons and primers used to generate these amplicons are shown in FIG. 2 relative to the Bst DNA polymerase gene. The polymerase chain reaction (PCR) is a proprietary method of conducting nucleic acid amplification, and is patented under the following U.S. patents: Mullis et al., U.S. Pat. Nos. 4,683,195, 4,683,202, and 4,800,159, assigned to Hoffman-La Roche, Inc., Nutley, N.J. Amplicon 885 was produced by PCR amplification of Bst genomic DNA. Amplicon 764 was generated using amplicon 885 as a substrate using a second set of primers to nucleotide sequences within amplicon 885.

Oligonucleotides 16 and 25, shown in FIG. 1 (SEQ ID NOS: 1 and 3, respectively) were used as primers in a PCR reaction using genomic Bst DNA as the template. The PCR reaction mixtures contained 50 pmoles of each primer, 0.5 µg template DNA and 5 units of Thermus thermophilus DNA polymerase in 100 µl of 10 mM Tris-HCl (pH 8.3), 50 mM potassium chloride, 1.5 mM magnesium chloride, and 0.2 mM each of DATP, dCTP, dGTP and dTTP. The reaction mixtures were overlaid with 100 µl of silicone oil and incubated in an thermocycler apparatus at 95° C. for 1.5 minutes followed by thirty cycles of 95° C. 0.5 min, 50° C. 2.5 min and 72° C. 1.5 min. A second set of reactions was done as above except dimethylsulfoxide (DMSO) was added to a final concentration of 13.3% (v/v) to reduce the $T_m$ of the primers by approximately 8° C. The effective annealing temperature of the resulting reaction was 58° C. (see Chester and Marshak, *Anal. Biochem.* 209:284–290 (1993)). Separate reactions were run with no Bst template DNA added as negative controls.

Oligomers 17 and 24, also shown in FIG. 1 (SEQ ID NO: 5 and 7, respectively) were used as primers in secondary PCR reactions. Aliquots of 2 μl containing the amplicons from each of the primary reaction mixtures described above were used as templates. All reaction conditions were the same as in the primary reactions; amplicons generated at the 50° C. annealing temperature in the primary amplifications were used at 50° C. in the secondary reactions, and amplicons generated using 13.3% DMSO in the primary amplifications were similarly incubated with 13.3% DMSO in the secondary reactions.

Aliquots of 16 μl from each reaction mixture were subjected to electrophoresis on a 1.5% agarose gel and the gels were stained with ethidium bromide. Expected amplicon sizes were calculated based on the published Bca sequence. In each gel lane corresponding to a reaction mixture containing template DNA, a single band appeared having approximately the expected size: a band of approximately 885 base pairs in the reaction mixture using oligomers 16 and 25 as PCR primers, and a band of approximately 764 base pairs in the reaction mixture using oligomers 17 and 24 as PCR primers. No amplicons were observed in the negative controls lacking template DNA. The gel was Southern blotted and probed with labelled oligonucleotide 20, shown in FIG. 1 (SEQ ID NO: 11) as described above. The primer extension products of both the primary and secondary PCR reactions were detected by labelled oligonucleotide 20. No hybridization was observed in the negative control reactions.

Amplicon 1143

Amplicon 1143 (also shown in FIG. 2) was produced by PCR amplification of Bst genomic DNA using the same conditions as in the primary amplifications above. The primers used in this reaction were oligonucleotides 20 and 21, shown in FIG. 1 (SEQ ID NOS: 11 and 9, respectively). An aliquot of this reaction mixture was subjected to electrophoresis on a 1% agarose gel and stained with ethidium bromide. A single amplicon of approximately the expected size of 1143 base pairs was observed, and no amplicon was observed in the negative controls. The gel was subjected to the Southern transfer method and the membrane probed with labelled oligonucleotide 16 (FIG. 1) as described above. The primer extension product hybridized with labelled oligonucleotide 16 (SEQ ID NO:1). No hybridization was observed with the negative control reactions.

Cloning of amplicons 885 and 1143

Amplicons 885 and 1143 were gel isolated as described above. The purified amplicons were incubated with T4 DNA polymerase (Stratagene Cloning Systems) to assure that the ends were blunt. The amplicons were incubated at 11° C. for 20 minutes with 5 units of T4 DNA polymerase in a 50 μl reaction containing 10 mM Tris-HCl (pH 7.9), 10 mM magnesium chloride, 50 mM sodium chloride, 1 mM dithiothreitol, 100 μg/ml acetylated bovine serum albumin (BSA) (New England Biolabs) and 0.1 mM each of DATP, dCTP, dGTP and dTTP. Following the reaction, the amplicons were diluted with TE buffer (10 mM Tris-HCl, 1 mM EDTA (pH 8.0)) and extracted with solutions of phenol/chloroform/isoamyl alcohol and chloroform/isoamyl alcohol as described above. The primer extension products were co-precipitated in ethanol with 0.15 μg plasmid pGem3Z which had been digested with Sma I and again extracted using the same two solutions as above. The precipitated nucleic acids were resuspended and incubated overnight at room temperature in a 10 μl total volume containing 50 mM Tris-HCl (pH 7.6), 10 mM magnesium chloride, 1 mM ATP, 1 mM dithiothreitol, 5% polyethylene glycol-8000, and 10 units T4 DNA ligase. Eight units of Sma I were also added to this reaction to prevent religation of the vector.

The resulting circularized amplicon-containing plasmids were used to transform XL1-Blue MRF' cells. The transformed cells were plated on LB agar plates containing ampicillin, IPTG and X-gal. White colonies, indicating the presence of DNA inserts, were selected and grown in LB broth with ampicillin. Plasmid minipreparations were made according to the standard boiling procedure (see e.g., Sambrook, supra, previously incorporated by reference) and the isolates were analyzed using restriction endonuclease digestions of the clones.

Figure 3:
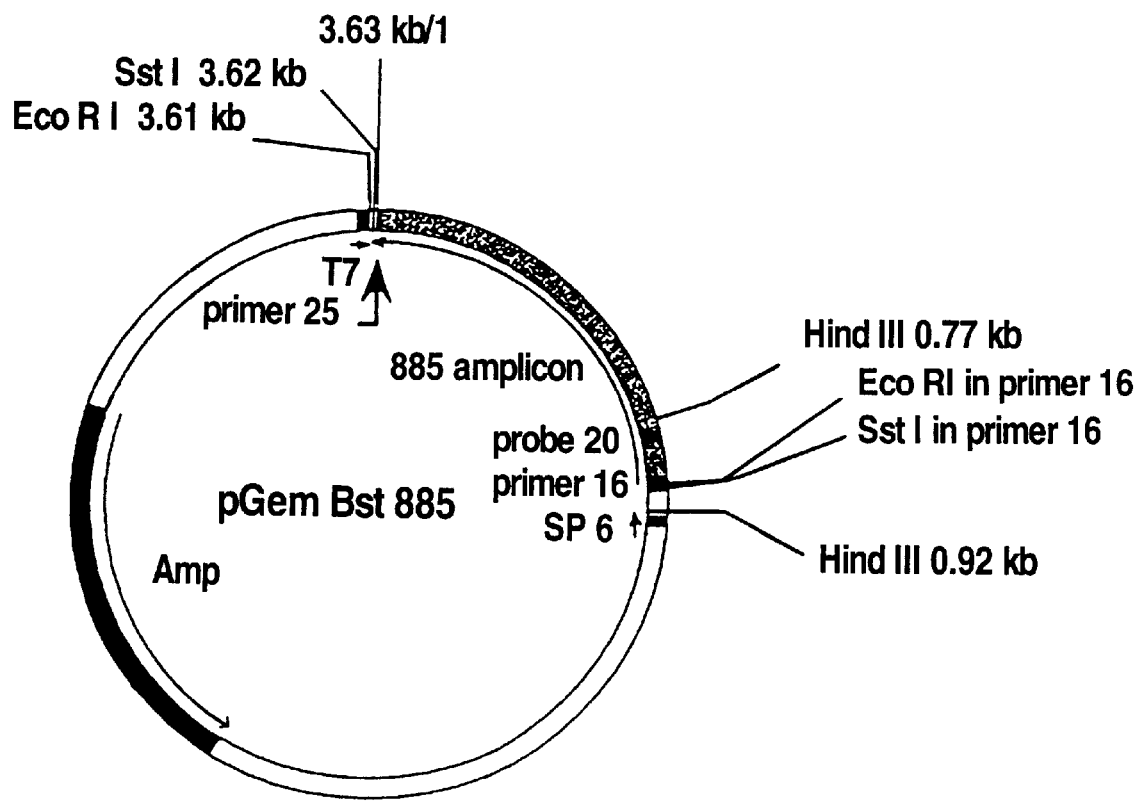
FIG. 3 is a illustration of plasmid pGEM Bst 885.

Detection of the 885 amplicon insert was accomplished by digesting each plasmid miniprep with Eco RI plus Hind III. The digests were subjected to electrophoresis on a 1% agarose gel and Southern blotted as described above. The Southern blots were hybridized with labelled oligonucleotide 20. The probe detected faint low molecular weight bands. Since the sequence of oligonucleotide 20 was expected to be near the end of the amplicon (see FIGS. 2 and 3), it appeared likely that its corresponding sequence within the amplicon was located between the vector restriction site and an Eco RI or Hind III restriction site within the amplicon; oligonucleotide 16 (one of the primers) contained a known Eco RI site but would not generate such a small restriction fragment. Two isolates were tested further by performing both separate and combined Eco RI and Hind III digestions, as well as Sst I and Hind III digestions, followed by Southern blotting and hybridization with labelled oligonucleotide 20. The structure of the amplicon 885-containing clone was deduced from these experiments, and is shown in FIG. 3. This clone was named pGem Bst 885.

Figure 4:
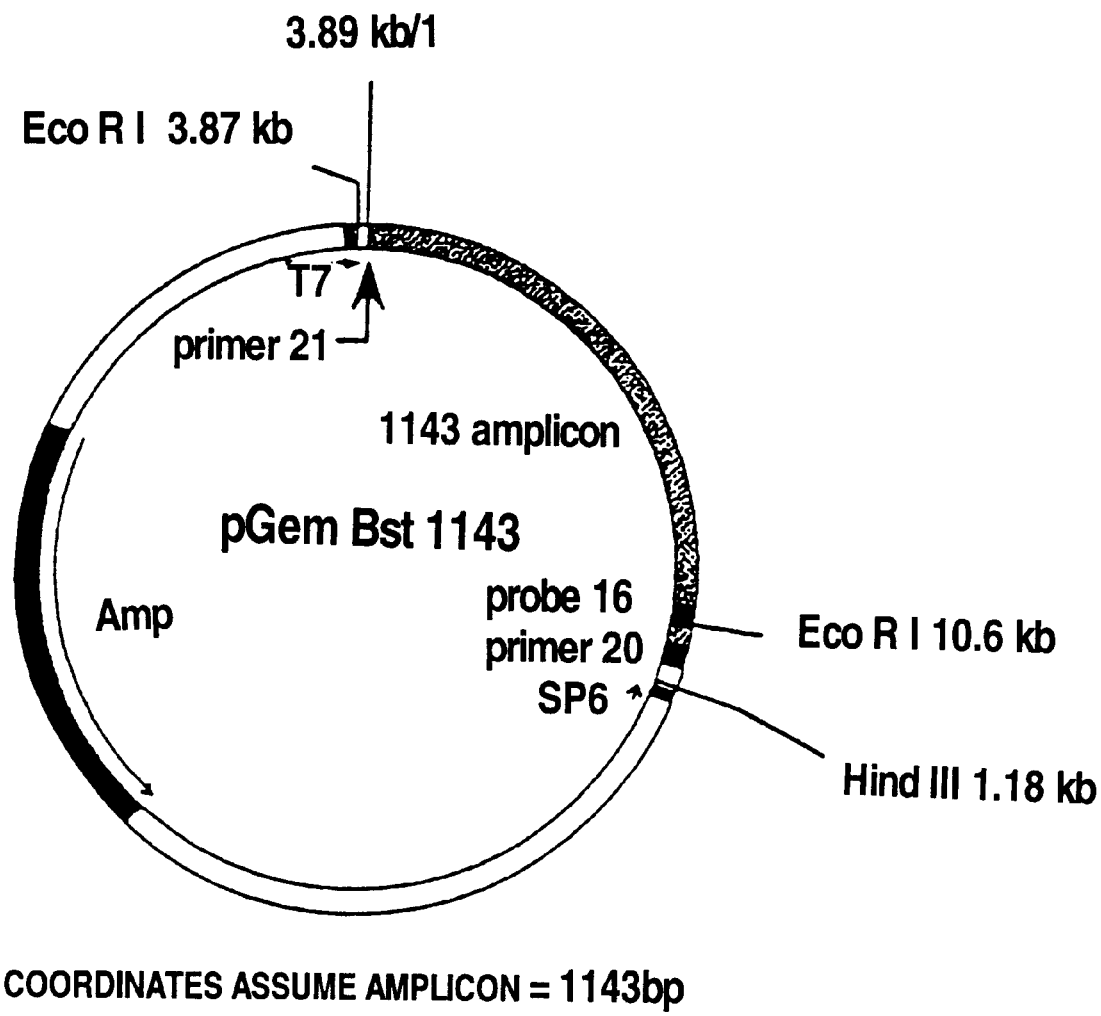
FIG. 4 is a illustration of plasmid PGEM Bst 1143.

Detection of the 1143 amplicon insert was performed as above by digesting each plasmid miniprep with Eco RI and Hind III followed by agarose gel electrophoresis. Inserts of the predicted size were observed in several isolates as determined by ethidium bromide staining. After Southern blot hybridization analysis, the inserts were found to hybridize strongly with labelled oligonucleotide 16. One clone was selected as representative and the deduced restriction map is shown in FIG. 4. This clone was named pGem Bst 1143.

Partial sequencing of the amplicon clones

Sequencing reactions were performed as described above using both pGem Bst 885 and pGem Bst 1143 DNA samples. The primers used in both sets of reactions were the SP6 and T7 promoter primers available from Promega Corp. (SEQ ID NOS: 15 and 16, respectively). These primers were specific for the SP6 and t7 promoter regions in the pGem vector, and were useful for sequencing the Bst amplicon inserts in both directions. The resulting amplicon sequences were aligned with the known Bca polymerase gene sequence and were found to be approximately 88% homologous in the overlapping regions. In addition, the sequences present in the overlap region of the two amplicons were the same, indicating that they had arisen from the same gene. The evidence therefore indicated that the amplicons represented true fragments of the Bst DNA polymerase gene.

The sequences obtained from the 885 and 1143 amplicon clones provided two pieces of information that would allow the isolation of gene fragments obtained from genomic Bst DNA. First, the sequence of the Bst polymerase gene in the regions corresponding to oligonucleotides 16, 17, 20 and 24 indicated that these oligonucleotides would be suitable for use as probes of genomic Bst DNA in Southern blots. Second, two restriction endonuclease sites within the Bst DNA polymerase gene were identified: an Sst I restriction site at Bca coordinate 1516 and a Hind III restriction site at Bca coordinate 1687. These sites provide a strategy for isolating fragments of the Bst polymerase gene from the genomic DNA.

Example 2

Identification and Cloning of Bst DNA Polymerase

Cloning the 3' End of the Gene

Aliquots of genomic Bst DNA were digested with Sst I and subjected to electrophoresis on 1% agarose gels, and Southern blotted as described above. The transfer membranes were then probed separately with six different labelled oligonucleotides and autoradiographed as described above. As shown in FIG. 5, labelled oligonucleotides 16, 20, 24 and 25 hybridized to an Sst I fragment approximately 2.1 kb in length. These oligonucleotides were designed based upon Bca DNA polymerase sequences near the 3' end of the gene. Two other oligonucleotides, 15 and 21, based upon Bca sequences toward the 5' end of the gene, did not hybridize to this Sst I fragment. These results indicated that the Sst I restriction site could be used to isolate a genomic DNA fragment containing the 3' end of the gene.

Twenty five µg of purified Bst genomic DNA was digested with Sst I and subjected to electrophoresis on a 1% agarose gel. Gel slices were excised in a region of the gel corresponding to approximately 2.1 kb. The DNA was purified from the gel slices as described above; approximately 0.45 µg were recovered.

Vector pGem 3Z was digested with Sst I and sequentially extracted with solutions of phenol/chloroform/isoamyl alcohol and chloroform/isoamyl alcohol as described above. The gel purified 2.1 kb Sst I fragment was ethanol precipitated together with 0.23 µg of the Sst I-digested pGem 3Z vector. The precipitated DNA was redissolved and ligated at 16° C. in a 15 µl reaction overnight as described above. The ligation mixture was used to transform XL1-Blue MRF' cells and the transformed cells were plated onto LB agar plates containing ampicillin, IPTG and X-gal. White colonies, indicating insert DNA, were selected and grown overnight in 200 µl LB broth cultures containing ampicillin in microtiter dishes. One hundred µl aliquots of each culture were filtered onto a Schleicher & Schuell Nytran (+) membrane using a Bio Rad Bio-Dot microfiltration apparatus and washed with 200 µl of 10× SSC. The membrane was air dried for 5 minutes and then successively placed onto filter papers soaked with: 10% SDS for 3 minutes, 0.5M sodium hydroxide for 5 minutes, 1M Tris-HCl (pH 8.0) for 5 minutes and 0.7M Tris-HCl (pH 8.0) containing 1.5M sodium chloride for 5 minutes. The filter was air dried, baked in a vacuum oven at 80° C. for 2 hours and then hybridized with labelled oligonucleotide 20, as described above.

A clone was identified which hybridized to oligonucleotide 20. This clone was cultured overnight at 37° C. in LB broth containing ampicillin. Plasmid minipreparations were made as described above, and plasmid DNA was digested with Sst I and Hind III, both separately and together. The restriction digests were subjected to electrophoresis on a 1% agarose gel and stained with ethidium bromide. Two Sst I bands were observed at locations corresponding to approximately 2.1 kb and 2.7 kb, and virtually the same pattern was observed on gels loaded with plasmid DNA digested with Sst I plus Hind III. Plasmid DNA digested with Hind III alone gave rise to a large band upon electrophoresis of approximately 4.5 kb, and a very small band of approximately 0.1–0.2 kb. The gel was Southern blotted and allowed to hybridize with labelled oligonucleotide 25 as described above. The probe hybridized to the 2.1 kb Sst I bands in lanes corresponding to both the Sst I and Sst I plus Hind III restriction digestion reactions and to the 4.5 kb band in lanes corresponding to the Hind III digestion.

To verify that the clone contained the expected 5' end of the 2.1 kb Sst I fragment, it was also probed with labelled oligonucleotide 16, which was expected to be complementary to a region of the Bst DNA polymerase gene very near the Sst I site. In this case, DNA dot blots were used to identify clones containing the desired nucleotide sequence, rather than a Southern hybridization procedure. One µg aliquots of plasmids pGem 3Z, pgem Bst 1143 and the plasmid thought to contain the 2.1 kb Sst I fragment were denatured in 110 µl 0.3M sodium hydroxide at 65° C. for one hour. One hundred and ten µl of 2M ammonium acetate was added and the samples were filtered onto a Schleicher & Schuell Nytran (+) membrane using a Bio Rad Bio-Dot microfiltration apparatus as described above. The membrane was washed with 1M ammonium acetate and baked in a vacuum oven at 80° C. for 45 minutes. The membrane was then allowed to hybridize with oligonucloetide 16 as described above. Both the plasmid thought to contain the 2.1 kb Sst I genomic fragment clone and the pGem Bst 1143 amplicon clone hybridized strongly with the labelled probe, indicating that the 5' end of the fragment was present in both plasmids. Preliminary sequencing reactions were done as described above, using the SP6 promoter primer (SEQ ID NO: 15). The resulting nucleotide sequence matched the sequence deduced from the amplicon clones pGem Bst 885 and pGem Bst 1143 and also confirmed the presence of the Hind III site in the genomic clone.

Figure 6:
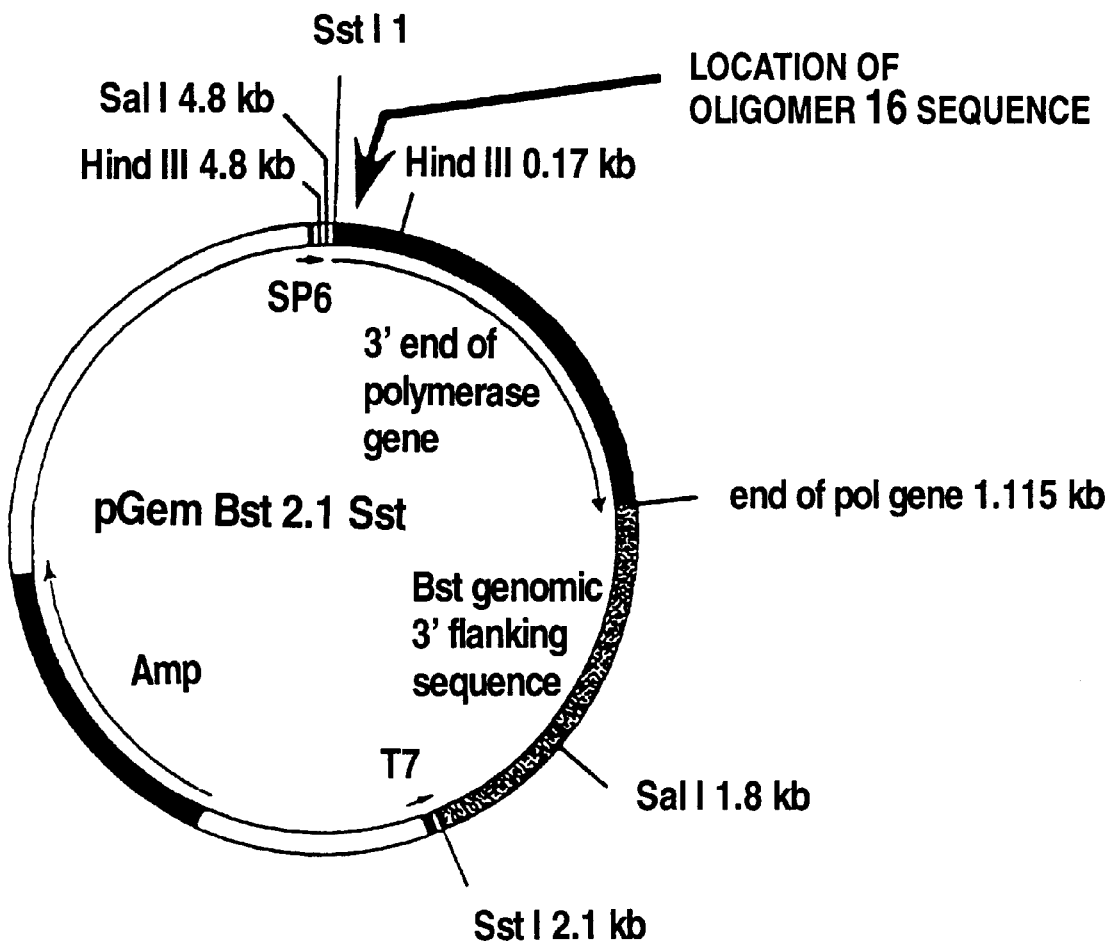
FIG. 6 is a illustration of plasmid pGEM Bst 2.1 Sst.

Additional restriction endonuclease digestions of this plasmid with restriction endonuclease Sal I yielded two bands of approximately 3.1 and 1.8 kb which indicated that a Sal I site was present in the 3' non-coding region downstream from the 3' end of the polymerase gene. This clone was named pGem Bst 2.1 Sst and is shown in FIG. 6.

Cloning the 5' End of the Gene

Because the 3' end clone pGem Bst 2.1 Sst contained a Hind III restriction site near the 5' end, the Hind III site was used to isolate a genomic Bst DNA fragment overlapping the 2.1 kb Sst I gene fragment of pGem Bst 2.1 Sst. In order to accomplish this, Bst genomic DNA was digested with Hind III plus a panel of second enzymes to identify a fragment of at least 1.7 kb, calculated to be large enough to contain the missing 5' portion of the DNA polymerase gene.

Bst genomic DNA was digested with Hind III alone and with Hind III plus the following second enzymes: Bam HI, Eco RI, Kpn I, Sph I, Xba I and Xmn I. Three microgram aliquots of each reaction mixture were subjected to electrophoresis in duplicate 1% agarose gels. Each gel was then analyzed by Southern blot using labelled oligonucleotide 20 or 21 as a probe, as described above. Upon analysis, each of the duplicate membranes displayed identical hybridization patterns. In lanes corresponding to each restriction digest, except the Hind III plus Sph I and Hind III plus Xmn I samples, a single band of approximately 4 kb was seen, indicating that the closest Hind III site upstream from the previously determined Hind III site in the 3' fragment clone was 4 kb distant, and that there were no restriction sites for the second enzymes between these Hind III sites. The lanes corresponding to the Hind III plus Xmn I digests displayed a single band of approximately 1.4 kb, which would not be long enough to contain the entire 5' end of the gene, as predicted from the Bca nucleotide sequence. The lanes corresponding to the Hind III plus Sph I digests displayed a single band of approximately 2.8–3 kb.

This 3 kb fragment was purified and cloned as follows. Bst genomic DNA was digested with Hind III plus Sph I at 37° C. Vector pGem 3Z was also digested with the same enzymes. Both digests were subjected to electrophoresis on a 1% agarose gel and stained with ethidium bromide. The resulting vector fragment and the 3 kb Hind III/Sph I Bst genomic fragment were excised from the gel, and the DNA was gel purified as described above. Approximately 125 ng of the vector DNA were ethanol precipitated together with the 3 kb Hind III/Sph I fragment. The precipitated DNA was redissolved and allowed to ligate overnight at 16° C. in a reaction mixture containing one unit of T4 DNA ligase in a total volume of 15 μl. The ligation reaction mixture was used to transform XL1-Blue MRF' cells and the transformed cells were plated onto LB agar plates containing ampicillin, IPTG and X-gal. White colonies, indicating DNA inserts, were selected and grown overnight in 200 μl LB broth cultures containing ampicillin in microtiter dishes. One hundred μl aliquots of each culture were filtered onto duplicate hybridization membranes as described above, air dried, baked in a vacuum oven at 80° C. for 2 hours. The duplicate membranes were separately allowed to hybridize with labelled oligonucleotides 20 and 21. Samples obtained from three cultures showed some hybridization with each probe. These cultures were cultured overnight in LB broth containing ampicillin and plasmid minipreparations were made as described above. The resulting plasmid DNA from each sample was digested with Xmn I alone and with Hind III plus Sph I, subjected to electrophoresis on a 1% agarose gel and stained with ethidium bromide. Samples from two of the clones appeared to yield DNA bands of the expected size. (The Hind III plus Sph I reaction was expected to yield fragments of approximately 3 kb and 2.7 kb. These bands could not be resolved on the gel. The Xmn I reaction was expected to yield DNA fragments of approximately 3.4 kb and 2.4 kb). One of these clones was selected for further analysis. The plasmid DNA from this clone was digested with Hind III and subjected to electrophoresis, as described above. A single band of approximately 5.6 kb was present as predicted for the linear plasmid. The same plasmid DNA was also digested with Xmn I, Hind III plus Xmn I and Hind III plus Sph I, subjected to electrophoresis on triplicate 1% agarose gels, stained with ethidium bromide and transferred to hybridization membranes by the method of Southern, as described above. The triplicate membranes were then separately allowed to hybridize with labelled oligonucleotides 15, 21 and 20. A summary of the results obtained are indicated below.

| | Observed ethidium stained bands (kb) | Detected with labelled oligo 15 | Detected with labelled oligo 20 | Detected with labelled oligo 21 |
|---|---|---|---|---|
| Digested with Xmn I | 3.2<br>1.1<br>0.9<br>0.23 | 1.1 | 3.2 | 3.2 |
| Digested with Hind III + Xmn I | 1.8<br>1.4<br>1.1<br>0.9<br>0.23 | 1.1 | 1.4 | 1.4 |
| Digested with Hind III + Sph I | 2.7 (doublet) | 2.7 | 2.7 | 2.7 |

Figure 7:
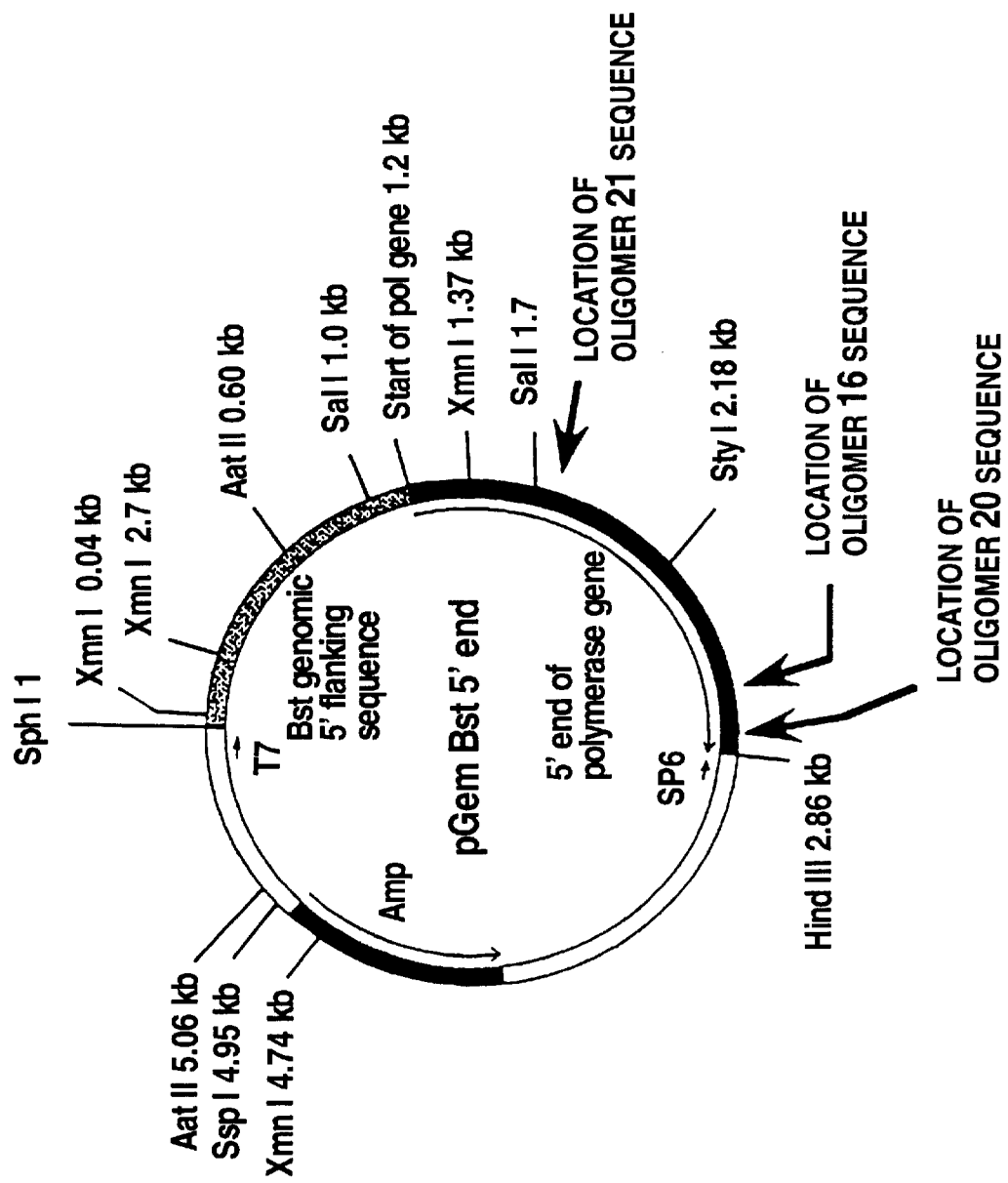
FIG. 7 is a illustration of plasmid pGEM Bst 5' end.

These results indicated that this clone contained the 5' end of the Bst DNA polymerase gene. Preliminary sequencing reactions were done as described above, using the SP6 promoter primer of nucleotide sequence SEQ ID NO: 15. This promoter-primer primes a sequencing reaction beginning from outside the Bst DNA polymerase coding region and extending towards the 5' end of the gene. The results of the sequencing reaction showed that the nucleotide sequence of the DNA polymerase gene nearest the vector cloning site matched the sequence that had been previously obtained from the 5' end of the 3' gene fragment of pGem Bst 2.1 Sst. These data thereby indicated that the new 5' gene fragment clone overlapped the cloned 3' gene fragment insert. Additional restriction mapping of the new insert also revealed the presence of two Sal I sites: one approximately 0.2 kb upstream from the 5' end of the gene in the 5' flanking region, and one approximately 0.5 kb downstream from the 5' end of the gene, in the coding region. This new plasmid was named pGem Bst 5' end, and is shown in FIG. 7.

Example 3

Construction of a Plasmid Containing the Full Length Bst DNA Polymerase Gene

A plasmid containing a full length copy of the Bst DNA polymerase gene was constructed by combining segments of the 5' and 3' gene fragment clones pGem Bst 5' end and pGem Bst 2.1 Sst. The strategy used is outlined in FIG. 8.

First, a precursor plasmid was constructed which contained the portion of the 3' end of the gene shown as fragment A in FIG. 8A. Purified plasmid pGem Bst 2.1 Sst DNA was digested with Hind III plus Sal I and subjected to electrophoresis on a 1% agarose gel. A gel slice containing a DNA band of approximately 1.6 kb (fragment A) was excised and the DNA was gel purified, as described above. Plasmid vector pUC 18 was digested with the same two enzymes, and purified at the same time. Approximately 0.25 μg fragment A and 0.15 μg pUC 18 fragment were ethanol precipitated together. The nucleic acids were redissolved and ligated overnight at 16° C. in a reaction mixture containing 10 units T4 DNA ligase in a volume of 15 μl, as described above. The ligation mixture was used to transform XL1-Blue MRF' cells and the transformed cells were plated on LB agar plates containing ampicillin, IPTG and X-gal. White colonies, indicating a DNA insert, were selected and grown in LB broth with ampicillin. Plasmid minipreparations were made, as described above, and the resulting plasmid DNA was digested with Hind III plus Sal I, subjected to electrophoresis on a 1% agarose gel and stained with ethidium bromide. A sample was identified which gave rise to DNA bands of the expected sizes of 1.6 and 2.7 kb. This plasmid clone was named pUC Bst 3' end.

pGem Bst 5' end was used for isolating the portion of the 5' end of the gene shown as an Aat II/Hind III fragment (fragment B) in FIG. 8B as follows. Sequencing and restriction mapping of this clone had revealed the Sal I and Aat II restriction sites indicated. Purified pGem Bst 5' end DNA was digested with Hind III plus Sph I plus Ssp I and the precursor 2.86 kb Hind III/Sph I fragment was gel purified, as described above. The precursor fragment was subsequently digested with Aat II and the 2.3 kb fragment B was gel purified, as described above. (This fragment was prepared in two stages, with the initial Sph I and Ssp I digestions in order to eliminate unwanted plasmid fragments that would have co-migrated with the desired fragment during electrophoresis.)

Plasmid pUC Bst 3' end DNA was digested with Hind III plus Aat II and the large fragment was gel purified as described above. Approximately 0.6 µg of the digested pUC Bst 3, end DNA was ethanol precipitated together with approximately 0.5 µg fragment B and allowed to ligate overnight at 16° C. in a reaction mixture containing 10 units of T4 DNA ligase. The ligation mixture was used to transform XL1-Blue MRF' cells and the transformed cells were plated on LB agar plates containing ampicillin. Colonies were selected, grown in LB broth containing ampicillin and plasmid minipreparations were made, as described above. The plasmid DNA was digested with Sal I digestions and subjected to agarose gel electrophoresis, as described above. Three bands having the expected sizes of approximately 2.7, 2.6 and 0.7 kb were observed in the majority of the plasmid preparations so screened, indicating successful construction of the full length DNA polymerase gene, including 5' and 3' genomic flanking sequences. One of these clones was selected as a representative clone. This plasmid was named pUC Bst I and is shown in FIG. 8B. The Bst DNA polymerase gene and its 5' and 3' flanking sequences are shown in SEQ ID NO: 19.

Example 4

Construction of a Bst DNA Polymerase Clone Lacking the 5'-3' Exonuclease Domain

Figure 9A:
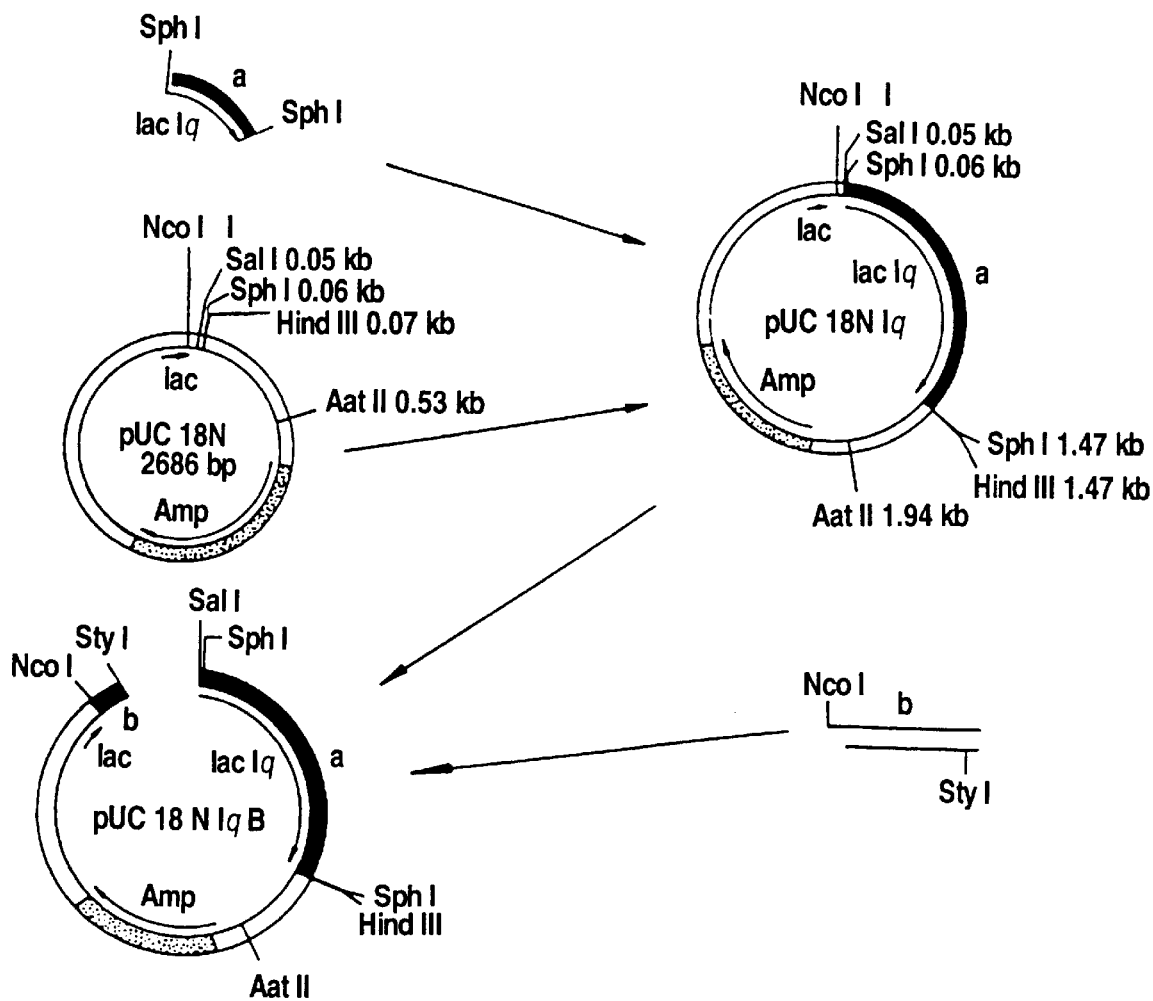
FIGS. 9A and 9B is a representation of the strategy for the construction of plasmid pUC Bst 2.
Figure 9B:
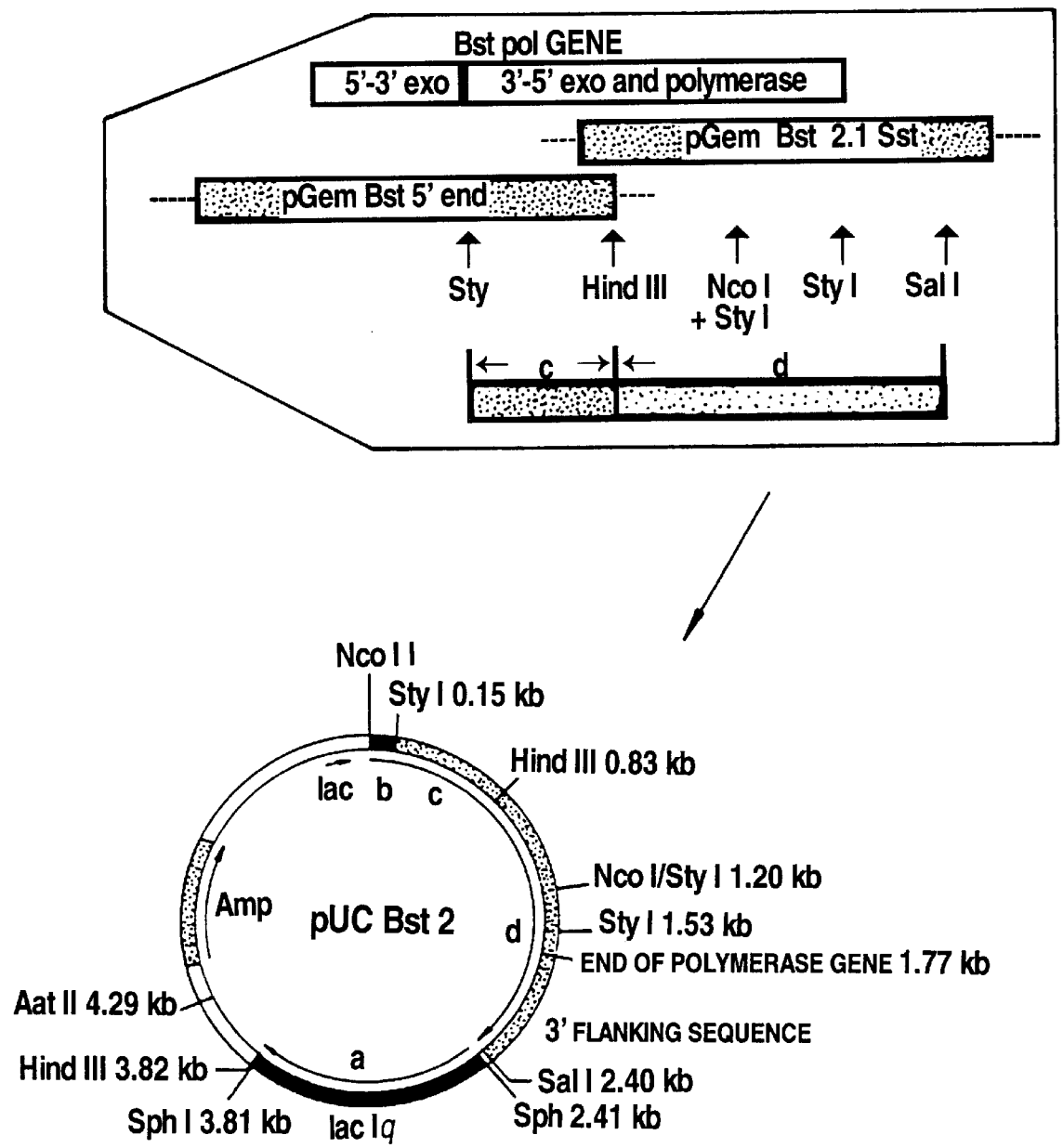

A plasmid clone was constructed which contained only the 3'-5' exonuclease and polymerase domains of the Bst DNA polymerase gene as follows. Generally, the plasmid was constructed by first inserting the I$^q$ repressor gene from plasmid pMAL™-P2 (New England Biolabs) into a modified pUC 18 plasmid so that the final clone would be inducible with IPTG in a variety of host cells. Previous publications had indicated that expression of full length DNA polymerase I is lethal to E. coli host cells. See, e.g., Joyce, et al., *Proc. Natl. Acad. Sci. USA* 80:1830–1834 (1983). The DNA polymerase gene fragment to be cloned was assembled from three components: a 3' gene fragment containing the Hind III to Sal I region from pGem Bst 2.1 Sst, a middle gene fragment containing the region from a Sty I site to the Hind III site in pGem Bst 5' end, and a fragment made using synthetic oligonucleotides to complete the 5' end of the coding region for Bst DNA polymerase, and to provide a cloning site. The cloning strategy is shown in FIGS. 9A and 9B.

Step 1: One µg plasmid pMAL™-p2 was digested with restriction endonucleases Msc I plus Ssp I, subjected to electrophoresis in an agarose gel, and the resulting band of approximately 1.39 kb containing the lac I$^q$ repressor gene was gel purified, as described above. This fragment was then ligated to 20 pmol of Sph I linkers (New England Biolabs) overnight at room temperature in a reaction mixture containing 20 units of T4 DNA ligase, as described above. The T4 ligase was heat-inactivated at 75° C. for 5 minutes and the ligation mixture was ethanol precipitated. The DNA fragment was then redissolved and digested with Sph I, then subjected to electrophoresis and gel purified, as described above. The resulting DNA fragment is shown as fragment "a" in FIG. 9A. Plasmid vector pUC 18N had been constructed previously by making a two base substitution in pUC 18 which resulted in the creation of a new Nco I cloning site. As indicated below, the A nucleotide 11 bases upstream from the Eco RI site was substituted with a G, and the T residue 15 bases upstream from the EcoR I site was substituted with a C. Nucleotide sequences comprising a restriction endonuclease site are indicated by underlining.

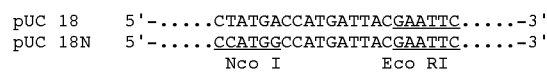

pUC 18   5'-.....CTATGACCATGATTAC<u>GAATTC</u>......-3'
pUC 18N  5'-.....<u>CCATGG</u>CCATGATTAC<u>GAATTC</u>......-3'
                 Nco I          Eco RI

Plasmid pUC 18N was digested with Sph I, subjected to electrophoresis in an agarose gel and gel purified, as described above. The linearized plasmid was then coethanol precipitated with the lac I$^q$ fragment described above, and the two DNA fragments were ligated overnight at 16° C. in a reaction mixture containing 2 units of T4 DNA ligase, as previously described. The ligation mixture was used to transform XL1-Blue MRF' cells and the transformed cells were plated on LB plates containing ampicillin, IPTG and X-gal. White colonies, indicating the presence of DNA inserts, were selected and grown in LB broth containing ampicillin and plasmid minipreparations were made as previously described. The plasmid DNA preps were each digested with Eco RI plus Eco RV and with Hind III plus Eco RV, and subjected to electrophoresis in an agarose gel. A plasmid clone was selected which displayed DNA bands of the expected size (Eco RI/Eco RV: 3.15 kb+0.96 kb, Hind III/Eco RV: 3.59 kb+0.52 kb) and was designated pUC 18N I$^q$.

Step 2: The synthetic fragment required to complete the 5' end of the cloned gene was constructed using two partially complementary single-stranded synthetic oligonucleotides (SEQ ID NOS: 17 and 18). These oligonucleotides were designed based on the sequence of the Bst DNA polymerase gene obtained by sequencing pGem Bst 5' end DNA. The oligonucleotides were structured so that their complementary regions would cause the oligonucleotides to overlap each other by 28 bases at their 3' ends upon hybridization. The annealed single-stranded oligonucleotides were extended with the Klenow fragment from E. coli DNA polymerase I, which caused the formation of a double-stranded DNA molecule. The resulting duplex DNA molecule contained an Nco I restriction endonuclease site near the 5' end, a Sty I restriction endonuclease site near the 3' end, and the Bst DNA polymerase gene sequence corresponding to gene coordinates 868–1012. This fragment contains the 5' end of the 3'-5' exonuclease domain of the Bst DNA polymerase gene with a new Nco I cloning site added at the 5' end of this domain, and the native Sty I cloning site at the 3' end of the fragment. This DNA fragment is represented as fragment "b" in FIG. 9A.

To accomplish step 2, 15 pmol each of oligonucleotides having SED ID NOS: 17 and 18 were mixed in a total volume of 96 μl of a solution containing 50 mM potassium chloride, 2 mM magnesium chloride and 20 mM Tris-HCl (pH 8.0). The solution was incubated at 76° C. for 10 minutes and then allowed to slowly cool to room temperature over a few hours in order to anneal the oligonucleotides. The mixture was brought to 100 μl total volume with the addition of 10 units of the Klenow fragment of E. coli DNA polymerase I and 0.2 mM each of DATP, dCTP, dGTP and dTTP. The resulting reaction mixture was incubated at room temperature for 6 minutes, 37° C. for 45 minutes and 42° C. for 10 minutes. The solution was then sequentially extracted with solutions of phenol/chloroform/isoamyl alcohol and chloroform/isoamyl alcohol as previously described, then ethanol precipitated. The double-stranded fragment was redissolved and digested in a reaction mixture containing 25 U of Nco I, and the resulting 0.15 kb fragment was gel purified, as described above.

Step 3: Plasmid pUC18N I$^q$, constructed in Step 1, was digested with Nco I, combined with fragment "b" from Step 2, and the plasmid and DNA fragment were ligated overnight at 16° C. The ligase was heat inactivated at 65° C. for 10 minutes and the ligation products were ethanol precipitated. The plasmid was digested with Sty I plus Sal I and gel purified, as described above.

Step 4: Bst DNA polymerase gene fragments were isolated and reassembled as follows. Plasmid pGem Bst 5' end was digested with Sty I plus Hind III, subjected to electrophoresis, and the resulting 0.68 kb DNA fragment (termed fragment "c") was gel purified. Plasmid pGem Bst 2.1 Sst was digested with Hind III plus Sal I. This digestion mixture was also subjected to electrophoresis, and the 1.57 kb DNA fragment (termed fragment "d") was gel purified, as previously described. Purified fragments "c" and "d" were combined and co-ethanol precipitated. The pelleted DNA was redissolved and allowed to ligate overnight in a 30 μl reaction mixture containing 4 U of T4 ligase at 16° C. The ligase was heat inactivated at 65° C. for 10 minutes and ligated fragments "c", and "d" were ethanol precipitated, then digested with Sal I. Following agarose gel electrophoresis, the resulting 2.25 kb ligation fragment "cd" was gel purified, as described above.

Step 5: The gel purified fragment "cd" was ligated with the plasmid produced in Step 3 in a 17 μl reaction mixture containing 2 U of T4 ligase at 16° C. overnight. The ligation reaction mixture was used to transform XL1-Blue MRF' cells and the transformants were plated on LB agar plates containing ampicillin. Colonies were selected, grown in LB broth containing ampicillin and plasmid minipreparations of the selected colonies were made. The DNA preparations were analyzed using restriction endonuclease digestions with Nco I plus Hind III and with Sph I plus Sty I. The restriction digests were subjected to agarose gel electrophoresis, and ethidium bromide staining. A clone was identified which gave rise to restriction fragments of the expected size (Nco I+Sty I: 2 bands at 2.62 kb, 0.83 kb, 0.37 kb and Sph I+Sty I: 2.77 kb, 1.41 kb, 1.05 kb, 0.88 kb, 0.33 kb). This clone was named pUC Bst 2 and is shown in FIG. 9; the Bst 2 gene insert, without its 5' and 3' untranslated regions (but with the untranslated termination codon) has a nucleotide sequence of SEQ ID NO: 22.

Example 5

Construction of Modified Versions of pUC Bst 2

Figure 11:
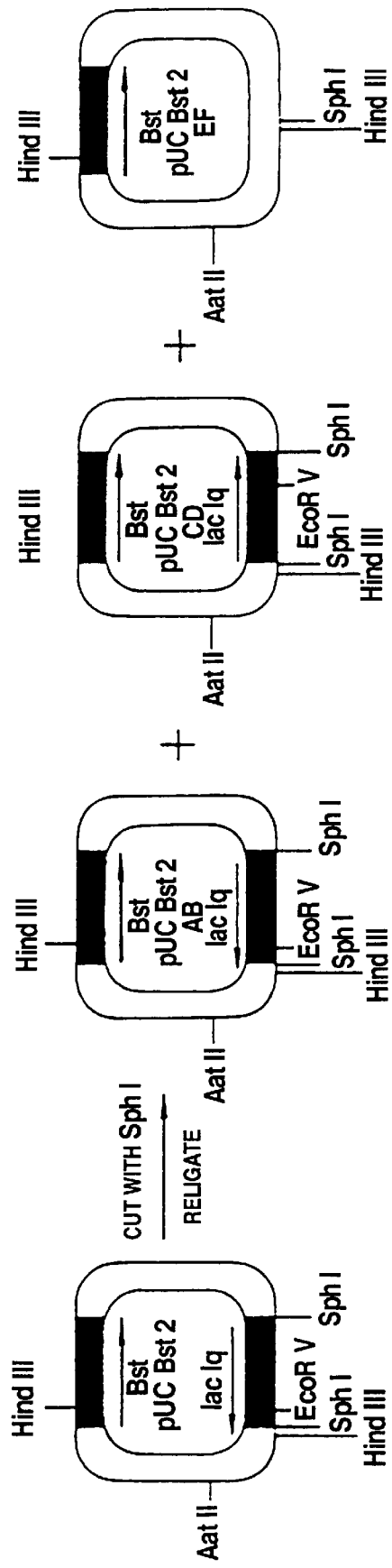
FIG. 11 is a representation of the strategy for the construction of plasmids pUC Bst 2 AB, pUC Bst 2 CD, and pUC Bst 2 EF.

In order to evaluate the effect of the lac I$^q$ repressor gene on the expression of the Bst DNA polymerase gene, modified versions of pUC Bst 2 were constructed in which the lac I$^q$ repressor gene was either deleted or reversed in orientation. To create these clones, pUC Bst 2 DNA was digested with Sph I restriction endonuclease to liberate the lac I$^q$ insert. The reaction mixture was sequentially extracted with solutions of phenol/chloroform/isoamyl alcohol and chloroform/isoamyl alcohol as previously described, and then ethanol precipitated. The sample was then redissolved and religated in a 20 μl reaction mixture containing 1 U of T4 DNA ligase overnight at 16° C. The ligation reaction mixture was used to transform E. coli 1200 cells, and the transformed cells were plated on LB agar plates containing ampicillin. Colonies were selected and grown in LB broth containing ampicillin. Plasmid minipreparations were made as described above. The samples were then digested with Eco RV plus Hind III, subjected to electrophoresis on a 1% agarose gel and then stained with ethidium bromide. Plasmids pUC Bst 2 "AB", "CD" and "EF" were identified based on the expected band sizes indicated in the table below and in FIG. 11.

|  | pUC Bst 2 AB | pUC Bst 2 CD | pUC Bst 2 EF |
|---|---|---|---|
| Expected Eco RV and Hind III Restriction Fragments (base pairs) | 3445 2477 518 | 3445 2094 901 | 3445 1573 |

Example 6

Construction of a Bst DNA Polymerase Clone with a Deletion in the 5'-3' Exonuclease Domain A plasmid containing an in-frame deletion in the 5'-3' exonuclease domain of the Bst DNA polymerase gene was constructed in order to inactivate or diminish the 5'-3' exonuclease activity of the expressed gene product without modifying the domains of the gene affecting the 3'-5' exonuclease and DNA polymerase activities.

Figure 10:
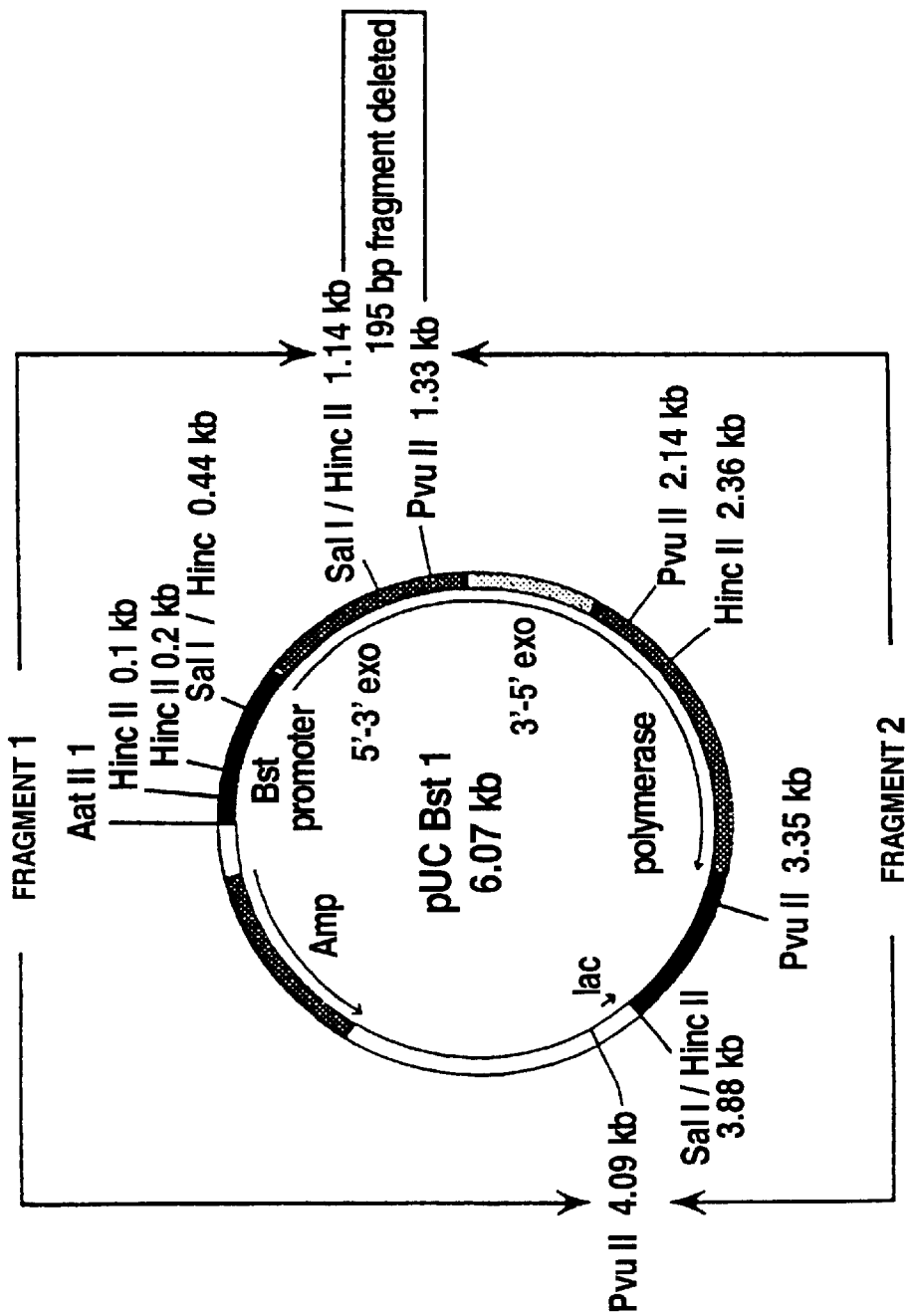
FIG. 10 is a representation of the strategy for the construction of plasmid pUC Bst 3.

The experimental strategy is outlined in FIG. 10, and utilized two restriction fragments from pUC Bst 1. The first fragment was prepared by digesting pUC Bst 1 DNA with Pvu II. The restriction digest was subjected to agarose gel electrophoresis. A fragment of 3,321 base pairs was identified and gel purified, as described. The purified fragment was then partially digested with Hinc II. Conditions suitable for partial digestion of this fragment were previously determined; conditions for conducting partial restriction digests of a substrate DNA are easily determined and well known to those of ordinary skill in the art. Upon agarose gel electrophoresis, a 3,126 base pair fragment was identified and gel purified.

To prepare the second restriction fragment, pUC Bst 1 was first digested to completion with Aat II in order to eliminate a DNA fragment predicted to co-migrate with the desired DNA fragment during agarose gel electrophoresis. The DNA was then partially digested with Pvu II under conditions previously determined by small scale pilot digestions. Following gel electrophoresis, the desired fragment of having a size of 2754 base pairs was excised from the gel and gel purified.

The two gel purified fragments so isolated were combined, ethanol precipitated, and the pellets were redissolved and allowed to ligate overnight in a 10 μl reaction mixture containing 1.5 U of T4 DNA ligase at room temperature. The ligation reaction mixture was used to transform XL1-Blue MRF' cells and the transformed cells were plated on LB agar plates containing ampicillin. Colonies were isolated and grown in LB broth containing ampicillin. Plasmid minipreparations were made, as previously described. The samples containing plasmid DNA were then digested with Pvu II, Sal I, Hind III plus Aat II and Sal I plus Sty I and subjected to electrophoresis on 1% agarose gels. A plasmid clone was identified which produced restriction fragments of molecular weight predicted from the map shown in FIG. 10; this clone was named pUC Bst 3; the DNA sequence of the Bst 3 cleavage product, without its 5' and 3' untranslated regions (and with the untranslated termination codon) is given in SEQ ID NO: 24.

Plasmid pUC Bst 3 is 195 base pairs shorter than the full length DNA polymerase clone pUC Bst 1 due to the removal of nucleotides from within the 5'-3' exonuclease domain of the DNA polymerase gene. This deletion results in the absence of 65 amino acid residues from the 5'-3' exonuclease domain of the expressed modified enzyme (residues 178–242). Among these 65 amino acids are two glycine residues which were thought to correspond to amino acids of *E. coli* DNA polymerase I necessary for 5'-3' exonuclease activity (gee Joyce, et al., *J. Mol. Biol.* 186:283–293 (1985)).

Example 7

Insertion of the Tetracycline Resistance Gene into all Bst DNA Polymerase Clones All of the Bst DNA polymerase containing plasmids described above contained a selectable marker gene conferring ampicillin resistance on the transformed host cells. This gene encodes β-lactamase. Cultures of host cells transformed with plasmids containing this gene and grown in media containing ampicillin are often found to have a relatively high rate of reversion, with resulting loss of cloned genes. In an attempt to stabilize the plasmids within host cells during culture, an additional selectable marker gene, conferring tetracycline resistance (tet$^r$), was added to each plasmid. A fragment containing this gene was isolated from pBR322 by digesting the plasmid with Eco RI plus Ava I, subjecting the digestion mixture to electrophoresis, and gel purifying the 1427 bp tetr fragment, as described above. The purified fragment was end-filled using the Klenow fragment of *E. coli* DNA polymerase I, and the resulting blunt-ended tet$^r$ fragment was ligated with Aat II oligonucleotide linkers (New England Biolabs); ligation of a gel purified DNA fragment with synthetic linkers was previously described above, and is well known to those of skill in the art. (See Sambrook, supra, previously incorporated by reference herein). The ligation mixture was ethanol precipitated and the DNA ligase was heat inactivated. The linker-containing fragment was then digested with Aat II, subjected to agarose gel electrophoresis and gel purified. Plasmid vector pUC 18 was digested with Aat II and following agarose gel electrophoresis, the linearized large fragment was gel purified. The Aat II digested vector and tet$^r$ fragment containing Aat II linkers were sequentially extracted in solutions of phenol/chloroform/isoamyl alcohol and chloroform/isoamyl alcohol, as described above. The extracted DNA fragments were combined, ethanol precipitated together and allowed to ligate in a reaction mixture containing T4 ligase. *E. coli* JM109 cells were transformed with this ligation mixture and plated on LB agar plates containing tetracycline. Colonies were isolated, cultured in LB broth containing tetracycline and plasmid minipreps were made, as described above. The plasmid preparations were digested with Eco RV and with Ssp I plus Hind III and subjected to electrophoresis on agarose gels. A clone was identified which gave rise to DNA fragments of the sizes expected for a plasmid containing the tet$^r$ gene in one of two possible orientations. The expected fragment sizes were: Eco RV: 4121, Ssp I+Hind III: 2102, 1868 and 150. This plasmid was named pUC Tet(+). Purified pUC Tet(+) DNA was isolated from a cell culture of this clone. This DNA was digested with Aat II, the digestion mixture subjected to agarose gel elctrophoresis, and the 1435 bp tet$^r$ fragment was gel purified, as previously described. This fragment was then used as a source of the tet$^r$ gene for insertion into each of the Bst DNA polymerase clones at their unique Aat II vector site.

To accomplish this, a preparation of plasmid DNA from each Bst DNA polymerase clone was digested with Aat II, subjected to agarose gel electrophoresis, and the linearized plasmid gel purified. The purified plasmid fragment was sequentially extracted with solutions of phenol/chloroform/isoamyl alcohol and chloroform/isoamyl alcohol. The purified Aat II linearized plasmid DNA was combined with the 1435 bp tet$^r$ fragment, and ethanol precipitated. The DNA pellet was dissolved, and the DNA fragments were allowed to ligate in a reaction mixture containing T4 DNA ligase, as described above. The ligation mixtures were used to transform *E. coli* 1200 cells, and the transformants were plated on LB agar containing tetracycline. Individual colonies were cultured in LB broth containing tetracycline, and plasmid minipreps of these cultures were made. In order to determine the orientation of the tet$^r$ gene in each plasmid, the plasmid DNA from each preparation was digested with either Hind III or with Eco RV in combination with another restriction endonuclease having a convenient recognition site within the cloned Bst DNA polymerase gene. Following gel electrophoresis and ethidium bromide staining, clones were selected which contained the tet$^r$ insert in each orientation relative to that of the Bst DNA polymerase gene. Plus (+) orientation was designated as the same orientation, relative to transcription, as the Bst polymerase gene and minus (−) orientation was designated as that opposite to the Bst DNA polymerase gene. Stock cultures of each of these clones were made, and the clones named as indicated below.

| Bst DNA Polymerase Clones without tet$^r$ | tet$^r$ Gene in (+) Orientation | tet$^r$ Gene in (−) Orientation |
|---|---|---|
| pUC Bst 1 | pUC BSt 1 T (+) | pUC Bst 1 T (−) |
| pUC Bst 2 | pUC Bst 2 T | |
| pUC Bst 2 AB | pUC Bst 2 A | pUC Bst 2 B |
| pUC Bst 2 CD | PUC Bst 2 C | pUC Bst 2 D |
| pUC Bst 2 EF | pUC Bst 2 E (same as pUC Bst 2 T) | pUC Bst 2 F |
| pUC Bst 3 | pUC Bst 3 T (+) | pUC Bst 3 T (−) |
| pUC Bst 4 | pUC Bst 4 T (+) | pUC Bst 4 T (−) |

Example 8

Preliminary Evaluation of Enzyme Expression in Bst DNA Polymerase Clones

As a preliminary determination of the expression of active Bst DNA polymerase from the clones constructed as described herein, they were grown overnight in cultures of LB broth containing either ampicillin or tetracycline. Cultures of pUC Bst 2 containing the lac I$^q$ gene in each orientation were also given 1 mM IPTG to induce expression of the enzyme. The amino acid sequences of Bst 1, Bst 2, and the cleavage product of Bst 3 are shown as SEQ ID NOS: 20, 23, and 25, respectively. Aliquots of 0.5 ml of each culture were analysed by SDS gel and by enzyme activity assays as follows.

Each aliquot for enzyme activity assays was centrifuged for 2 minutes in a microcentrifuge, and the cell pellets were washed one time with wash buffer (50 mM sodium chloride, 5 mM EDTA, 0.25M sucrose, 50 mM Tris-HCl (pH 8.0)). The pellets were frozen at −80° C. and each resuspended in 200 μl of lysis buffer (10 mM sodium chloride, 1 mM EDTA, 1% μlycerol, 25 mM dithiothreitol, 1 mM phenylmethylsulfonyl fluoride (PMSF), 500 μg/ml lysozyme, 10 mM Tris-HCl (pH 8.0)). After 20 minutes on ice, 100 μl of 0.75% (v/v) Triton X-100 was added to each sample, and the sample was frozen on dry ice and thawed three times. The resulting cell lysate was diluted 5,000 fold in enzyme dilution buffer (100 mM sodium chloride, 0.1 mM EDTA, 0.01% NP-40 (a nonionic detergent comprising a polyglycol ether derivative; Sigma Chemical Co., St. Louis, Mo.), 10% μlycerol, 20 mM Tris-HCl (pH 7.5)) and 10 μl aliquots were assayed for DNA polymerase activity at 60°C., as described above. The results of two experiments are shown in the tables below. The assay results are expressed in RLU (relative light units).

The first experiment made use of two $E.$ $coli$ host cell strains, strain XL1-Blue MRF' and the $E.$ $coli$ 1200 strain. $E.$ $coli$ XL1-Blue MRF' contains an episomal copy of $tet^r$. Strain XL1-Blue MRF' was transformed with plasmids pUC Bst 1, pUC Bst 2 and pUC Bst 3, all lacking the $tet^r$ gene. The enzyme activities of lysates from cultures of these clones were compared with those of lysates from $E.$ $coli$ 1200 host cells containing versions of the same plasmids but with the tetr gene in each orientation.

| | DNA Polymerase Activity at 60° C. (RLU) | | |
|---|---|---|---|
| | Host Cell Strain | | |
| | | $E.$ $coli$ 1200 | |
| | XL1-Blue MRF[1] No $tet^r$ Gene | $tet^r$ (+) Orientation | $tet^r$ (−) Orientation |
| pUC Bst 1 | 38,834 | 75,644 | 70,968 |
| pUC Bst 2 | 4,868 | 9,382 | Not Done |
| pUC Bst 3 | 27,737 | 63,675 | 45,992 |
| pUC 18 (Negative Control) | 4,324 | | |
| pUC $tet^r$ (+) (Negative Control) | | 4,730 | |

In a second experiment, the versions of pUC Bst 2 (A, B, C, D, E and F), constructed as described above, were compared with pUC Bst 1 T(+) and pUC Bst 3 T(+) to examine the effect of the lac $I^q$ repressor gene on Bst DNA polymerase expression. All clones used for this experiment were in the $E.$ $coli$ 1200 host cell line, and all clones which contained the lac Iq gene (pUC Bst 2 A, B, C and D) were grown in the presence of 1 mM IPTG to induce expression of the Bst DNA polymerase gene, under the control of the lac promoter in these plasmids.

| DNA Polymerase Activity at 60° C. (RLU) | |
|---|---|
| pUC Bst 1 T (+) | 67,747 |
| pUC Bst 2 A | 2,993 |

| DNA Polymerase Activity at 60° C. (RLU) | |
|---|---|
| pUC Bst 2 B | 2,644 |
| pUC Bst 2 C | 2,729 |
| pUC Bst 2 D | 3,664 |
| pUC Bst 2 E | 3,895 |
| pUC Bst 2 F | 7,876 |
| pUC Bst 3 T (+) | 49,275 |
| pUC tetr (+) (Negative Control) | 1,094 |

Aliquots of cell lysates generated in both experiments were run on SDS polyacrylamide gels, and stained with Coomassie Brilliant Blue as described in Sambrook, supra, previously incorporated by reference herein. These gels revealed prominent new bands in all cell lysates made from host cells containing pUC Bst 1 and pUC Bst 3 as compared to the negative controls. By contrast, no new bands were visible in gel lanes corresponding to lysates made from host cells containing any of the pUC Bst 2 series of plasmids. The newly appearing bands from cells containing the pUC Bst 1 series of plasmids ran at approximately the same position as a 97 kDa molecular weight marker, while the new bands from host cells containing the pUC Bst 3 series of plasmids was several kDa smaller. These protein bands migrate at approximately the predicted size of the Bst DNA polymerase enzymes encoded by the particular plasmid construct.

The data obtained from these two experiments indicate several things. The Bst DNA polymerase gene is able to be expressed in $E.$ $coli$ host cells without the use of a heterologous promoter such as the lac promoter. Clones of the pUC Bst 1 series and pUC Bst 3 series contain approximately 600 base pairs of Bst genomic DNA flanking the 5' end of the polymerase gene. Although not wishing to be bound by theory, Applicant believes that expression of the DNA polymerase gene product is driven by at least one native promoter or promoter-like sequence in this region. Although these clones contain a lac promoter in the cloning vector, it is downstream from the polymerase gene and directs transcription in the opposite orientation than the Bst polymerase gene. Thus, this promoter would not be expected to function in expressing the polymerase gene.

Surprisingly, the recombinant Bst DNA polymerase gene of the present invention may be constitutively expressed in $E.$ $coli$ host cells without the use of an inducible or repressible promoter, such as the lac promoter under the control of the lac $I^q$ gene. By contrast, attempts to express full length DNA polymerase genes derived from other organisms using $E.$ $coli$ as a host cell have often been unsuccenssful. For example, Uemori, et al., $J.$ $Biochem.$ 113:401–410 (1983) and Joyce, et al., $J.$ $Biol.$ $Chem.$ 257:1958–1964 (1982) report that clones containing full length DNA polymerase genes are unstable, and the DNA polymerase gene can only be propagated as a Klenow-type fragment where the 5'-3' exonuclease activity is greatly diminished or absent. Although not wishing to be limited by theory, Applicants believe that the clones of the present invention may have improved stability by virtue of the $tet^r$ gene and by the relatively low activity level of Bst DNA polymerase at 37° C. as compared to the optimal temperature of 60° C. (Kaboev, et al., $J.$ $Bacteriol.$ 145:21–26 (1981).

The experiments demonstrate that the $tet^r$ clones in the $E.$ $coli$ 1200 host cell line expressed higher levels of enzyme activity than their non-tetr counterparts in the $E.$ $coli$ XL1-Blue MRF' host cell line. While not wishing to be bound by theory, the present Applicant believes that this is due to a lower frequency of reversion when the tet$^r$ gene is used as a selectable marker.

Clones containing the tet$^r$ gene in the (+) orientation (the same orientation as the cloned polymerase gene) also gave rise to higher levels of DNA polymerase activity than clones having the tet$^r$ gene in the (−) orientation.

Example 9

Comparison of pUC BST 1 T(+) derived Bst DNA polymerase with a commercial preparation of Bst DNA polymerase The full length Bst DNA polymerase was purified from a culture of *E. coli* 1200 cells containing plasmid pUC Bst 1 T(+) as described previously, and an aliquot was digested with subtilisin. The resulting large "Klenow-type" fragment, of approximately 66,000 Daltons, contained the DNA polymerase and 3' to 5' exonuclease domains, and was purified as detailed above. A commercial preparation of a Bst DNA polymerase subtilisin fragment, obtained from Bio-Rad Laboratories was purchased and used for comparison. The latter enzyme is reportedly directly purified from a strain of *B. stearothermophilus* prior to subtilisin cleavage; this strain is a different strain than the one used as the starting material for the compositions of the present invention. This enzyme is described in Ye and Hong, *Scientia Sinica* 30:503–506 (1987), and its use in DNA sequencing reactions is reported in Lu et al., *BioTechniques* 11:465–466 (1991), McClary et al., *DNA Sequence* 1: 173–180 (1991), and Mead et al., *BioTechniques* 11:76–87 (1991).

An assay of these two enzymes was performed using a nucleic acid having the same nucleotide sequence as a portion of the HIV genome as a template for DNA synthesis in nucleic acid amplification reactions performed as described in Ryder et al., U.S. patent application Ser. No. 08/097262, hereby incorporated by reference herein, and which enjoys common ownership with the present application. This method makes use of both DNA and RNA synthesis to amplify a nucleic acid sequence. Nucleic acid amplification was performed using 5 copies of the single-stranded HIV template and the same number of units of each DNA polymerase enzyme. The results of the comparison experiments are shown below and are expressed in relative light units (RLU).

|  | No added Bst | Bio-Rad Bst Subtilisin Fragment | Gen-Probe Bst 1 Subtilisin Fragment | Gen-Probe Bst 1 Full Length |
|---|---|---|---|---|
| No Template | 1,008 | 1,123 | 1,007 | 1,186 |
| Template | 897 | 499,250 | 431,779 | 398,745 |
|  | 938 | 478,090 | 412,632 | 414,696 |
|  | 966 | 511,314 | 421,338 | 317,848 |
|  | 993 | 499,573 | 392,560 | 441,114 |
|  | 959 | 464,196 | 399,665 | 326,355 |
| (Geometric Mean) | 950 | 490,188 | 411,349 | 376,510 |

The results indicate that both the full length and the subtilisin fragments of the recombinant enzymes of the present invention are able to promote the amplification of HIV DNA.

Example 10

Nucleic Acid Amplification in the Presence of a Cell Lysate from Normal White Blood Cells Another set of amplification reactions was performed as above, except the reactions were performed in the presence of of normal human white blood cell lysate purified from 0.5 ml of whole blood, as described in Ryder, supra. In this experiment, 10 copies of the HIV template DNA were used rather than 5 as in the previous experiment. The results were as indicated in the table below.

|  | No added Bst | Bio-Rad Subtilisin Fragment | Gen-Probe Bst 1 Subtilisin Fragment | Gen-Probe Bst 1 Full Length |
|---|---|---|---|---|
| No Template | 1,099 | 1,144 | 1,129 | 1,245 |
| Template | 1,123 | 1,002,133 | 1,088,906 | 1,009,661 |
|  | 1,095 | 1,041,312 | 1,035,826 | 1,007,071 |
|  | 1,058 | 1,030,350 | 1,000,339 | 1,020,751 |
| (Geometric Mean) | 1,091 | 1,024,464 | 1,014,911 | 1,012,476 |

These data indicate that both the full-length Bst DNA polymerase and the subtilisin-generated large fragment recombinant enzymes of the present invention supported amplification reactions in the presence of a cell lysate.

Example 11

Sensitivity Assay of Recombinant Bst DNA Polymerase Enzymes

Another set of nucleic acid amplification experiments was performed as in Example 9, except that the number of template molecules was lowered to either 2.5 or 0.5 copies per reaction, and both the pol and gag regions of the HIV genome were used as target sequences for primer binding and amplification. Detection of the resulting amplicons was performed as described in Ryder et al., supra, previously incorporated by reference. In place of the subtilisin large fragment of pUC Bst 1 T, a Bst DNA polymerase fragment of similar size, from *E. coli* 1200/pUC Bst 3 T(+) was used. This fragment is spontaneously produced by an endogenous protease activity during the purification of the pUC Bst 3 T enzyme.

| 2.5 Copies Template per Reaction | | | 0.5 Copies Template per Reaction | | |
|---|---|---|---|---|---|
| Commercial Subtilisin Fragment | pUC Bst 3 T Fragment | Full Length Enzyme | Commercial Subtilisin Fragment | pUC Bst 3 T Fragment | Full Length Enzyme |
| 75,351 | 1,414,081 | 1,514,059 | 685,121 | 4,937 | 1,778 |
| 880,648 | 1,137,354 | 2,101,167 | 973 | 5,909 | 2,248 |
| 125,304 | 1,515,839 | 1,565,670 | 481,529 | 52,426 | 1,355,728 |
| 384,228 | 2,173,285 | 1,585,148 | 906 | 647,230 | 1,465 |
| 430,392 | 356,737 | 1,879,384 | 290,032 | 18,428 | 1,796 |
| 3,019 | 968,199 | 942,562 | 780,481 | 20,518 | 1,666 |
| 492,167 | 1,351,785 | 944,147 | 1,122 | 878,148 | 1,632 |
| 433,327 | 2,468,726 | 423,967 | 1,100 | 352,646 | 1,215 |
| 729,439 | 1,374,685 | 684,638 | 2,241 | 1,251,116 | 4,698 |
| 232,912 | 2,414,018 | 642,848 | 8,149 | 4,384 | 21,432 |
| 207,839 (mean) | 1,351,069 (mean) | 1,094,169 (mean) | 16,484 (mean) | 60,301 (mean) | 4,651 (mean) |

These data indicate that, especially at the lower template levels, both the full length and "Klenow" forms of the preferred enzymes of the present invention support nucleic acid amplification reactions.

Example 12

N-terminal Sequencing of Selected DNA Polymerase Enzymes

In order to better understand the structure/function relationships between the different truncated Bst DNA polymerase enzymes, samples of the active subtilisin fragment ("Klenow" fragment) of Bst 1, a naturally-occuring breakdown product of the E. coli-expressed cloned Bst 3 DNA polymerase, and a biologically active subtilisin fragment from a preparation of an uncloned Bst DNA polymerase (obtained from Bio-Rad Laboratories, Inc.) were purified as described above, and subjected to N-terminal amino acid sequencing. Methods for amino acid sequence determination are well-known to those of skill in the art; such methods are described in Hewick et al., J. Biol. Chem. 256:7990–7997 (1981), the disclosure of which is hereby incorporated by reference herein. Automated methods of N-terminal amino acid sequence determination are also well known in the art; the amino acid sequencing described herein was performed using an Applied Biosystems-470A Gas-Phase sequencer with an in-line HPLC (Applied Biosystems, Foster City, Calif.) according to the manufacturer's instructions.

The polypeptides described above were subjected to amino acid sequence determination and the resulting sequences aligned and compared in the region corresponding to amino acid residue 285 of the full length Bst DNA polymerase (as encoded by the pUC Bst 1 clone). The resulting alignment is shown in FIG. 12; the amino acid sequences of Bst 1, Bst 2 and Bst 4 (see Example 13) are those predicted by the nucleic acid sequences. In the cases of Bst 2 and Bst 4, the translational start codon ATG (which encodes methionine) was the first codon of the coding region. Thus, these enzymes may have a Met residue at the N- terminus before the indicated residue. Alternatively, this residue may be removed by E. coli in the expressed protein. As can be seen, the subtilisin fragment of the full length Bst polymerase of the present invention is a polypeptide fragment beginning with a threonine residue corresponding to amino acid position 289 of the full length DNA polymerase. This peptide has DNA polymerase activity.

The Bst 2 protein, encoded by pUC Bst 2 in which a restriction fragment corresponding to the 5'-3' exonuclease domain of the full length protein had been engineered out of the Bst DNA polymerase gene, begins with aspartic acid. This amino acid occupies a position corresponding to amino acid 290 of the full length DNA polymerase, and is the second residue of the subtilisin fragment of Bst 1. This enzyme, as expressed in E. coli, is active in DNA polymerase assays, but at a lower level of activity than Bst 1 or its subtilisin fragment.

The protein expressed by cells including pUC Bst 3 is found in two forms. In the first of these forms, the uncleaved protein contains a deletion in the 5'-3' exonuclease domain of the full length Bst 1 protein. However, both proteins have the same N-terminus, and the region corresponding to amino acid residue 285 of the Bst 1 protein is similar in both proteins. The second form of the Bst 3 enzyme appears to be a cleavage product of the Bst 3 protein by an E. coli protease. This fragment begins with a valine as the first amino acid residue; this residue corresponds to amino acid 287 of the full length Bst polymerase clone of the present invention. The third residue of this proteolytic fragment is the threonine residue that begins the Bst 1 subtilisin fragment's amino acid sequence; the fourth residue is the aspartic acid residue which begins the amino acid sequence of the Bst 2 protein.

Surprisingly, the sequence information derived from the commercial Est DNA polymerase preparation ("Klenow" fragment) revealed that the N-terminal residue of this subtlisin fragment began with an alanine residue at a position corresponding to amino acid 290 of the full length Bst 1 protein sequence. As disclosed above, the Bst 2 protein begins with an aspartic acid residue at this position. All the other enzymes of the present invention that were sequenced in this region also showed an aspartic acid residue at this position. Moreover, the sequence of the N-terminal first 21 amino acids of this fragment revealed that 7 residues (or 33%) of the amino acids were different between the commercial, uncloned Bst DNA polymerase preparation and the enzymes of the present invention in this region. See FIG. 12.

Additionally, a comparison of the amino acid sequences of the proteins of the present invention with the published Bca DNA polymerase sequence shows that 12 out of 25 residues, or almost 50% of the amino acids, are different between the published Bca DNA polymerase sequence, previously incorporated by reference, and the Bst DNA polymerase of the present invention in this region (see FIG. 12). Overall, 105 out of 876 (almost 12%) of the amino acids of the Bst DNA polymerase amino acid sequence are not found in the corresponding position of the published Bca DNA polymerase sequence.

Example 13

Construction of a Bst DNA Polymerase (Bst 4) Having the Same N-Terminus as the Active Proteolytic Fragment of Bst 3

A plasmid clone was constructed similarly to the method used in the construction of plasmid pUC Bst 2 in order to encode a protein beginning with a valine residue and having the amino acid sequence of the naturally-occurring degradation product of Bst 3, as described in Example 12 above. The coding region of the DNA gene insert had a nucleotide sequence of SEQ ID NO: 26. The plasmid was used to transform strain 1200. A lysate from a culture of this transformant was electrophoresed by SDS-PAGE, and a protein band of the expected mobility was observed as shown in FIG. 14. This protein was termed Bst 4. The N-terminal amino acids predicted for the clone are indicated in FIG. 12, and the entire deduced amino acid sequence of Bst 4 is shown as SEQ ID NO: 27.

Figure 13:
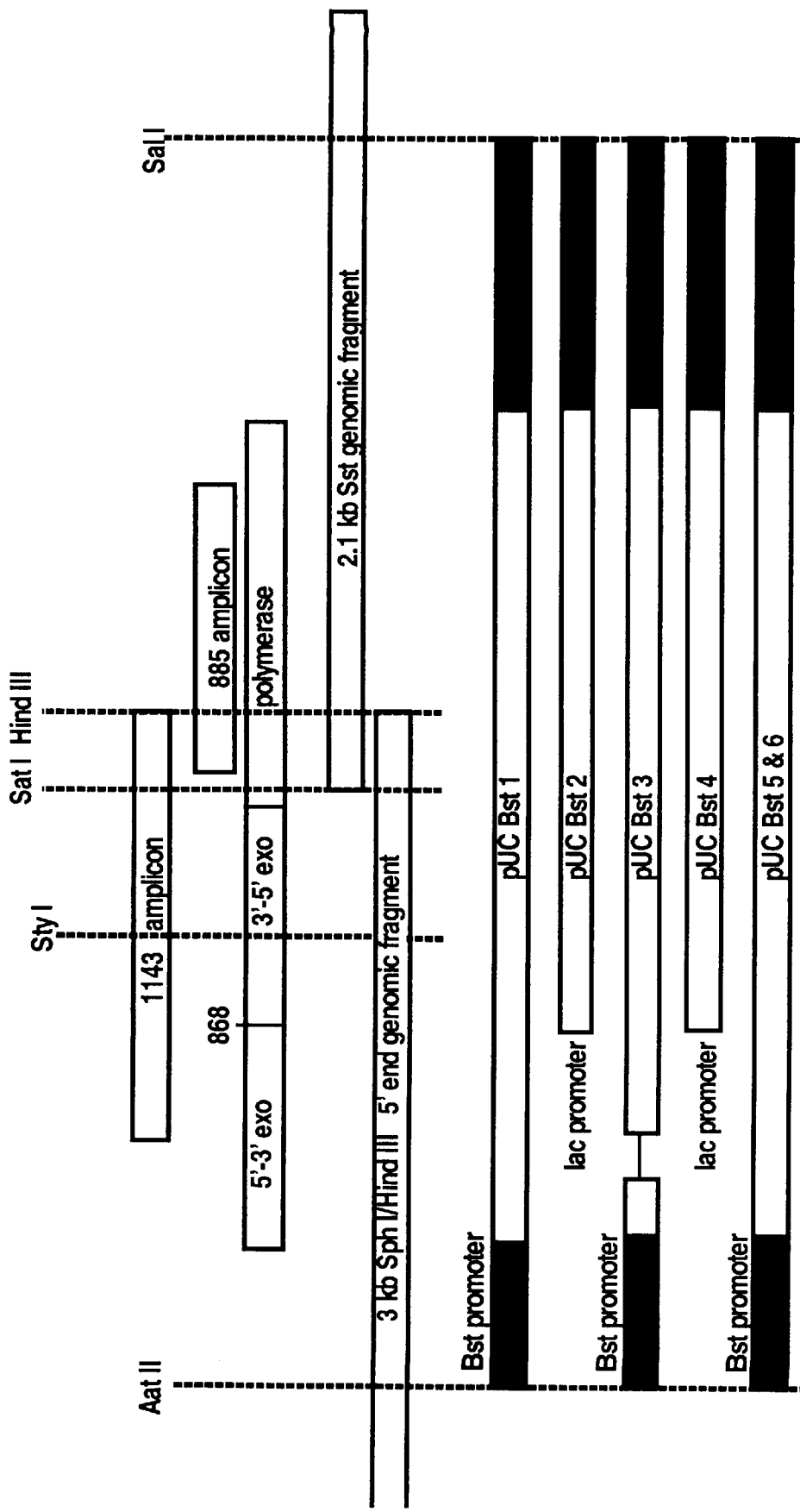
FIG. 13 is a schematic diagram of the relation of the Bst polymerase DNA inserts of pUC Bst 1, 2, 3, 4, 5 and 6, the 5' and 3' Bst genomic fragments, and the 1143 amplicon and the 885 amplicon to the Bst DNA polymerase gene and its three domains.

FIG. 13 shows a schematic diagram of the Bst DNA polymerase gene inserts and their relation to the genomic Bst gene and its 3 domains.

Example 14

Construction of Bst DNA Polymerase Point Mutants Lacking 5'-3' Exonuclease Activity Two different additional plasmid clones were constructed, each of which encoded Bst DNA polymerase enzymes having a single amino acid substitution in the 5'-3' exonuclease domain. Because a single substitution in this domain was unlikely to significantly affect the polymerase activity or expression of the enzyme, it was thought that such a substitution presented a strategy for constructing mutant enzymes with DNA polymerase activity but being defective in the 5'-3' exonuclease activity.

The first strategy was to cause the change of the tyrosine at position 73 of the wild-type Bst 1 enzyme (SEQ ID NO: 20) to a phenylalanine residue. This substitution was chosen because the hydroxyl group of the tyrosine residue would no longer be available for reaction at or near the active site of the 5'-3' exonuclease domain, but the overall conformation of the enzyme should be otherwise little affected, since the space-filling phenyl ring is common to both tyrosine and phenylalanine. The Phe$_{73}$ mutant is termed Bst 5 (SEQ ID NO: 32).

The other mutant enzyme, termed Bst 6 (SEQ ID NO: 34), results from the substitution of an alanine residue for the tyrosine at position 73 of the Bst 1 amino acid sequence. Since this residue not only replaces a polar group with a non-polar group, but replaces a sterically large amino acid side group with a much smaller side group, this substitution would be expected to change the conformation of the polymerase enzyme to a greater degree than was seen in Bst 5.

A diagramatic representation of the pUC Bst 5 and pUC Bst 6 DNA inserts in relation to the other Bst inserts (SEQ ID NO:31 and SEQ ID NO:33, respectively) and to the tnree domains of the Bst DNA polymerase gene is shown in FIG. 13.

Construction of Bst 5

Plasmid pUC Bst 1 was partially digested with Acc I and Xmn I restriction enzymes and electrophoresed on an agarose gel. An Acc I/Xmn I DNA band corresponding to the full length plasmid minus a 153 bp region from an Acc I site at Bst 1 (SEQ ID NO: 21) coordinate 103 to an Xmn I site at Bst 1 coordinate 256 was excised from the gel and gel purified using standard methods.

Synthetic oligonucleotides of SEQ ID NOs: 28 and 29 were synthesized using a method similar to that described in Example 4 above. Fifteen picomoles of each oligonucleotide were combined in duplicate reactions and incubated at 72° C. for 5 minutes in a solution of 20 mM Tris-HCl (pH 8.0), 2 mM MgCl2 and 50 mM KCl. The solutions were then cooled slowly to 40° C. to anneal the oligonucleotides, which had complementary nucleotide sequences at their 3' ends. The solutions were then given 0.2 mM each DNTP and 10 units of the Klenow fragment of E. coli DNA polymerase I to create a blunt-ended double-stranded DNA fragment which contained the native Bst DNA polymerase nucleotide sequence with the desired changes at the codon corresponding to amino acid 72 of the Bst DNA polymerase enzyme, as well as an Acc I site near the 5' end of the coding strand and an Xmn I site near the 3' end of the coding strand. A single degenerate mutation was also introduced by the synthetic oligonucleotides into the nucleotide sequence in order to create a new diagnostically useful restriction site; this mutation did not result in additional amino acid substitutions in the Bst enzyme. The reaction mixtures were incubated at 37° C. for 50 minutes. The duplicate reactions were pooled and extracted, first with phenol/chloroform, then with chloroform, and finally the double-standed oligonucleotide fragment was precipitated with ethanol. The resulting fragment was redissolved and phosphroylated using 30 units T4 polynucleotide kinase and 0.5 mM ATP at 37° C. for one hour.

Plasmid pGem-3Z (1.22 μg) was digested with 10 units of Sma I at room temperature for 65 minutes, then extracted with phenol/chloroform and chloroform alone. Approximately 11 picomoles of the phosphorylated synthetic double-stranded fragments were combined with 0.24 μg of the Sma I-digested plasmid pGem-3Z and the nucleic acids co-ethanol precipitated. The pellet was reconstituted and ligated using 15 units of T4 DNA ligase at room temperature overnight. The resulting ligation mixture was used to transform E. coli strain 1200, and the transformants plated onto LB agar plus ampicillin. Following incubation overnight at 37° C., ampicillin-resistant colonies were picked, grown in LB plus ampicillin, and the plasmids purified and screened using restriction endonuclease digestion (Xmn I). Clones were identified which had the expected synthetic DNA fragment insert; plasmid preparations were made of these clones and the plasmids were digested with Acc I and Xmn I. The restriction digests were then electrophoresed and the 153 bp fragment was gel isolated and ligated with the pUC Bst I fragment previously gel isolated as described above.

The ligation mixture was used to transform XL1-Blue MRF' cells, and the transformants were plated onto LB agar containing ampicillin. Ampicillin-resistant colonies were chosen, grown in LB plus ampicillin, and the plasmids purified and screened using restriction endonuclease digestion. The plasmids containing the expected Bst 5 insert were digested with Aat II and ligated with the 1435 bp tetracycline resistance gene fragment, as described in Example 7 above. The ligation mixture was used to transform E. coli strain 1200, and the transformants were plated onto LB agar containing tetracycline. Tetracycline resistant colonies were grown in LB plus tetracycline and the plasmids purified and screened using restriction endonuclease digestion. Clones containing the tetracycline resistance gene in both orientations were identified and named pUC Bst 5 T[+] and pUC Bst 5 T[-]. An SDS-PAGE analysis of the protein expressed by these transformants showed protein bands migrating at the position expected for Bst DNA polymerase. Lysates of these transformants displayed DNA polymerase activity. The plasmid DNA from these transformants was also sequenced in the region of the mutations and confirmed to have the expected DNA sequence within the Bst polymerase gene. The sequencing reactions were as described above.

Construction of Bst 6

Bst 6 was constructed exactly as was Bst 5, except the synthetic oligonucleotide pair used for this construction were oligonucleotides of SEQ ID NOS: 28 AND 30.

The tetracycline-resistant clones of Bst 6 having the tetracycline resistance gene in both orientations were named pUC Bst 6 T[+] and pUC Bst 6 T[-]. These also expressed a protein migrating on SDS-PAGE gels at the position correlating with Bst DNA polymerase and lysates from cultures of these transformants expressed a DNA polymerase activity. Sequencing of the plasmid DNA revealed the expected nucleotide sequence within the Bst 6 gene.

DNA Polymerase Activity Assays for Bst 5 and Bst 6

Cultures of each of the four Bst 5 and Bst 6 clones were grown overnight in LB plus tetracycline and analyzed for the expression of DNA polymerase activity as described in Example 8. Results of the assay are shown below.

| DNA Polymerase Activity at 60° C. (in RLU) | |
|---|---|
| pUC Bst 1 T [+] | 58,837 |
| pUC Bst 5 T [+] | 58,729 |
| pUC Bst 5 T [-] | 53,118 |
| pUC Bst 6 T [+] | 63,206 |
| pUC Bst 6 T [-] | 66,582 |
| pUC Tet [+] (negative control) | 704 |

Analysis of lysates from the Bst 5 and 6 clones by SDS-PAGE showed approximately equal amounts of a prominent band at around 97 KDa; this band was absent from a lysate from E. coli 1200/pUC Tet[+].

5'-3' Exonuclease Activity Assays of the Bst 5 and Bst 6 Clones

The Bst 5 and Bst 6 enzymes were purified in substantially the same manner as described above. The purified Bst 1, Bst 5 and Bst 6 enzymes, and the purified subtilisn DNA polymerase fragment from Bst 1 were assayed for 5'-3' exonuclease activity. Vent® DNA polymerase from New England Biolabs, which is known to be deficient in 5'-3' exonuclease activity, was used as a negative control. rTth DNA polymerase, obtained from Perkin Elmer, is known to contain a 5'-3' exonuclease activity; this was used as a positive control.

The assay was performed as follows. Plasmid pGem 3Z DNA was linearized using Hind III restriction endonuclease, then treated with alkaline phosphatase to dephosphorylate the 5' ends. The DNA was then labeled at the 5' ends with $^{32}P$ using T4 polynucleotide kinase, as described above. Approximately 0.015 pmoles (130,000 cpm) of this labeled substrate was used in each assay reaction.

For each assay of Bst 1, Bst 5, and Bst 6 enzymes, different amounts of each enzyme were added to the substrate nucleic acid in a reaction mixture containing 0.5 mM of each dNTP, 1.5 mM $MgCl_2$, 90 mM KCl and 10 mM Tris-HCl(pH 8.3); the total volume of each reaction was 50 µl. The reaction mixtures were incubated at 60° C. for 3 hours, then chilled on ice. Ten microliters of 10 mg/ml BSA was then added to each tube as a carrier, then each reaction tube was given 20 µl of cold 50% trichloroacetic acid. The tubes were incubated for 20 minutes on ice, then centrifuged for 5 minutes in a microcentrifuge. The supernatants and pellets were separated and each was counted in a scintillation counter for the presence of radioactivity. The percentage of total cpm released in the supernatant was used as a measure of 5'-3' exonuclease activity.

The Vent® and rTth enzymes were assayed in a similar manner with the following changes, made according to the manufacturer's instructions. For the Vent® enzyme, the enzyme was added to the substrate in a reaction mixture containing 0.5 mM each dNTP, 10 mM KCl, 10 mM $(NH_4)_2SO_4$, 20 mM Tris-HCl (pH 8.8), 2 mM $MgSO_4$, and 0.1% (v/v) Triton® X-100 in a total volume of 50 µl. The reaction mixtures were incubated at 70° C.

For the rTth enzyme, the enzyme was added to the same reaction mixture as for the Bst enzymes with the further addition of 0.6 mM MnCl2, 100 mM KCl, 0.75 mM EGTA, 0.05% (v/v) Tween® 20, and 5% (v/v) glycerol in a total volume of 50 µl. The reaction mixtures were incubated at 70° C.

Because the manufacturers' units of enzyme activity are not the same as Gen-Probe's units of enzyme activity, the concentrations of enzyme added to the Vent® and rTth reactions was based on the amount of enzyme determined to be active in DNA polymerase assays.

The following table presents data which are the averages of duplicate assays.

| | 5'-3' Exonuclease Assay | |
|---|---|---|
| | Gen-Probe Units or Manufacturer's Units | % cpm in supernatant |
| Bst 1 | 96,000 | 95 |
| | 19,100 | 69 |
| | 2,000 | 26 |
| | 200 | 12 |
| Bst 5 | 136,100 | 16 |
| | 68,000 | 15 |
| | 27,200 | 15 |
| | 2,700 | 13 |
| Bst 6 | 136,100 | 17 |
| | 68,000 | 18 |
| | 27,200 | 18 |
| | 2,700 | 14 |
| Bst 1 subtilisin fragment | 78,500 no enzyme | 17 13 |
| rTth (+) control | 25 (Mfr's units) no enzyme | 42 13 |
| Vent ® (-) control | 5 (Mfr's units) no enzyme | 16 14 |

These data shown that the Bst 5 and Bst 6 enzymes do not contain detectable 5'-3' exonuclease activities, even at high enzyme concentrations. The data also confirm that the purified subtilisin polymerase fragment of Bst 1 also contains no detectable 5'-3' exonuclease activity.

Example 15

Ability of Bst 5 and Bst 6 to support Nucleic Acid Amplification

The purified Bst enzymes were tested for their ability to support nucleic acid amplification. Nucleic acid amplification was performed substantially as described in Example 9, except the commercial source of the non-recombinant Bst DNA polymerase subtilisin fragment was Molecular Biological Resources (Milwaukee Wis.). An equal number of units of each enzyme was used for each assay.

| Copies of HIV Template | Commercial Subtilisin Fragment of Native Enzyme | Bst-1 | Subtilisin Bst-1 | Bst-5 | Bst-5 |
| --- | --- | --- | --- | --- | --- |
| 5 | 2,538,405 | 2,190,958 | 2,680,877 | 2,560,438 | 2,600,262 |
|  | 2,503,380 | 2,520,161 | 2,645,578 | 2,571,370 | 2,651,576 |
|  | 2,654,329 | 2,651,948 | 2,703,753 | 2,433,015 | 2,630,750 |
|  | 2,714,339 | 2,486,977 | 2,581,356 | 2,495,086 | 2,658,697 |
|  | 2,572,544 | 2,521,970 | 2,622,247 | 2,492,034 | 2,686,534 |
|  | 2,700,737 | 2,624,428 | 2,601,453 | 2,401,619 | 2,655,092 |
|  | 2,719,892 | 2,574,901 | 2,638,163 | 2,639,461 | 2,667,916 |
|  | 2,712,654 | 2,572,914 | 2,638,399 | 2,294,487 | 2,672,463 |
|  | 2,603,278 | 2,633,240 | 2,535,452 | 2,675,323 | 2,663,664 |
| 0 | 7,016 | 5,114 | 6,698 | 6,845 | 6,449 |

Example 16

Use of purified Bst 1 subtilisin fragment and Bst 5 and 6 enzymes in sequencing reactions Bst 1, Bst 5 and Bst 6 enzymes and the subtilisin fragment from the Bst 1 clone were purified as described above and tested for their ability to support sequencing reactions. Sequencing reactions were done using the Bio-Rad (Hercules, Calif.) Bst sequencing reagents according to the manufacturers protocol and were compared with reactions done using the Bio-Rad Bst DNA polymerase, which is the subtilisin fragment of the non-recombinant (native) enzyme. The primer and template used were the T7 promoter-primer and pGem 3Z plasmid obtained from Promega Corp.

Both the Bst 1 and native enzyme subtilisin fragments, as well as both of the Bst 5 and 6 enzymes, produced clear sequencing ladders, whereas the use of the Bst 1 holoenzyme resulted in no signal at all. Because the full length Bst 1 enzyme has a 5'-3' exonuclease activity, the rate of degradation of newly synthesized stands is in equilibrium with the rate of synthesis of these strands, and sequencing is not effective. Thus, the results indicate the single amino acid substitutions of the Bst 5 and 6 enzymes have eliminated the undesired 5'-3' exonuclease activity to the extent that the Bst 5 and Bst 6 enzymes are comparable to the subtilisin fragment of Bst DNA polymerase in these sequencing reactions, with the added advantage of obviating the need for subtilisin digestion and repurification.

The foregoing examples exemplify various embodiments of the present invention and are not intended to limit the invention, the scope of the invention and its equivalents being determined solely by the claims which follow.

What is claimed is:

1. A purified protein expressed from a gene derived from *Bacillus stearothermophilus* and produced in a heterologous host cell and having an apparent molecular weight of about 60,000 Daltons, comprising an amino acid sequence of SEQ ID NO:23, SEQ ID NO:25, SEQ ID NO:27, or a methionine residue followed by any one of SEQ ID NO:23, SEQ ID NO:25, or SEQ ID NO:27.

2. The purified protein of claim 1, wherein said protein has a DNA polymerase activity.

3. The purified protein of claim 2, wherein said protein has a reduced 5'-3' exonuclease activity compared to that of a *Bacillus stearothermophilus* DNA polymerase having an apparent molecular weight of about 98,000 Daltons.

4. A purified thermostable DNA polymerase enzyme produced by expression of a gene encoding a DNA polymerase derived from *Bacillus stearothermnophilus* strain ATCC 12980 in an *E. coli* host cell, wherein said enzyme is a proteolytic cleavage product of said *B. stearothermophilus* DNA polymerase enzyme.

5. The purified thermostable DNA polymerase enzyme of claim 4. produced by protease digestion in vitro of the *B. stearothermophilus* DNA polymerase enzyme.

6. The purified thermostable DNA polymerase enzyme of claim 5, wherein said protease digestion is performed using subtilisin.

7. The enzyme of claim 4 wherein said enzyme has a reduced 5'-3' exonuclease activity compared to that of a nonproteolyzed *B. stearothermophilus* DNA polymerase.

8. The enzyme of claim 5 wherein said enzyme has a reduced 5'-3' exonuclease activity compared to that of a nonproteolyzed *B. stearothermophilus* DNA polymerase.

9. A purified thermostable DNA polymerase enzyme derived from *Bacillus stearothemophilus* ATCC strain 12980 having reduced 5'-3' exonuclease activity due to deletion of amino acids of the 5'-3' exonuclease domain of a full length *Bacillus stearothemophilus* DNA polymerase.

10. The purified protein of claim 1, wherein the protein has the amino acid sequence of SEQ ID NO:23 or a methionine residue followed by the amino acid sequence of SEQ ID NO:23.

11. The purified protein of claim 1, wherein the protein has the amino acid sequence of SEQ ID NO:25 or a methionine residue followed by the amino acid sequence of SEQ ID NO:25.

12. The purified protein of claim 1, wherein the protein has the amino acid sequence of SEQ ID NO:27 or a methionine residue followed by the amino acid sequence of SEQ ID NO:27.

13. The purified protein of claim 1, wherein the host cell is *E. coli*.

14. The purified protein of claim 13, wherein the host cell is *E. coli* strain 1200.

15. The purified thermostable DNA polymerase enzyme of claim 4, produced by protease digestion of the *B. stearothernophilus* DNA polymerase enzyme during purification from the *E. coli* host cell.

16. The purified thermostable DNA polymerase enzyme of claim 15, wherein said enzyme has a reduced 5'-3' exonuclease activity compared to that of a nonproteolyzed *B. stearothenmophilus* DNA polymerase.

17. The purified thermostable DNA polymerase enzyme of claim 9, wherein the deletion of amino acids removes about 65 amino acids from the 5'-3' exonuclease domain.

18. The purified thermostable DNA polymerase enzyme of claim 9, wherein the enzyme has an amino acid sequence beginning at the amino acid corresponding to amino acid residue 285 of a full length *B. stearothermophilus* DNA polymerase.

19. The purified thermostable DNA polymerase enzyme of claim 9, wherein the enzyme has an amino acid sequence beginning at the amino acid corresponding to amino acid residue 287 of a full length *B. stearothermophilus* DNA polymerase.

20. The purified thermostable DNA polymerase enzyme of claim 9, wherein the enzyme has an amino acid sequence beginning at the amino acid corresponding to amino acid residue 289 of a full length *B. stearothennophilus* DNA polymerase.

21. The purified thermostable DNA polymerase enzyme of claim 9, wherein the enzyme has an amino acid sequence beginning at the amino acid corresponding to amino acid residue 290 of a full length *B. stearothennophilus* DNA polymerase.

* * * * *